United States Patent
Rudnicki et al.

(10) Patent No.: US 9,018,188 B2
(45) Date of Patent: Apr. 28, 2015

(54) MICRORNA INHIBITORS

(75) Inventors: Michael A. Rudnicki, Ottawa (CA);
Hang Yin, Ottawa (CA)

(73) Assignee: Ottawa Hospital Research Institute, Ottawa, Ontario (CA)

( * ) Notice: Subject to any disclaimer, the term of this patent is extended or adjusted under 35 U.S.C. 154(b) by 0 days.

(21) Appl. No.: 14/241,826

(22) PCT Filed: Sep. 13, 2012

(86) PCT No.: PCT/CA2012/050636
§ 371 (c)(1),
(2), (4) Date: Feb. 27, 2014

(87) PCT Pub. No.: WO2013/037065
PCT Pub. Date: Mar. 21, 2013

(65) Prior Publication Data
US 2014/0221466 A1    Aug. 7, 2014

Related U.S. Application Data

(60) Provisional application No. 61/534,107, filed on Sep. 13, 2011.

(51) Int. Cl.
| | | |
|---|---|---|
| *A61K 48/00* | (2006.01) | |
| *C07H 21/02* | (2006.01) | |
| *C07H 21/04* | (2006.01) | |
| *C12Q 1/68* | (2006.01) | |
| *A61K 31/7105* | (2006.01) | |
| *A61K 31/7125* | (2006.01) | |
| *C12N 15/113* | (2010.01) | |
| *G01N 33/68* | (2006.01) | |
| *A61K 31/711* | (2006.01) | |

(52) U.S. Cl.
CPC .......... *C12Q 1/6897* (2013.01); *A61K 31/7105* (2013.01); *A61K 31/7125* (2013.01); *C12N 15/113* (2013.01); *G01N 33/6893* (2013.01); *C12N 2310/113* (2013.01); *C12N 2310/315* (2013.01); *C12N 2310/3181* (2013.01); *C12N 2310/346* (2013.01); *C12N 2310/3515* (2013.01); *C12N 2320/10* (2013.01); *A61K 31/711* (2013.01)

(58) Field of Classification Search
USPC ............................................ 514/44; 536/24.5
See application file for complete search history.

(56) References Cited

U.S. PATENT DOCUMENTS

2009/0326051 A1* 12/2009 Corey et al. ................. 514/44 R
2010/0292297 A1   11/2010 Wang et al.

FOREIGN PATENT DOCUMENTS

WO    2008/015028    2/2008

OTHER PUBLICATIONS

Yin et al. (Cell Metabolism, 2013, vol. 17:210-224).*
(Continued)

*Primary Examiner* — Terra C Gibbs
(74) *Attorney, Agent, or Firm* — Gail C. Silver; Borden Ladner Gervais LLP

(57) ABSTRACT

The present invention relates to microRNAs (miRNAs) that are associated with obesity. The present invention is directed to methods, compounds, and compositions for preventing and treating obesity, as well as related diseases, using a microRNA inhibitor.

16 Claims, 22 Drawing Sheets

(56) References Cited

OTHER PUBLICATIONS

Chiba, Y. et al. Down-regulation of miR-133a contributes to up-regulation of 1-3, 6, 15RhoA in bronchial smooth muscle cells. American Journal of Respiratory and A Critical Care Medicine, issue of Oct. 2009, vol. 180, No. 8, 4, 5, 7-14, 20-23pages 713-719, ISSN 1535-4970.

Almind, K., Manieri, M., Sivitz, W.I., Cinti, S., and Kahn, C.R. (2007). Ectopic brown adipose tissue in muscle provides a mechanism for differences in risk of metabolic syndrome in mice. Proc Natl Acad Sci U S A 104, 2366-2371.

Atit, R., Sgaier, S.K., Mohamed, O.A., Taketo, M.M., Dufort, D., Joyner, A.L., Niswander, L., and Conlon, R.A. (2006). Beta-catenin activation is necessary and sufficient to specify the dorsal dermal fate in the mouse. Dev Biol 296, 164-176.

Bachmanov, A.A., Reed, D.R., Beauchamp, G.K., and Tordoff, M.G. (2002). Food intake, water intake, and drinking spout side preference of 28 mouse strains. Behav Genet 32, 435-443.

Bosnakovski, D., Xu, Z., Li, W., Thet, S., Cleaver, O., Perlingeiro, R.C., and Kyba, M. (2008). Prospective isolation of skeletal muscle stem cells with a Pax7 reporter. Stem Cells 26, 3194-3204.

Bowman, W.C., and Nott, M.W. (1969). Actions of sympathomimetic amines and their antagonists on skeletal muscle. Pharmacol Rev 21, 27-72.

Cannon, B., and Nedergaard, J. (2004). Brown adipose tissue: function and physiological significance. Physiol Rev 84, 277-359.

Charge, S.B., and Rudnicki, M.A. (2004). Cellular and molecular regulation of muscle regeneration. Physiol Rev 84, 209-238.

Chen, J.F., Mandel, E.M., Thomson, J.M., Wu, Q., Callis, T.E., Hammond, S.M., Conlon, F.L., and Wang, D.Z. (2006). The role of microRNA-1 and microRNA-133 in skeletal muscle proliferation and differentiation. Nat Genet 38, 228-233.

Cypess, A.M., and Kahn, C.R. (2010). Brown fat as a therapy for obesity and diabetes. Curr Opin Endocrinol Diabetes Obes 17, 143-149.

Cypess, A.M., Lehman, S., Williams, G., Tal, I., Rodman, D., Goldfine, A.B., Kuo, F.C., Palmer, E.L., Tseng, Y.H., Doria, A., et al. (2009). Identification and importance of brown adipose tissue in adult humans. N Engl J Med 360, 1509-1517.

Dellavalle, A., Maroli, G., Covarello, D., Azzoni, E., Innocenzi, A., Perani, L., Antonini, S., Sambasivan, R., Brunelli, S., Tajbakhsh, S., et al. (2011). Pericytes resident in postnatal skeletal muscle differentiate into muscle fibres and generate satellite cells. Nat Commun 2, 499.

Farmer, S. R. (2008). Brown fat and skeletal muscle: unlikely cousins? Cell 134 726.

Frontini, A., and Cinti, S. (2010). Distribution and development of brown adipocytes in the murine and human adipose organ. Cell Metab 11, 253-256.

Ghorbani, M., and Himms-Hagen, J. (1997). Appearance of brown adipocytes in white adipose tissue during CL 316,243-induced reversal of obesity and diabetes in Zucker fa/fa rats. Int J Obes Relat Metab Disord 21, 465-475.

Gnaiger, E. (2009a). Capacity of oxidative phosphorylation in human skeletal muscle: new perspectives of mitochondrial physiology. Int J Biochem Cell Biol 41, 1837-1845.

Granjon, A., Gustin, M.P., Rieusset, J., Lefai, E., Meugnier, E., Guller, I., Cerutti, C., Paultre, C., Disse, E., Rabasa-Lhoret, R., et al. (2009). The microRNA signature in response to insulin reveals its implication in the transcriptional action of insulin in human skeletal muscle and the role of a sterol regulatory element-binding protein-1c/myocyte enhancer factor 2C pathway. Diabetes 58, 2555-2564.

Gupta, R.K., Mepani, R.J., Kleiner, S., Lo, J.C., Khandekar, M.J., Cohen, P., Frontini, A., Bhowmick, D.C., Ye, L., Cinti, S., et al. (2012). Zfp423 expression identifies committed preadipocytes and localizes to adipose endothelial and perivascular cells. Cell Metab 15, 230-239.

Himms-Hagen J. (1979) Can Med Assoc J. 121(10):1361-4. Review.
Himms-Hagen J, Cui J, Danforth E Jr, Taatjes DJ, Lang SS, Waters BL, Claus TH. Am J Physiol. (1994) 266(4 Pt 2): R1371-82.

Ishibashi, J. and Seale, P., (May 28, 2011). Beige can be Slimming. Science 328(5982): 1113-1114.

Joe, A.W., Yi, L., Natarajan, A., Le Grand, F., So, L., Wang, J., Rudnicki, M.A., and Rossi, F.M. (2010). Muscle injury activates resident fibro/adipogenic progenitors that facilitate myogenesis. Nat Cell Biol 12, 153-163.

Kalaany, N.Y., Gauthier, K.C., Zavacki, A.M., Mammen, P.P., Kitazume, T., Peterson, J.A., Horton, J.D., Garry, D.J., Bianco, A.C., and Mangelsdorf, D.J. (2005). LXRs regulate the balance between fat storage and oxidation. Cell Metab 1, 231-244.

Kajimura, S., Seale, P., Tomaru, T., Erdjument-Bromage, H., Cooper, M.P., Ruas, J.L., Chin, S., Tempst, P., Lazar, M.A., and Spiegelman, B.M. (2008). Regulation of the brown and white fat gene programs through a PRDM16/CtBP transcriptional complex. Genes Dev 22, 1397-1409.

Kopecky, J., Clarke, G., Enerback, S., Spiegelman, B., and Kozak, L.P. (1995). Expression of the mitochondrial uncoupling protein gene from the aP2 gene promoter prevents genetic obesity. J Clin Invest 96, 2914-2923.

Krief, S., Lonnqvist, F., Raimbault, S., Baude, B., Van Spronsen, A., Arner, P., Strosberg, A.D., Ricquier, D., and Emorine, L.J. (1993). Tissue distribution of beta 3-adrenergic receptor mRNA in man. J Clin Invest 91, 344-349.

Krutzfeldt, J., Rajewsky, N., Braich, R., Rajeev, K.G., Tuschl, T., Manoharan, M., and Stoffel, M. (2005). Silencing of microRNAs in vivo with 'antagomirs'. Nature 438, 685-689.

Kuang, S., Kuroda, K., Le Grand, F., and Rudnicki, M.A. (2007). Asymmetric self-renewal and commitment of satellite stem cells in muscle. Cell 129, 999-1010.

Larsen, S., Nielsen, J., Hansen, C.N., Nielsen, L.B., Wibrand, F., Stride, N., Schroder, H.D., Boushel, R., Helge, J.W., Dela, F., et al. (2012). Biomarkers of mitochondrial content in skeletal muscle of healthy young human subjects. J Physiol 590, 3349-3360.

Lepper, C., and Fan, C.M. (2010). Inducible lineage tracing of Pax7-descendant cells reveals embryonic origin of adult satellite cells. Genesis 48, 424-436.

Matthias, A., Ohlson, K.B., Fredriksson, J.M., Jacobsson, A., Nedergaard, J., and Cannon, B. (2000). Thermogenic responses in brown fat cells are fully UCP1-dependent. UCP2 or UCP3 do not substitute for UCP1 in adrenergically or fatty scid-induced thermogenesis. J Biol Chem 275, 25073-25081.

Nedergaard, J., Bengtsson, T., and Cannon, B. (2007). Unexpected evidence for active brown adipose tissue in adult humans. Am J Physiol Endocrinol Metab 293, E444-452.

Nedergaard, J., Bengtsson, T., and Cannon, B. (2010). Three years with adult human brown adipose tissue. Ann N Y Acad Sci 1212, E20-36.

Nielsen, S., Scheele, C., Yfanti, C., Akerstrom, T., Nielsen, A.R., Pedersen, B.K., and Laye, M.J. (2010). Muscle specific microRNAs are regulated by endurance exercise in human skeletal muscle. J Physiol 588, 4029-4037.

Nishijo, K., Hosoyama, T., Bjornson, C.R., Schaffer, B.S., Prajapati, S.I., Bahadur, A.N., Hansen, M.S., Blandford, M.C., McCleish, A.T., Rubin, B.P., et al. (2009). Biomarker system for studying muscle, stem cells, and cancer in vivo. Faseb J 23, 2681-2690.

Ouellet, V., Labbe, S.M., Blondin, D.P., Phoenix, S., Guerin, B., Haman, F., Turcotte, E.E., Richard, D., and Carpentier, A.C. (2012). Brown adipose tissue oxidative metabolism contributes to energy expenditure during acute cold exposure in humans. J Clin Invest 122, 545-552.

Pesta, D., and Gnaiger, E. (2011). High-Resolution Respirometry. OXPHOS Protocols for Human Cell Cultures and Permeabilized Fibres from Small Biopsies of Human Muscle. Mitochondrial Bioenergetics: Methods and Protocols 810, 25-58.

Pesta, D., Hoppel, F., Macek, C., Messner, H., Faulhaber, M., Kobel, C., Parson, W., Burtscher, M., Schocke, M., and Gnaiger, E. (2011). Similar qualitative and quantitative changes of mitochondrial respiration following strength and endurance training in normoxia and hypoxia in sedentary humans. Am J Physiol Regul Integr Comp Physiol 301, R1078-1087.

Pfannenberg, C., Werner, M.K., Ripkens, S., Stef, I., Decker, A., Schmadl, M., Reimold, M., Haring, H.U., Claussen, C.D., and

(56) References Cited

OTHER PUBLICATIONS

Stefan, N. (2010). Impact of age on the relationships of brown adipose tissue with sex and adiposity in humans. Diabetes 59, 1789-1793.
Rodeheffer, M.S., Birsoy, K., and Friedman, J.M. (2008). Identification of white adipocyte progenitor cells in vivo. Cell 135, 240-249.
Rudnicki, M.A., Le Grand, F., McKinnell, I., and Kuang, S. (2008). The molecular regulation of muscle stem cell function. Cold Spring Harb Symp Quant Biol 73, 323-331.
Saito, M., Okamatsu-Ogura, Y., Matsushita, M., Watanabe, K., Yoneshiro, T., Nio-Kobayashi, J., Iwanaga, T., Miyagawa, M., Kameya, T., Nakada, K., et al. (2009). High incidence of metabolically active brown adipose tissue in healthy adult humans: effects of cold exposure and adiposity. Diabetes 58, 1526-1531.
Saks, V.A., Veksler, V.I., Kuznetsov, A.V., Kay, L., Sikk, P., Tiivel, T., Tranqui, L., Olivares, J., Winkler, K., Wiedemann, F., et al. (1998). Permeabilized cell and skinned fiber techniques in studies of mitochondrial function in vivo. Mol Cell Biochem 184, 81-100.
Scime, A., Grenier, G., Huh, M.S., Gillespie, M.A., Bevilacqua, L., Harper, M.E., and Rudnicki, M.A. (2005). Rb and p107 regulate preadipocyte differentiation into white versus brown fat through repression of PGC-1alpha. Cell Metab 2, 283-295.
Seale, P., Bjork, B., Yang, W., Kajimura, S., Chin, S., Kuang, S., Scime, A., Devarakonda, S., Conroe, H.M., Erdjument-Bromage, H., et al. (2008). PRDM16 controls a brown fat/skeletal muscle switch. Nature 454, 961-967.
Seale, P., Conroe, H.M., Estall, J., Kajimura, S., Frontini, A., Ishibashi, J., Cohen, P., Cinti, S., and Spiegelman, B.M. (2011). Prdm16 determines the thermogenic program of subcutaneous white adipose tissue in mice. J Clin Invest 121, 96-105.
Seale, P., Kajimura, S., Yang, W., Chin, S., Rohas, L.M., Uldry, M., Tavernier, G., Langin, D., and Spiegelman, B.M. (2007). Transcriptional control of brown fat determination by PRDM16. Cell Metab 6, 38-54.
Seale, P., Sabourin, L.A., Girgis-Gabardo, A., Mansouri, A., Gruss, P., and Rudnicki, M.A. (2000). Pax7 is required for the specification of myogenic satellite cells. Cell 102, 777-786.
Shi, R., and Chiang, V.L. (2005). Facile means for quantifying microRNA expression by real-time PCR. Biotechniques 39, 519-525.
Tallquist, M.D., Weismann, K.E., Hellstrom, M., and Soriano, P. (2000). Early myotome specification regulates PDGFA expression and axial skeleton development. Development 127, 5059-5070.
Tran, K.V., Gealekman, O., Frontini, A., Zingaretti, M.C., Morroni, M., Giordano, A., Smorlesi, A., Perugini, J., De Matteis, R., Sbarbati, A., et al. (2012). The vascular endothelium of the adipose tissue gives rise to both white and brown fat cells. Cell Metab 15, 222-229.
van Marken Lichtenbelt, W.D., Vanhommerig, J.W., Smulders, N.M., Drossaerts, J.M., Kemerink, G.J., Bouvy, N.D., Schrauwen, P., and Teule, G.J. (2009). Cold-activated brown adipose tissue in healthy men. N Engl J Med 360, 1500-1508.
Virtanen, K.A., Lidell, M.E., Orava, J., Heglind, M., Westergren, R., Niemi, T., Taittonen, M., Laine, J., Savisto, N.J., Enerback, S., et al. (2009). Functional brown adipose tissue in healthy adults. N Engl J Med 360, 1518-1525.
Walden, T.B., Timmons, J.A., Keller, P., Nedergaard, J., and Cannon, B. (2009). Distinct expression of muscle-specific microRNAs (myomirs) in brown adipocytes. J Cell Physiol 218, 444-449.
Wang, Y.X., and Rudnicki, M.A. (2011). Satellite cells, the engines of muscle repair. Nat Rev Mol Cell Biol 13, 127-133.
Williams, A.H., Liu, N., van Rooij, E., and Olson, E.N. (2009). MicroRNA control of muscle development and disease. Curr Opin Cell Biol 21, 461-469.
Wu, J., Bostrom, P., Sparks, L. M., Ye, L., Choi, J. H., Giang, A.-H., Khandekar, M., Virtanen, K. A., Nuutila, P., Schaart, G., Huang, K., Tu, H., van Markern Lichtenbelt, W., Hoeks, J., Enerback, S., Schrauwen, P., Speigelman, B.M. (2012) Beige adipocytes are a disctinct type of thermogenic fat cell in mouse and human. Cell 150 (2), 366-376.
Zingaretti, M.C., Crosta, F., Vitali, A., Guerrieri, M., Frontini, A., Cannon, B., Nedergaard, J., and Cinti, S. (2009). The presence of UCP1 demonstrates that metabolically active adipose tissue in the neck of adult humans truly represents brown adipose tissue. Faseb J 23, 3113-3120.
Lu, Y. et al. A single anti-microRNA antisense oligodeoxyribonucleotide (AMO) targeting multiple microRNAs offers an improved approach for microRNAA interference. Nucleic Acids Research (online), issue of Jan. 2009 vol. 37, No. 3, p. e24 (1-10), ISSN 1362-4962.
Fred, R.G. et al. High glucose suppresses human islet insulin biosynthesis by inducing miR-133a leading to decreased polypyrimidine tract binding protein-A expression. PloS ONE (online), issue of May 2010 vol. 5, No. 5, p. e10843 (1-9), ISSN 1932-6203.
PCT Search Report and Written Opinion, mailed Dec. 14, 2012.
PCT International Preliminary Report on Patentability, issued Mar. 18, 2013.

\* cited by examiner miR-133a is SEQ ID NO:4
miR133b is SEQ ID NO:5
Mouse Prdm16 3' UTR is SEQ ID NO:22
Human Prdm16 3' UTR is SEQ ID NO:23
Zebra fish Prdm16 3' UTR is SEQ ID NO:24
Frog Prdm16 3' UTR is SEQ ID NO:25
Mutated 3'UTR is SEQ ID NO:26

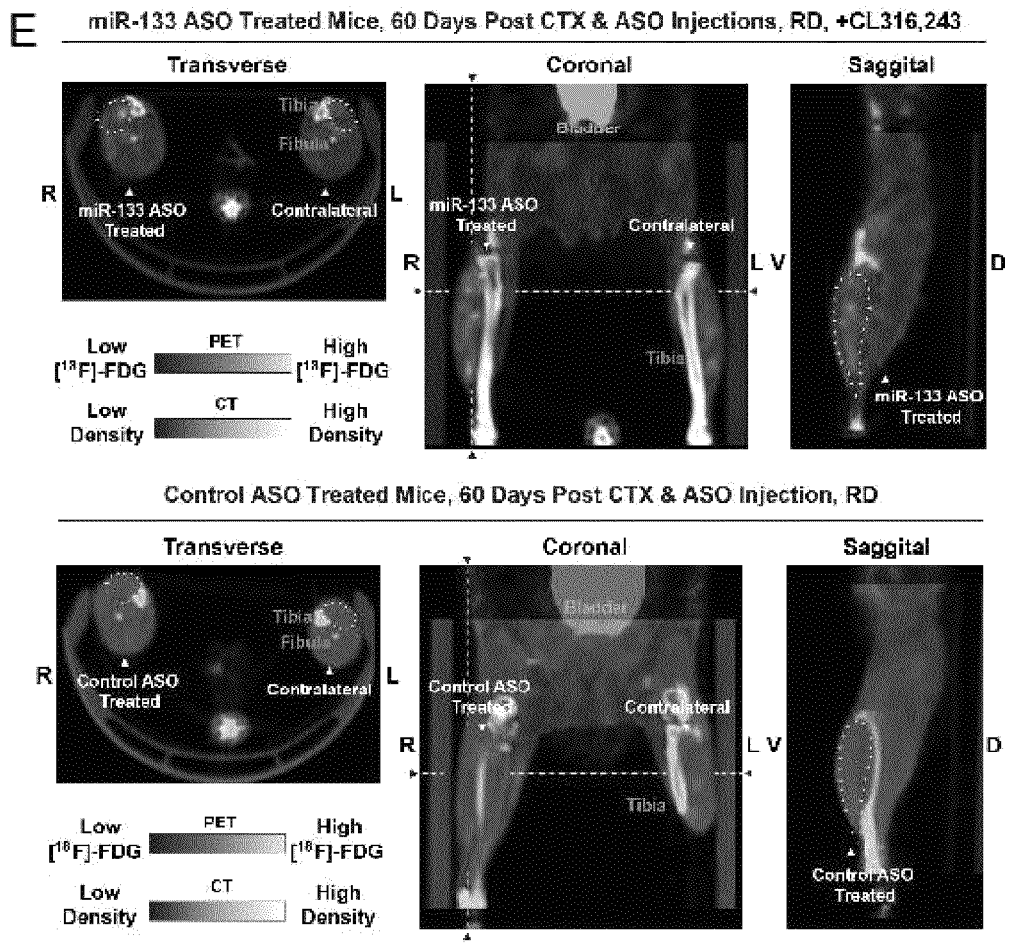
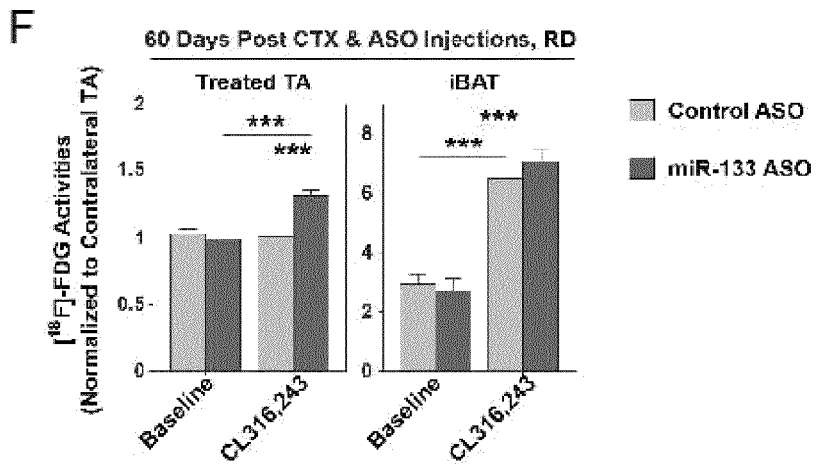
Fig. 5E and F

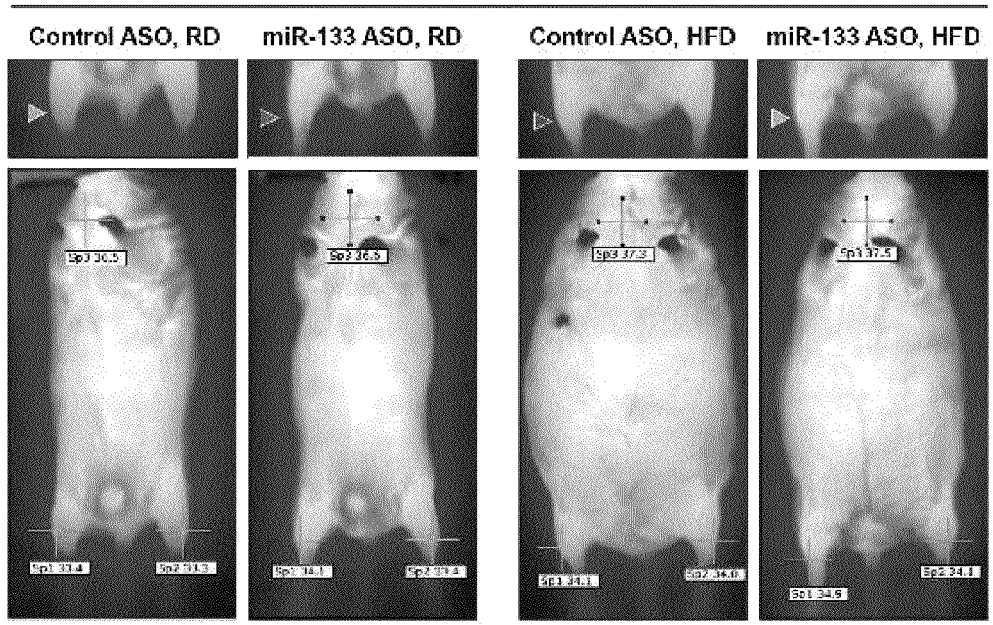
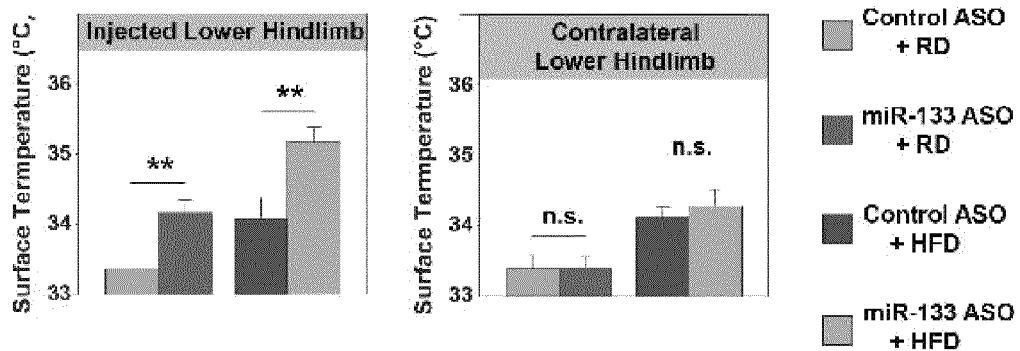
Fig 5G and H

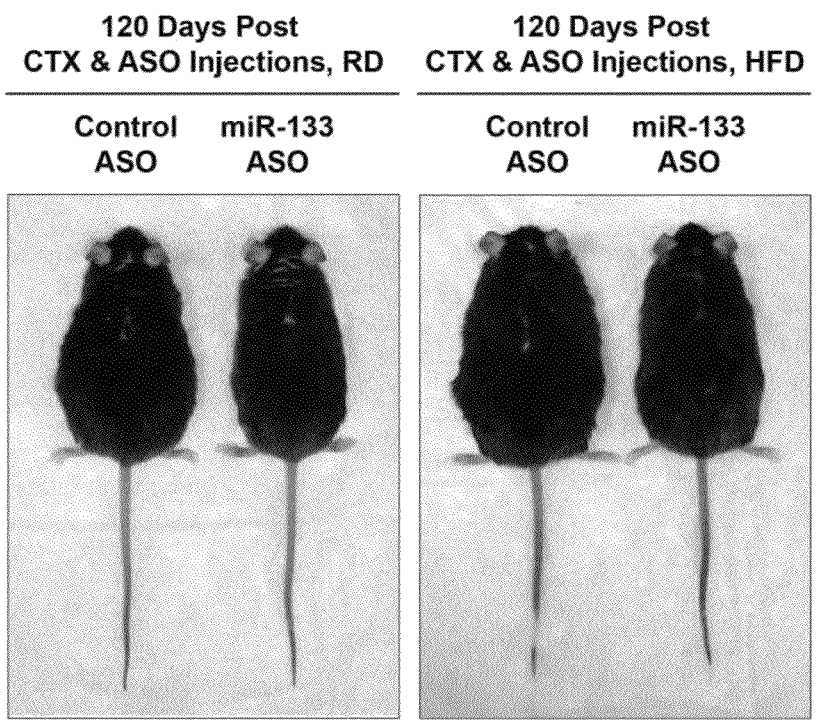
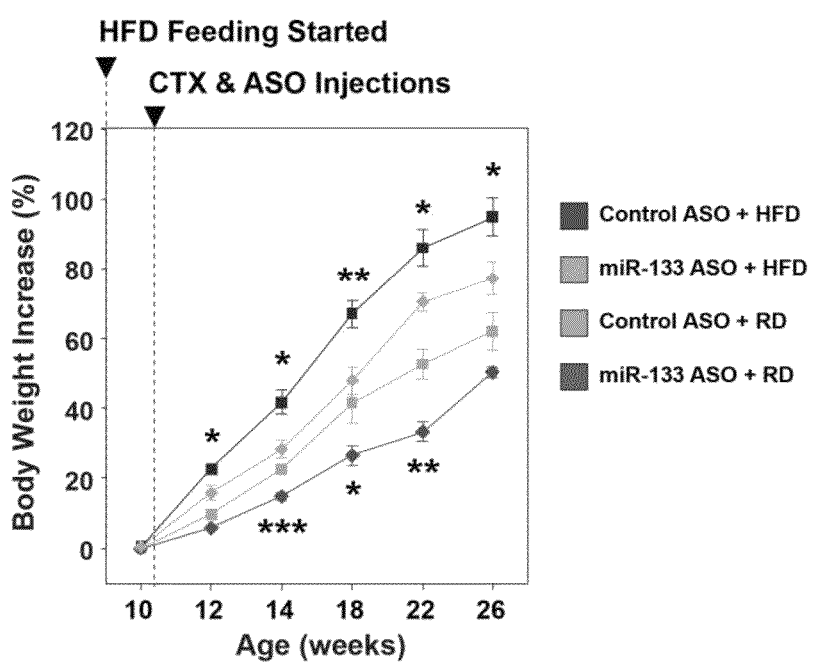
Fig 6 A and B

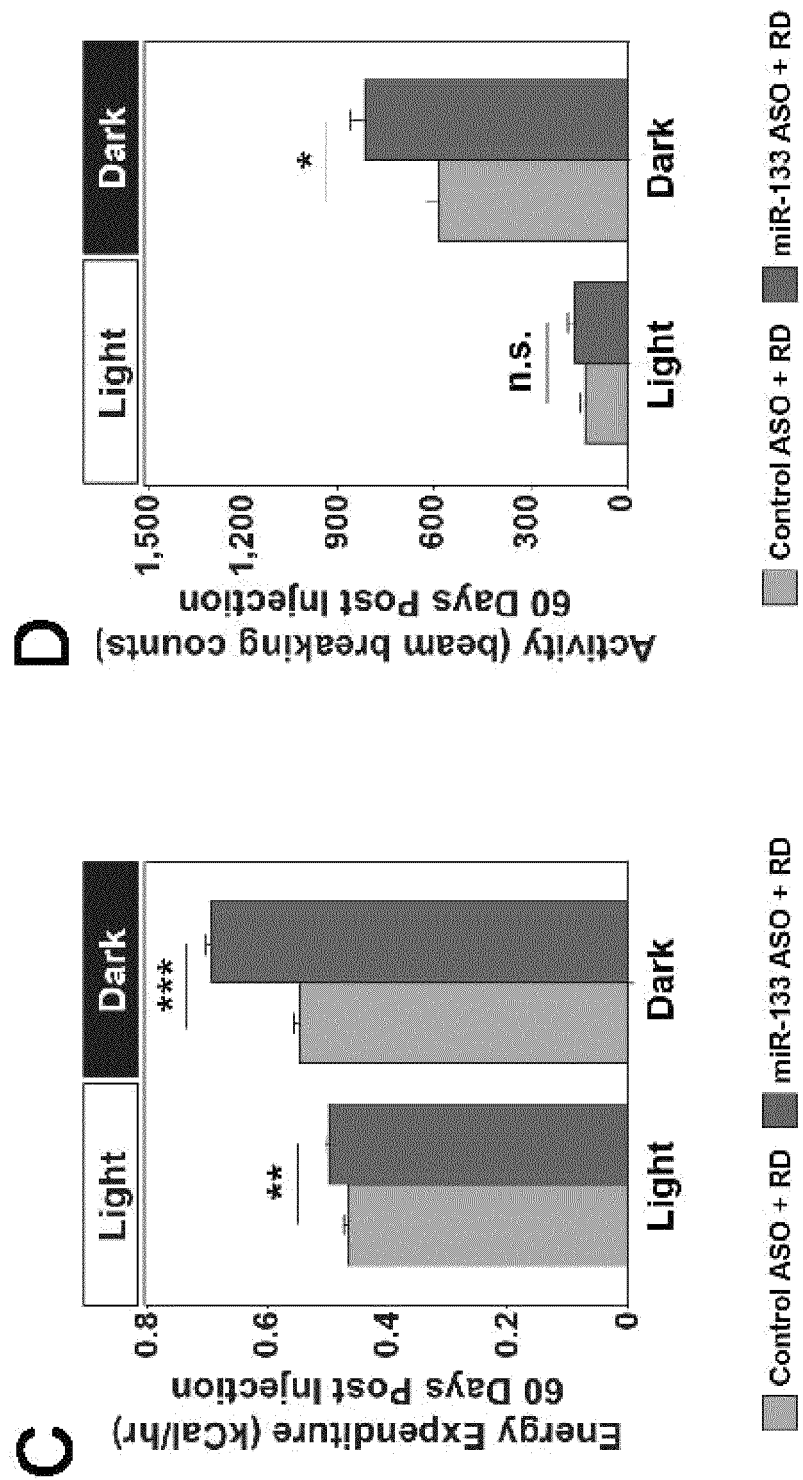
Figure 6C and D

SEQUENCE LISTING

```
<160> NUMBER OF SEQ ID NOS: 26

<210> SEQ ID NO 1
<211> LENGTH: 88
<212> TYPE: RNA
<213> ORGANISM: Homo sapiens

<400> SEQUENCE: 1
acaaugcuuu gcuagagcug guaaaaugga accaaaucgc cucuucaaug gauuuggucc      60
ccuucaacca gcuguagcua ugcauuga                                        88

<210> SEQ ID NO 2
<211> LENGTH: 92
<212> TYPE: RNA
<213> ORGANISM: Homo sapiens

<400> SEQUENCE: 2
gggagccaaa ugcuuugcua gagcugguaa aauggaacca aaucgacugu uggucccuu      60 caaccagcug uagcugugca uugauggcgc cg                                   92

<210> SEQ ID NO 3
<211> LENGTH: 119
<212> TYPE: RNA
<213> ORGANISM: Homo sapiens

<400> SEQUENCE: 3
ccucagaaga aagaugcccc cugcucuggc uggucaaacg gaaccaaguc cgucuuccug     60
agagguuugg uccccuucaa ccagcuacag cagggcuggc aaugcccagu ccuuggaga    119

<210> SEQ ID NO 4
<211> LENGTH: 22
<212> TYPE: RNA
<213> ORGANISM: Homo sapiens

<400> SEQUENCE: 4
uuuggucccc uucaaccagc ug                                              22

<210> SEQ ID NO 5
<211> LENGTH: 22
<212> TYPE: RNA
<213> ORGANISM: Homo sapiens

<400> SEQUENCE: 5
uuuggucccc uucaaccagc ua                                              22

<210> SEQ ID NO 6
<211> LENGTH: 23
<212> TYPE: RNA
<213> ORGANISM: Homo sapiens
```

```
<400> SEQUENCE: 6
auagcugguu gaaggggacc aaa                                           23

<210> SEQ ID NO 7
<211> LENGTH: 26
<212> TYPE: DNA
<213> ORGANISM: Homo sapiens

<400> SEQUENCE: 7
actcgagttc tctgcttgga tgggct                                        26

<210> SEQ ID NO 8
<211> LENGTH: 28
<212> TYPE: DNA
<213> ORGANISM: Homo sapiens

<400> SEQUENCE: 8
agcggccgcg acacaggggt atttggca                                      28

<210> SEQ ID NO 9
<211> LENGTH: 31
<212> TYPE: DNA
<213> ORGANISM: Homo sapiens

<400> SEQUENCE: 9
gcccccgtgt gataaggttg tgtgctgtgt g                                  31

<210> SEQ ID NO 10
<211> LENGTH: 51
<212> TYPE: DNA
<213> ORGANISM: Homo sapiens

<400> SEQUENCE: 10
cgttttcact acatacttat attaacatca tttcttcaga ataagttgtc c            51

<210> SEQ ID NO 11
<211> LENGTH: 29
<212> TYPE: DNA
<213> ORGANISM: Homo sapiens

<400> SEQUENCE: 11
agaattctga gctgcaagaa cagcagtgt                                     29

<210> SEQ ID NO 12
<211> LENGTH: 37
<212> TYPE: DNA
<213> ORGANISM: Homo sapiens

<400> SEQUENCE: 12
agcggccgct cccatcatgt ttttaggtga gttttg                             37

<210> SEQ ID NO 13
<211> LENGTH: 22
<212> TYPE: DNA
<213> ORGANISM: Homo sapiens

<400> SEQUENCE: 13
tagctggttg ccaggaccaa aa                                            22

<210> SEQ ID NO 14
```

```
<211> LENGTH: 22
<212> TYPE: DNA
<213> ORGANISM: Homo sapiens

<400> SEQUENCE: 14
tttcctcccc ttcaaccagc tg                                              22

<210> SEQ ID NO 15
<211> LENGTH: 21
<212> TYPE: DNA
<213> ORGANISM: Homo sapiens

<400> SEQUENCE: 15
gcatacgagc tcttccgatc t                                               21

<210> SEQ ID NO 16
<211> LENGTH: 20
<212> TYPE: RNA
<213> ORGANISM: Homo sapiens

<400> SEQUENCE: 16
gcugguugaa ggggaccaaa                                                 20

<210> SEQ ID NO 17
<211> LENGTH: 20
<212> TYPE: DNA
<213> ORGANISM: Homo sapiens

<400> SEQUENCE: 17
gctggttgaa ggggaccaaa                                                 20

<210> SEQ ID NO 18
<211> LENGTH: 22
<212> TYPE: RNA
<213> ORGANISM: Homo sapiens

<400> SEQUENCE: 18
uagcugguug aaggggacca aa                                              22

<210> SEQ ID NO 19
<211> LENGTH: 22
<212> TYPE: DNA
<213> ORGANISM: Homo sapiens

<400> SEQUENCE: 19
tagctggttg aaggggacca aa                                              22

<210> SEQ ID NO 20
<211> LENGTH: 22
<212> TYPE: RNA
<213> ORGANISM: Homo sapiens

<400> SEQUENCE: 20
cagcugguug aaggggacca aa                                              22

<210> SEQ ID NO 21
<211> LENGTH: 22
<212> TYPE: DNA
<213> ORGANISM: Homo sapiens

<400> SEQUENCE: 21
cagctggttg aaggggacca aa                                              22
```

```
<210> SEQ ID NO 22
<211> LENGTH: 45
<212> TYPE: RNA
<213> ORGANISM: Mus musculus

<400> SEQUENCE: 22
aaaugauguu aauauaagua uguagugaag gaccaaaccg uguga            45

<210> SEQ ID NO 23
<211> LENGTH: 46
<212> TYPE: RNA
<213> ORGANISM: Homo sapiens

<400> SEQUENCE: 23
aaauaauguu aauauaagua ucuggugaag gaccaaaacc guguga           46

<210> SEQ ID NO 24
<211> LENGTH: 46
<212> TYPE: RNA
<213> ORGANISM: Danio rerio

<400> SEQUENCE: 24
aaauaauguu aauauaagua ucuagugaag gaccaaaacu guguaa           46

<210> SEQ ID NO 25
<211> LENGTH: 46
<212> TYPE: RNA
<213> ORGANISM: Unknown
<220> FEATURE:
<223> OTHER INFORMATION: frog

<400> SEQUENCE: 25
aaauaauguu gauauuagaa aauagugaag gaccaaaacc gaguaa           46

<210> SEQ ID NO 26
<211> LENGTH: 45
<212> TYPE: RNA
<213> ORGANISM: Artificial Sequence
<220> FEATURE:
<223> OTHER INFORMATION: mutated 3' UTR

<400> SEQUENCE: 26
aaaugauguu aauauaagua uguagugaac cugguuuccg uguga            45
```

MICRORNA INHIBITORS

CROSS-REFERENCE TO RELATED APPLICATIONS

This application is a national phase application of PCT International Application No. PCT/CA2012/050636, filed Sep. 13, 2012, which claims the benefit of U.S. Provisional Application No. 61/534,107, filed on Sep. 13, 2011, the disclosures of which are incorporated by reference herein in their entireties.

INCORPORATION OF SEQUENCE LISTING

A computer readable form of the Sequence Listing "PAT_6926-W-2_Sequence_Listing.txt", submitted via EFS-WEB and created on Dec. 8, 2014, is herein incorporated by reference.

FIELD OF THE INVENTION

The present disclosure relates to a treatment for obesity and diseases associated with obesity, using microRNA inhibitors.

BACKGROUND OF THE INVENTION

According to a recent report by the World Health Organization, obesity has reached global epidemic proportions. In 2008, 1.5 billion adults world-wide were overweight, and of these, more than 500 million were clinically obese. Obesity, which is often caused by excessive intake of calories, also poses a major risk for type 2 diabetes, cancer, non-alcoholic fatty liver, and cardiovascular diseases.

Adipocytes are the primary components of fat tissue (Cypess et al., 2009). Two major types of fat tissue (adipocytes) exist—"white" adipose tissue (WAT) and "brown" adipose tissue (BAT). White adipocytes store chemical energy in form of triglycerides and release fatty acids as an energy source. In contrast, brown adipocytes break down fatty acids to generate body heat. An overabundance of white fat characterizes human obesity. Beige adipocytes, which are cells with intermediate phenotype between that of white and brown adipocytes, are also known (Ishibashi and Seale, 2011). Beige cells have low basal expression of UCP1 (like white adipocytes) but respond to cyclic AMP stimulation with high UCP1 expression and respiration rates (like brown adipocytes). Beige adipocytes origins are thought to be from precursor cells within white fat (Wu et al. 2012).

Functional brown adipocytes were thought, until recently, to exist only in human newborn babies, young children, certain disease states, and small mammals. Recent studies have shown that a limited number of brown or beige adipocytes are also present and functional in human adults (Cypess et al., 2009, van Marken Lichtenbelt et al., 2009; Wu et al 2012, and Virtanen et al., 2009). An intriguing observation from these studies is that thinner people have more brown adipocytes than overweight or obese people (Cypess et al., 2009). This correlation supports a long-held hypothesis that obesity might be caused by the loss of functional brown adipocytes (Himms-Hagen, 1979). Indeed, experimental increases in BAT in animals are associated with a lean and healthy phenotype (Kopecky J. et al. 1995; Himms-Hagen et al. 1994).

Mature skeletal muscle contains "satellite cells" which are adult stem cells (Charge and Rudnicki, 2004). Satellite cells undergo self-renewal and participate in the differentiation process to both repair and create new muscle fibers.

Two recent studies revealed that skeletal muscle cells and brown adipocytes, but not white adipocytes, are unexpectedly derived from the same regions of the embryonic somites (dermomyotome) (Seale et al., 2008; Lepper and Fan, 2010). Brown adipocytes and skeletal muscle cells also share common features such as high mitochondrial content and energy-expensing nature of metabolic type (Farmer, 2008). Importantly, it has been shown that cultured satellite cells can be transformed into functional brown adipocytes by overexpressing brown adipocyte-enriched transcription factors, such as Prdm16 (Seale et al. (2008), and Kajimura et al., 2009). Thus, PR domain containing 16 (Prdm16), a zinc finger transcription factor, activates the brown adipogenic program while repressing the myogenic program. Conversely, reduced expression of Prdm16 drives brown preadipocytes to undergo myogenic differentiation.

MicroRNAs (miRNAs or miRs) are conserved non-coding small RNAs, which regulate gene expression (D. P. Bartel, MicroRNAs: genomics, biogenesis, mechanism, and function. Cell 116, 281 (Jan. 23, 2004)). MicroRNAs bind to the 3' untranslated regions (3'UTRs) of target mRNAs to reduce their translation and stability. More than one-third of protein-encoding mRNAs in mammalian transcriptomes are predicted to be directly regulated by microRNAs.

The epidemic of obesity demands new therapeutic options.

SUMMARY OF THE INVENTION

Applicants have discovered that myogenic lineage commitment of satellite cells is regulated by specific microRNAs, such as miR-133, which are abundant in satellite cells and their myogenic progeny. In one aspect, Applicants have demonstrated that these microRNAs repress the expression of key determinants of brown adipogenesis, thus preventing the adipogenic differentiation of satellite cells. In one particular embodiment, the brown adipose determination of satellite cells is controlled by myogenic microRNAs, such as miR-133, that can directly target the 3'UTR of a brown adipocyte-enriched transcription factor mRNA, such as Prdm16 mRNA, to repress expression of said transcription factor.

Thus, in a primary aspect, the present application provides an identification of specific miRNAs as targets for use in the treatment of obesity and/or diseases associated with obesity. Such targets were unknown prior to Applicant's invention.

In one aspect, the invention provides an miRNA-133 inhibitor for use in the treatment or prevention of obesity or a disease or disorder associated therewith.

In one aspect, the inhibitor is a nucleic acid.

In one aspect, the miRNA-133 inhibitor is capable of hybridizing to one or more mature miRNAs selected from miRNA-133a and miRNA-133b, preferably human (hsa) miRNA-133a and miRNA-133b.

In one aspect, the inhibitor has at least 85%, 90%, 91%, or 95% sequence identity to a complement of the mature miRNA.

In one aspect, the inhibitor is complementary to at least 10, 15, 17, 18, 19, 20, 21, or 22 contiguous nucleotides of the mature miRNA-133a or miRNA-133b.

In one aspect, the inhibitor hybridizes to the mature miRNA under standard hybridization conditions.

In one aspect, the inhibitor is complementary to the mature miRNA along the entire length of the mature miRNA.

In one aspect, the inhibitor comprises the sequence 5'-GCUGGUUGAAGGGGACCAAA-3' (SEQ ID NO:16) or 5'-GCTGGTTGAAGGGGACCAAA-3' (SEQ ID NO:17).

In one aspect, the inhibitor comprises the sequence
5'-UAGCUGGUUGAAGGGGACCAAA-3' (SEQ ID NO:18)
5'-TAGCTGGTTGAAGGGGACCAAA-3' (SEQ ID NO:19)
5'-CAGCUGGUUGAAGGGGACCAAA-3' (SEQ ID NO:20), or
5'-CAGCTGGTTGAAGGGGACCAAA-3' (SEQ ID NO:21).

In one aspect, the inhibitor comprises at least one modified nucleotide.

In one aspect, inhibitor is an antagomiR. In one aspect, the inhibitor comprises the sequence:
5'*mA*mUmAmGmCmUmGmGmUmUmGmAmAmGm-GmGmGmAmC*mC*mA*mA*mAChl3'
wherein
m represents a 2'-O-methyl-modified nucleotide,
* represents a phosphorothioate linkage, and
Chl represents a 3' cholesterol moiety.

In one aspect, the inhibitor is a peptide nucleic acid (PNA).
In one aspect, inhibitor is a locked-in nucleic acid.
In one aspect, the disease or disorder associated with obesity is type 2 diabetes.

In one aspect, the present invention provides a method for treating or preventing obesity or a disease associated therewith comprising administering to a patient an miRNA-133 inhibitor as defined herein.

In one aspect, the present invention provides a method for increasing the expression of Prdm16, comprising contacting cells which are capable of expressing Prdm16 with the miRNA inhibitor as defined herein. In one aspect, the cells capable of expressing Prdm16 are myogenic cells, satellite cells, myoblasts, brown adipocyte progenitor cells, fibrogenic/adipogenic progenitors isolated from skeletal muscles, or brown pre-adipocytes.

In one aspect, the present invention provides a method for inducing energy-expending adipocytes comprising contacting cells with the miRNA inhibitor as defined herein.

In one aspect, the present invention provides an assay method to screen for drug candidates for the treatment or prevention of obesity or a disease associated therewith, said method comprising: a) contacting a compound with an miRNA-133 biosensor as defined herein, and b) assessing the expression of a reporter gene; wherein a difference in the expression of said reporter gene in comparison to the expression of said reporter gene in the absence of the compound qualifies the compound as a drug candidate for the treatment or prevention of obesity or a disease associated therewith. In one aspect, the reporter gene codes for a bioluminescent or fluorescent protein. In one aspect, the difference in expression of the reporter gene is a decrease in expression of the reporter gene. In one aspect, the difference in expression of the reporter gene is an increase in expression of the reporter gene.

In one aspect, the invention provides an inhibitor as described herein that qualifies as a drug candidate for the treatment or prevention of obesity or a disease associated therewith as described herein.

In one aspect, the present invention provides a biosensor for use in the assay described herein, wherein said biosensor comprises: i) a sequence complementary to at least 6 contiguous nucleotides of miRNA-133a (5'-uuuggucccuucaac-cagcug-3') or complementary to at least 6 contiguous nucleotides of microRNA-133b (5'-uuuggucccuucaaccagcua-3'), and ii) a reporter gene. The sequence may be complementary to at least 10, 12, 14, 15, 16, 17, 18, 19, 20, 21, or 22 contiguous nucleotides of said microRNAs.

BRIEF DESCRIPTION OF THE DRAWINGS

Other aspects and features of the present disclosure will become apparent to those ordinarily skilled in the art upon review of the following description of specific embodiments in conjunction with the accompanying figures.

DETAILED DESCRIPTION

Figure 1A:
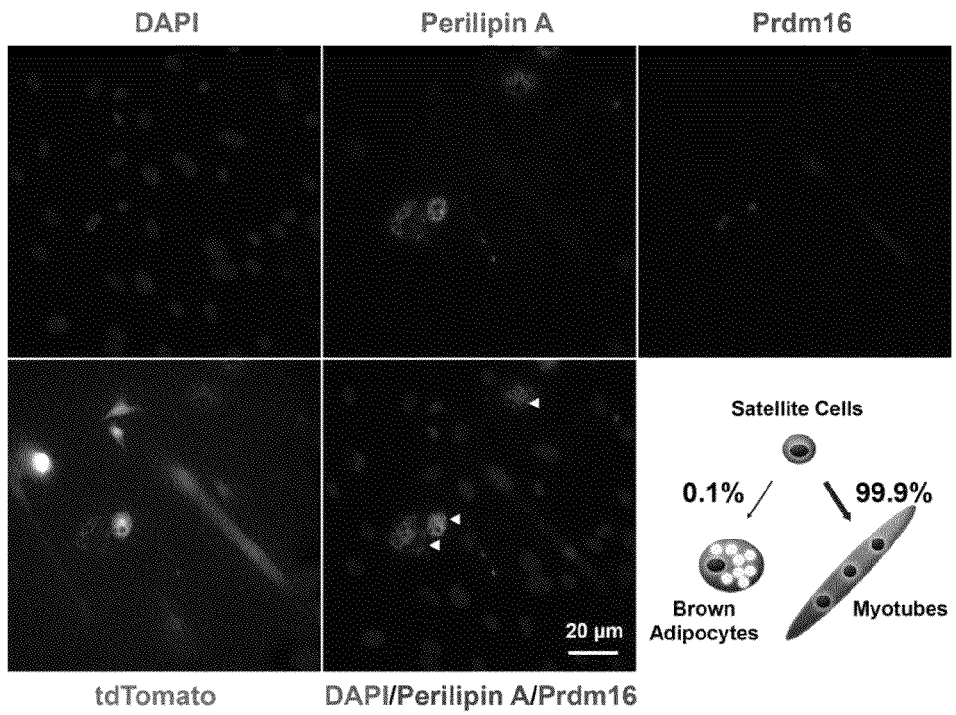
FIG. 1 shows that Satellite Cells Differentiate Into Brown Adipocytes. (A) Satellite cells differentiated into brown adipocytes (arrowheads) in myofiber cultures under pro-adipogenic conditions. Myofibers (n>600) with resident satellite cells were isolated from Pax7-CreER/R26R-tdTomato EDL muscles and cultured for 12 days in pro-adipogenic medium. Lineage marked satellite cell-derived brown adipocytes expressed tdTomato and Prdm16, Perilipin A. (B) Clonal analysis of FACS-isolated single satellite stem cells and satellite myogenic progenitors (n>2,000 for each cell type) indicates some satellite cells are bipotential. Approximately 1.6% of satellite stem cells and 3.3% satellite myogenic progenitors gave rise to mixed muscle and adipocyte containing colonies. In addition, 6.5% of satellite stem cells clones but none of satellite myogenic progenitors gave rise to colonies uniformly composed of adipocytes. Shown are representative images of three types of clones derived from clonal satellite cell cultures stained with Oil Red O, and the corresponding percentages from satellite stem cells (Myf5$^-$) and satellite myogenic progenitors (Myf5$^+$) clones.

Applicants have discovered that myogenic lineage commitment of satellite cells is regulated by specific microRNAs, such as miR-133, which are abundant in satellite cells and their myogenic progeny. In one aspect, Applicants have demonstrated that these microRNAs repress the expression of key determinants of brown adipogenesis thus preventing the adipogenic differentiation of satellite cells. More particularly, the brown adipose determination of satellite cells is controlled by myogenic microRNAs, such as miR-133, that can directly target the 3'UTR of a brown adipocyte-enriched transcription factor mRNA, such as Prdm16 mRNA, to repress expression of said transcription factor.

In one aspect, the present invention is thus based on the discovery that agents that inhibit the expression and/or activity of the miRNA (including miR-133a and 133b) disclosed herein are able to result in the induction of brown adipose tissue (BAT) within muscle for the prevention and/or treatment of obesity. Use of miR-133 inhibitors suppresses the inhibitory effects of the miRNAs on Prdm16 expression in myogenic cells. The present invention therefore provides an identification of miRNAs that are involved in inhibiting brown fat differentiation, methods for inhibiting the activity or expression of the miRNA using miRNA inhibitors, and uses of these inhibitors in the prevention and/or treatment of obesity and diseases that are associated with obesity, such as type II diabetes.

The present invention is based in part on the discovery by the applicants of the roles of microRNAs in the skeletal muscle/brown fat lineage switch and the use of their knowledge to explore an alternative approach to treat obesity and related diseases—reducing white adipose tissue by increasing energy expenditure through the induction of brown and beige adipose tissue. Brown and beige adipocytes can collectively be referred to as energy-expending adipocytes.

In one aspect, the present invention is thus based on the discovery that miR-133 inhibitors leads to increased differentiation in energy-expending adipocyte of not only satellite cells but also of other myogenic progenitors, brown preadipocytes and fibrogenic/adipogenic progenitors found in skeletal muscle.

In the following detailed description section, the specific embodiments of the present invention are described in connection with preferred embodiments. However, to the extent that the following description is specific to a particular embodiment or a particular use of the present invention, this is intended to be for exemplary purposes only and simply provides a description of the exemplary embodiments. Accordingly, the invention is not limited to the specific embodiments described below, but rather, it includes all alternatives, modifications, and equivalents falling within the scope of the appended claims.

DEFINITIONS

Unless otherwise explained, all technical and scientific terms used herein have the same meaning as commonly understood by one of ordinary skill in the art to which this disclosure belongs. The singular terms "a", "an", and "the" include plural referents unless the context clearly indicates otherwise. Similarly, the word "or" is intended to include "and" unless the context clearly indicates otherwise. The term "includes" means "comprises".

In accordance with the present invention there may be employed conventional molecular biology, microbiology, and recombinant DNA techniques within the skill of the art. Such techniques are explained fully in the literature. See, e.g., Sambrook et al, "Molecular Cloning: A Laboratory Manual" (1989); "Current Protocols in Molecular Biology" Volumes I-III [Ausubel, R. M., ed. (1994)]; "Cell Biology: A Laboratory Handbook" Volumes I-III [J. E. Celis, ed. (1994))]; "Current Protocols in Immunology" Volumes I-III [Coligan, J. E., ed. (1994)]; "Oligonucleotide Synthesis" (M. J. Gait ed. 1984); "Nucleic Acid Hybridization" [B. D. Hames & S. J. Higgins eds. (1985)]; "Transcription And Translation" [B. D. Hames & S. J. Higgins, eds. (1984)]; "Animal Cell Culture" [R. I. Freshney, ed. (1986)]; "Immobilized Cells And Enzymes" [IRL Press, (1986)]; B. Perbal, "A Practical Guide To Molecular Cloning" (1984).

As used herein, "hybridization", "hybridizes" or "capable of hybridizing" is understood to mean the forming of a double or triple stranded molecule or a molecule with partial double or triple stranded nature. The term "anneal" as used herein is synonymous with "hybridize." The term "hybridization", "hybridize(s)" or "capable of hybridizing" encompasses the terms "stringent condition(s)" or "high stringency" and the terms "low stringency" or "low stringency condition(s)."

The miRNA inhibitor oligonucleotides, in one aspect, will hybridize to miRNA-133 at 37° C. under physiological conditions mimicking cellular environments. The term "standard hybridization conditions" refers to laboratory experimental conditions for which salt and temperature conditions are substantially equivalent to 5×SSC and 65° C. for both hybridization and wash. However, one skilled in the art will appreciate that such "standard hybridization conditions" are dependent on particular conditions including the concentration of sodium and magnesium in the buffer, nucleotide sequence length and concentration, percent mismatch, percent formamide, presence of modified nucleotides and/or backbones, and the like. Also important in the determination of "standard hybridization conditions" is whether the two sequences hybridizing are RNA-RNA, DNA-DNA or RNA-DNA, or synthetic polynucleotides (containing modified bases or backbone). Such standard hybridization conditions are easily determined by one skilled in the art according to well-known formulae, wherein hybridization is typically 10-20° C. below the predicted or determined $T_n$, with washes of higher stringency, if desired.

The terms nucleic acid, oligonucleotide, and polynucleotide are used interchangeably in this application. In the context of this invention, the term "oligonucleotide" refers to an oligomer or polymer of nucleotide or nucleoside monomers consisting of naturally occurring bases, sugars and inter-sugar (backbone) linkages, and includes single-stranded and double-stranded DNA and RNA. The term "oligonucleotide" also includes oligomers comprising non-naturally occurring monomers, or portions thereof, which function similarly. The term "oligonucleotide" also includes oligmers or polymers comprising non-natural backbone linkages. The term "oligonucleotide" also includes oligomers or polymers comprising substitutents or tags. It is not necessary for all positions in a given compound to be uniformly modified, and in fact more than one of the aforementioned modifications may be incorporated in a single compound or even at a single nucleoside within an oligonucleotide. Such modified or substituted oligonucleotides may be chosen over native forms because of properties such as, for example, enhanced cellular uptake and increased stability in the presence of nucleases.

The phrase "pharmaceutically acceptable" refers to molecular entities and compositions that are physiologically tolerable.

The term 'carrier' means a non-toxic material used in the formulation of pharmaceutical compositions to provide a medium, bulk and/or useable form to a pharmaceutical composition. A carrier may comprise one or more of such materials such as an excipient, stabilizer, or an aqueous pH buffered solution. Examples of physiologically acceptable carriers include aqueous or solid buffer ingredients including phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN®, polyethylene glycol (PEG), and PLURONICS®.

The term "energy expending adipocyte" collectively refers to brown and beige adipocytes, more particularly it refers to thermogenic cells having increased mitochondria respiration rates.

The term 'obesity' is a term well-known in the art. Obesity is a medical condition in which excess body fat has accumulated to the extent that it may have an adverse effect on health, leading to reduced life expectancy and/or increased health problems. People are considered as obese when their body mass index (BMI), a measurement obtained by dividing a person's weight in kilograms by the square of the person's height in meters, exceeds 30 kg/m².

Diseases and disorders associated with (or related to) obesity include cardiovascular disease, obstructive sleep apnea, certain types of cancer, non-alcoholic fatty liver, osteoarthritis, and asthma, and in particular type 2 diabetes.

miRNAs

MicroRNA molecules ("miRNAs" or "miRs") are short ribonucleic acid (RNA) molecules having a typical length of approximately 21 to 22 nucleotides, though lengths of 17 and up to 25 nucleotides have been reported. The miRNAs are each processed from a longer precursor RNA molecule ("precursor miRNA"). Precursor miRNAs are transcribed from non-protein-encoding genes. The precursor miRNAs have two regions of complementarity that enables them to form a stem-loop- or fold-back-like structure, which is cleaved by an enzyme called Dicer in animals Dicer is ribonuclease III-like nuclease. The processed miRNA is typically a portion of the stem (see review of Carrington et al. (Science, 301 (5631): 336-338, 2003).

The processed miRNA (also referred to as "mature miRNA") can function as post-trascriptional regulators that bind to complementary sequences on target messenger RNA transcripts (mRNAs), usually resulting in translational repression or target degradation and gene silencing. Examples of animal miRNAs include those that imperfectly basepair with the target, which halts translation. In eukaryotes, miRNA complementarity typically encompasses the 5' bases 2-7 of the microRNA, the microRNA seed region.

The term "miRNA" is used herein according to its ordinary and plain meaning. As used herein, the term "miRNA" refers to RNA, typically single-stranded RNA, of about 10-50 nucleotides in length, possibly between about 15-25 nucleotides in length, e.g., about 20-24 or 21-23 nucleotides in length. The terms "miRNAs", "miRs", "microRNAs", and any variants not specifically listed, may be used herein interchangeably, and as used throughout the present application and claims. Also, the terms "miRNAs", "miRs", and "microRNAs" are intended to include within their scope nucleic acids specifically recited herein as well as all substantially homologous analogs and allelic variations.

microRNA-133 is a microRNA that was first experimentally characterized in mice, and homologues have since been discovered in several other species, such as humans, and including invertebrates, such as the fruit fly *Drosophila melanogaster*. Each species often encodes multiple microRNAs with identical or similar mature sequence. For example, in the human genome there are three known miR-133 genes: miR-133a-1, miR-133a-2 and miR-133b found on chromosomes 18, 20 and 6 respectively. The mature sequences (hsa-miR-133a and hsa-miR-133b) are excised from the miR-133 precursors in the 3' arm of the hairpin.

Precursor miRNA-133s

Shown below are the sequences for the three human miRNA-133 precursors, also found in U.S. Pat. No. 7,960,359, incorporated by reference herein:

```
MiR-133a-1 (RNA, Homo sapiens)
                                         SEQ ID NO: 1
ACAAUGCUUU GCUAGAGCUG GUAAAAUGGA ACCAAAUCGC

CUCUUCAAUG GAUUUGGUCC CCUUCAACCA GCUGUAGCUA

UGCAUUGA (88)

MiR-133a-2 (RNA, Homo sapiens)
                                         SEQ ID NO: 2
GGGAGCCAAA UGCUUUGCUA GAGCUGGUAA AAUGGAACCA

AAUCGACUGU UGGUCCCCUU CAACCAGCUG UAGCUGUGCA

UUGAUGGCGC CG (92)

MiR-133b (RNA, Homo sapiens)
                                         SEQ ID NO: 3
CCUCAGAAGA AAGAUGCCCC CUGCUCUGGC UGGUCAAACG

GAACCAAGUC CGUCUUCCUG AGAGGUUUGG UCCCCUUCAA

CCAGCUACAG CAGGGCUGGC AAUGCCCAGU CCUUGGAGA (119)
```

Processed/Mature miRNA Sequences:

After transcription and processing, there are only two forms of processed/mature miRNA-133, namely miR-133a and miR-133b, with sequences shown below:

TABLE 1

| miR-133a | 5'-UUUGGUCCCCUUCAACCAGCUG-3' | SEQ ID NO: 4 |
|---|---|---|
| miR-133b | 5'-UUUGGUCCCCUUCAACCAGCUA-3' | SEQ ID NO: 5 |

It may be noted that the only difference between these two miR-133 isoforms is the last nucleotide (a "G" in miR-133a and an "A" in miR-133b).

miRNA Inhibitors

The term "miRNA inhibitor" as used herein, refers to an agent that reduces or inhibits the expression, stability, sub-cellular localization, or activity of a miRNA. A miRNA inhibitor may function, for example, by blocking the activity of a miRNA (e.g., blocking the ability of an miRNA to function as a translational repressor of one or more miRNA targets), or by mediating miRNA degradation. More specifically, with regard to miRNA-133, an miRNA-133 inhibitor may 1) reduce the overall cellular expression level of miR-133a and/or miR-133b, 2) reduce the stability of miR-133a and/or miR-133b or increase their turnover rates, 3) reduce the presence of miR-133a and/or miR-133b in Argonaute complexes, 4) modify or hybridize to the sequences of miR-133a and/or miR-133b, thus blocking or reducing the efficiency of the hybridization of miR-133a/b to their mRNA targets, 5) modify or hybridize to miR-133a and/or miR-133b targeting sites on mRNA targets, thus blocking or reducing the efficiency of the hybridization of miR-133a/b to their mRNA targets.

In one aspect, said miRNA inhibitor is a protein or small molecule.

In one aspect, an "miRNA inhibitor" is a polynucleotide (also referred to as an oligonucleotide) having a sequence that is antisense, either complementary or partially complementary as described herein, to a mature single-stranded miRNA or portion thereof.

In one aspect, the invention relates to an isolated single stranded polynucleotide for use as an miRNA inhibitor. The molecule preferably comprises a minimum number of ten moieties, preferably a minimum of thirteen, more preferably a minimum of fifteen, even more preferably a minimum of 18, and most preferably a minimum of 21 moieties.

The miRNA inhibitor comprises a maximum number of fifty moieties, preferably a maximum of forty, more preferably a maximum of thirty, even more preferably a maximum of twenty-five, and most preferably a maximum of twenty-three moieties. A suitable range of minimum and maximum number of moieties may be obtained by combining any of the above minima with any of the above maxima.

Each moiety comprises a base bonded to a backbone unit. In this specification, a base refers to any one of the nucleic acid bases present in DNA or RNA. The base can be a purine or pyrimidine. Examples of purine bases include adenine (A) and guanine (G). Examples of pyrimidine bases include thymine (T), cytosine (C) and uracil (U).

The backbone unit may be any molecular unit that is able stably to bind to a base and to form an oligomeric chain. Suitable backbone units are well known to those in the art. For example, suitable backbone units include sugar-phosphate groups, such as the sugar-phosphate groups present in ribonucleotides, deoxyribonucleotides, phosphorothioate deoxyribose groups, N'3-N'S phosphoroamidate deoxyribose groups, 2'O-alkyl-ribose phosphate groups, 2'-O-alkyl-alkoxy ribose phosphate groups, ribose phosphate group containing a methylene bridge, 2'-Fluororibose phosphate groups, morpholino phosphoroamidate groups, cyclohexene groups, tricyclo phosphate groups, and amino acid molecules.

In one embodiment, the miRNA inhibitor comprises at least one moiety which is a ribonucleotide moiety or a deoxyribonucleotide moiety.

In another embodiment, the miRNA inhibitor comprises at least one moiety which confers increased nuclease resistance. The nuclease can be an exonuclease, an endonuclease, or both. The exonuclease can be a 3'→5' exonuclease or a 5'→3' exonuclease. Examples of 3'→5' human exonuclease include PNPT1, Werner syndrome helicase, RRP40, RRP41, RRP42, RRP45, and RRP46. Examples of 5'→3' exonuclease include XRN2, and FEN1. Examples of endonucleases include Dicer, Drosha, RNase4, Ribonuclease P, Ribonuclease H1, DHP1, ERCC-1 and OGG1. Examples of nucleases which function as both an exonuclease and an endonuclease include APE1 and EXO1.

An miRNA inhibitor comprising at least one moiety which confers increased nuclease resistance means a sequence of moieties wherein at least one moiety is not recognized by a nuclease. Therefore, the nuclease resistance of the molecule is increased compared to a sequence containing only unmodified ribonucleotide, unmodified deoxyribonucleotide or both. Such modified moieties are well known in the art, and were reviewed, for example, by Kurreck, Eur. J. Biochem. 270, 1628-1644 (2003).

A modified moiety can occur at any position in the miRNA inhibitor. For example, to protect the miRNA inhibitor against 3'→5' exonucleases, the molecule can have at least one modified moiety at the 3' end of the molecule and preferably at least two modified moieties at the 3' end. If it is desirable to protect the molecule against 5'→3' exonuclease, the miRNA inhibitor can have at least one modified moiety and preferably at least two modified moieties at the 5' end of the molecule. The miRNA inhibitor can also have at least one and preferably at least two modified moieties between the 5' and 3' end of the molecule to increase resistance of the molecule to endonucleases. In one embodiment, all of the moieties are nuclease resistant.

In another embodiment, the miRNA inhibitor comprises at least one modified deoxyribonucleotide moiety. Suitable modified deoxyribonucleotide moieties are known in the art.

A suitable example of a modified deoxyribonucleotide moiety is a phosphorothioate deoxyribonucleotide moiety. An miRNA inhibitor comprising more than one phosphorothioate deoxyribonucleotide moiety is referred to as phosphorothioate (PS) DNA. See, for example, Eckstein, Antisense Nucleic Acids Drug Dev. 10, 117-121 (2000).

Another suitable example of a modified deoxyribonucleotide moiety is an N'3-N'5 phosphoroamidate deoxyribonucleotide moiety. An oligonucleotide molecule comprising more than one phosphoroamidate deoxyribonucleotide moiety is referred to as phosphoroamidate (NP) DNA. See, for example, Gryaznov et al., J. Am. Chem. Soc. 116, 3143-3144 (1994).

In another embodiment, the molecule comprises at least one modified ribonucleotide moiety. Suitable modified ribonucleotide moieties are known in the art.

A suitable example of a modified ribonucleotide moiety is a ribonucleotide moiety that is substituted at the 2' position. The substituents at the 2' position may, for example, be a $C_1$ to $C_4$ alkyl group. The $C_1$ to $C_4$ alkyl group may be saturated or unsaturated, and unbranched or branched. Some examples of $C_1$ to $C_4$ alkyl groups include ethyl, isopropyl, and allyl. The preferred $C_1$ to $C_4$ alkyl group is methyl. An oligoribonucleotide molecule comprising more than one ribonucleotide moiety that is substituted at the 2' position with a $C_1$ to $C_4$ alkyl group is referred to as a 2'-O—($C_1$-$C_4$ alkyl) RNA, e.g., 2'-O-methyl RNA (OMe RNA).

Another suitable example of a substituent at the 2' position of a modified ribonucleotide moiety is a $C_1$ to $C_4$ alkoxy-$C_1$ to $C_4$ alkyl group. The $C_1$ to $C_4$ alkoxy(alkyloxy) and $C_1$ to $C_4$ alkyl group may comprise any of the alkyl groups described above. The preferred $C_1$ to $C_4$ alkoxy-$C_1$ to $C_4$ alkyl group is methoxyethyl. An oligonucleotide molecule comprising more than one ribonucleotide moiety that is substituted at the 2' position with a $C_1$ to $C_4$ alkoxy-$C_1$ to $C_4$ alkyl group is referred to as a 2'-O—($C_1$ to $C_4$ alkoxy-$C_1$ to $C_4$ alkyl) RNA, e.g., 2'-O-methoxyethyl RNA (MOE RNA).

Another suitable example of a modified ribonucleotide moiety is a ribonucleotide that has a methylene bridge between the 2'-oxygen atom and the 4'-carbon atom. An oligoribonucleotide molecule comprising more than one ribonucleotide moiety that has a methylene bridge between the 2'-oxygen atom and the 4'-carbon atom is referred to as locked nucleic acid (LNA). See, for example, Kurreck et al., Nucleic Acids Res. 30, 1911-1918 (2002); Elayadi et al., Curr. Opinion Invest. Drugs 2, 558-561 (2001); Drum et al., Curr. Opinion Mol. Ther. 3, 239-243 (2001); Koshkin et al., Tetrahedron 54, 3607-3630 (1998); Obika et al., Tetrahedron Lett. 39, 5401-5404 (1998). Locked nucleic acids are commercially available from Proligo (Paris, France and Boulder, Colo., USA).

Another suitable example of a modified ribonucleotide moiety is a ribonucleotide that is substituted at the 2' position with fluoro group. A modified ribonucleotide moiety having a fluoro group at the 2' position is a 2'-fluororibonucleotide moiety. Such moieties are known in the art. Molecules comprising more than one 2'-fluororibonucleotide moiety are referred to herein as 2'-fluororibo nucleic acids (FANA). See, for example Damha et al., J. Am. Chem. Soc. 120, 12976-12977 (1998).

In another embodiment, the miRNA inhibitor comprises at least one base bonded to an amino acid residue. Moieties that have at least one base bonded to an amino acid residue will be referred to herein as peptide nucleic acid (PNA) moieties. Such moieties are nuclease resistance, and are known in the art. Molecules having more than one PNA moiety are referred to as peptide nucleic acids. Nielson, Methods Enzymol. 313, 156-164 (1999); Elayadi, et al, id.; Braasch et al., Biochemistry 41, 4503-4509 (2002), Nielsen et al., Science 254, 1497-1500 (1991).

The amino acids can be any amino acid, including natural or non-natural amino acids. Naturally occurring amino acids include, for example, the twenty most common amino acids normally found in proteins, i.e., alanine (Ala), arginine (Arg), asparagine (Asn), aspartic acid (Asp), cysteine (Cys), glutamine (Glu), glutamic acid (Glu), glycine (Gly), histidine (His), isoleucine (Ileu), leucine (Leu), lysine (Lys), methionine (Met), phenylalanine (Phe), proline (Pro), serine (Ser), threonine (Thr), tryptophan, (Trp), tyrosine (Tyr), and valine (Val).

The non-natural amino acids may, for example, comprise alkyl, aryl, or alkylaryl groups. Some examples of alkyl amino acids include α-aminobutyric acid, β-aminobutyric acid, γ-aminobutyric acid, δ-aminovaleric acid, and ε-aminocaproic acid. Some examples of aryl amino acids include ortho-, meta, and para-aminobenzoic acid. Some examples of alkylaryl amino acids include ortho-, meta-, and para-aminophenylacetic acid, and γ-phenyl-β-aminobutyric acid. Non-naturally occurring amino acids also include derivatives of naturally occurring amino acids. The derivative of a naturally occurring amino acid may, for example, include the addition or one or more chemical groups to the naturally occurring amino acid.

For example, one or more chemical groups can be added to one or more of the 2', 3', 4', 5', or 6' position of the aromatic ring of a phenylalanine or tyrosine residue, or the 4', 5', 6', or 7' position of the benzo ring of a tryptophan residue. The group can be any chemical group that can be added to an aromatic ring. Some examples of such groups include hydroxyl, $C_1$-$C_4$ alkoxy, amino, methylamino, dimethylamino, nitro, halo (i.e., fluoro, chloro, bromo, or iodo), or branched or unbranched $C_1$-$C_4$ alkyl, such as methyl, ethyl, n-propyl, isopropyl, butyl, isobutyl, or t-butyl.

Furthermore, other examples of non-naturally occurring amino acids which are derivatives of naturally occurring amino acids include norvaline (Nva), norleucine (Nle), and hydroxyproline (Hyp).

The amino acids can be identical or different from one another. Bases are attached to the amino acid unit by molecular linkages. Examples of linkages are methylene carbonyl, ethylene carbonyl and ethyl linkages. (Nielsen et al., *Peptide Nucleic Acids-Protocols and Applications*, Horizon Scientific Press, pages 1-19; Nielsen et al., *Science* 254: 1497-1500.)

One example of a PNA moiety is N-(2-aminoethyl)-glycine. Further examples of PNA moieties include cyclohexyl PNA, retro-inverso, phosphone, propionyl and aminoproline PNA.

PNA can be chemically synthesized by methods known in the art, e.g. by modified Fmoc or tBoc peptide synthesis protocols. The PNA has many desirable properties, including high melting temperatures (Tm), high base-pairing specificity with nucleic acid and an uncharged molecular backbone. Additionally, the PNA does not confer RNase H sensitivity on the target RNA, and generally has good metabolic stability. Peptide nucleic acids are also commercially available from Applied Biosystems (Foster City, Calif., USA).

In another embodiment, the miRNA inhibitor comprises at least one morpholino phosphoroamidate nucleotide moiety. A morpholino phosphoroamidate nucleotide moiety is a modified moiety which is nuclease resistant. Such moieties are known in the art. Molecules comprising more than one morpholino phosphoroamidate nucleotide moiety are referred to as morpholino (MF) nucleic acids. Heasman, Dev. Biol. 243, 209-214 (2002). Morpholono oligonucleotides are commercially available from Gene Tools LLC (Corvallis, Oreg., USA).

In another embodiment, the miRNA inhibitor comprises at least one cyclohexene nucleotide moiety. A cyclohexene nucleotide moiety is a modified moiety which is nuclease resistant. Such moieties are known in the art. Molecules comprising more than one cyclohexene nucleotide moiety are referred to as cyclohexene nucleic acids (CeNA). Wang et al., J. Am. Chem. Soc. 122, 8595-8602 (2000), Verbeure et al., Nucleic Acids Res. 29, 4941-4947 (2001).

In another embodiment, the miRNA inhibitor comprises at least one tricyclo nucleotide moiety. A tricyclo nucleotide moiety is a modified moiety which is nuclease resistant. Such moieties are known in the art. Steffens et al., J. Am. Chem. Soc. 119, 11548-11549 (1997), Renneberg et al., J. Am. Chem. Soc. 124, 5993-6002 (2002). Molecules comprising more than one tricyclo nucleotide moiety are referred to as tricyclo nucleic acids (tcDNA).

In another embodiment, to increase nuclease resistance of the miRNA inhibitors of the present invention to exonucleases, inverted nucleotide caps can be attached to the 5' end, the 3' end, or both ends of the molecule. An inverted nucleotide cap refers to a 3'→5' sequence of nucleic acids attached to the miRNA inhibitor at the 5' and/or the 3' end. There is no limit to the maximum number of nucleotides in the inverted cap just as long as it does not interfere with binding of the miRNA inhibitor to its target microRNA. Any nucleotide can be used in the inverted nucleotide cap. Typically, the inverted nucleotide cap is one nucleotide in length. The nucleotide for the inverted cap is generally thymine, but can be any nucleotide such as adenine, guanine, uracil, or cytosine.

Alternatively, an ethylene glycol compound and/or amino linkers can be attached to the either or both ends of the miRNA inhibitor Amino linkers can also be used to increase nuclease resistance of the miRNA inhibitors to endonucleases.

Chimeric miRNA inhibitors containing a mixture of any of the moieties mentioned above are also known, and may be made by methods known, in the art. See, for example, references cited above, and Wang et al, Proc. Natl. Acad. Sci. USA 96, 13989-13994 (1999), Liang et al., Eur. J. Biochem. 269, 5753-5758 (2002), Lok et al., Biochemistry 41, 3457-3467 (2002), and Damha et al., J. Am. Chem. Soc. 120, 12976-12977 (2002).

Also included are antagomirs. The term "antagomir" or "antagomiR" refers to antisense miRNA oligonucleotides containing 2'-OMe substitutions throughout, phosphorothioate linkages in the first two 5' and last three 3' nucleotides, and a cholesterol moiety attached at the 3' end.

The linking between two nitrogenous bases on opposite complementary DNA or RNA strands that are connected via hydrogen bonds are called a base pair (often abbreviated bp). In the canonical Watson-Crick DNA base pairing, adenine (A) forms a base pair with thymine (T) and guanine (G) forms a base pair with cytosine (C). In RNA, thymine is replaced by uracil (U). A wobble base pair is a non-Watson-Crick base pairing between two nucleotides in RNA molecules. The four main wobble base pairs are guanine-uracil, inosine-uracil, inosine-adenine, and inosine-cytosine (G-U, I-U, I-A and I-C). The thermodynamic stability of a wobble base pair is comparable to that of a Watson-Crick base pair. In discussing complementarity herein, both types of base pairing are included.

Polynucleotides herein are selected to be 'substantially' complementary to different strands of a particular target miRNA sequence. This means that the polynucleotides must be sufficiently complementary to hybridize with their respective strands. Therefore, the polynucleotide sequence need not reflect the exact sequence of the target sequence. For example, a non-complementary nucleotide fragment may be attached to the 5' end of the polynucleotide, with the remainder of the polynucleotide sequence being complementary to the strand. Alternatively, non-complementary bases or longer sequences can be interspersed into the polynucleotide, provided that the polynucleotide sequence has sufficient complementarity with the sequence of the strand to hybridize therewith under stringent conditions or to form the template for the synthesis of an extension product.

Predictions of the binding energy or calculation of thermodynamic indices between an oligonucleotide and a complementary sequence in an mRNA molecule may be utilized (Chiang et al. (1991) J. Biol. Chem. 266:18162-18171; Stull et al. (1992) Nucl. Acids Res. 20:3501-3508). Antisense oligonucleotides may be selected on the basis of secondary structure (Wickstrom et al (1991) in Prospects for Antisense Nucleic Acid Therapy of Cancer and AIDS, Wickstrom, ed., Wiley-Liss, Inc., New York, pp. 7-24; Lima et al. (1992) Biochem. 31:12055-12061). In addition, any of a variety of computer programs may be utilized which predict suitable antisense oligonucleotide including antagomir sequences utilizing various criteria recognized by the skilled artisan, including for example the absence of self-complementarity, the absence hairpin loops, the absence of stable homodimer and duplex formation (stability being assessed by predicted energy in kcal/mol). Examples of such computer programs are readily available and known to the skilled artisan and include the OLIGO 4 or OLIGO 6 program (Molecular Biology Insights, Inc., Cascade, Colo.) and the Oligo Tech program (Oligo Therapeutics Inc., Wilsonville, Oreg.).

In one aspect, the present invention provides for miRNA inhibitors having the following sequences:

TABLE 2

| miRNA target | Inhibitor Sequence | |
|---|---|---|
| miR-133 | 3'-AAACCAGGGGAAGUUGGUCGAUA-5' | SEQ ID NO: 6 |
| miR-133 | 5'-AUAGCUGGUUGAAGGGGACCAAA-3' | SEQ ID NO: 6 |
| miR-133 | 5'-*mA*mUmAmGmCmUmGmGmUmUmGmAmAmGm GmGmGmAmC*mC*mA*mA*mACh1-3' (antagomir) | | m represents a 2'-O-methyl-modified nucleotide.
*represents a phosphorothioate linkage.
Ch1 represents a 3' cholesterol moiety.

The antagomiR sequence lines up with human miR133a and miR133b (discussed above), as is shown below:

```
hsa-miR-133a:
5'-UUUGGUCCCCUUCAACCAGCUG-3'      (SEQ ID NO: 4)

hsa-miR-133b:
5'-UUUGGUCCCCUUCAACCAGCUA-3'      (SEQ ID NO: 5)

miR-133 antagomiR:
3'-AAACCAGGGGAAGUUGGUCGAUA-5'     (SEQ ID NO: 6)
```

The miR-133 antagomiR contains a "U" at the position corresponding to the 3' end of the miR-133a and miR133b. The "U" can base-pair with either the "A" in the miR-133b (Watson/Crick base-pairing) or the "G" in the miR-133a (Wobble pairing). Furthermore, the antagomiR has an extra "A" at its 5' end. This "A" is thought not to base pair with the miR-133a/b, but provides an additional phosphorothioate linkage and hence improved stability.

The miRNA inhibitors of the invention may comprise at least ten contiguous, preferably at least thirteen contiguous, more preferably at least fifteen contiguous, and even more preferably at least twenty contiguous bases that have the same sequence as a sequence of bases in any one of the miRNA inhibitors shown in Table 2. The miRNA inhibitors optimally comprise the entire sequence of any one of the miRNA inhibitor sequences shown in Table 2.

In one aspect, the miRNA inhibitors comprise a sequence that is complementary to at least 6 contiguous nucleotides in an miRNA-133. The sequence may be complementary to at least 10, 12, 14, 15, 16, 17, 18, 19, 20, 21, or 22 contiguous nucleotides of said microRNAs.

For the contiguous bases mentioned above, up to thirty percent of the base pairs may be substituted by wobble base pairs. As used herein, wobble base pairs refers to either: i) substitution of a cytosine with a uracil, or 2) the substitution of a adenine with a guanine, in the sequence of the miRNA inhibitor. These wobble base pairs are generally referred to as UG or GU wobbles.

Further, up to ten percent, and preferably up to five percent of the contiguous bases can be additions, deletions, mismatches or combinations thereof. Additions refer to the insertion in the contiguous sequence of any moiety described above comprising any one of the bases described above. Deletions refer to the removal of any moiety present in the contiguous sequence. Mismatches refer to the substitution of one of the moieties comprising a base in the contiguous sequence with any of the above described moieties comprising a different base.

The additions, deletions or mismatches can occur anywhere in the contiguous sequence, for example, at either end of the contiguous sequence or within the contiguous sequence of the miRNA inhibitor. If the contiguous sequence is relatively short, such as from about ten to about 15 moieties in length, preferably the additions, deletions or mismatches occur at the end of the contiguous sequence. If the contiguous sequence is relatively long, such as a minimum of sixteen contiguous sequences, then the additions, deletions, or mismatches can occur anywhere in the contiguous sequence.

The sequence of bases in the miRNA inhibitors of the present invention can be derived from a microRNA from any species e.g. such as a fly (e.g., *Drosophila melanogaster*), a worm (e.g., *C. elegans*). Preferably the sequence of bases is found in mammals, especially humans (*H. sapiens*), mice (e.g., *M. musculus*), and rats (*R. norvegicus*).

The miRNA inhibitor is preferably isolated, which means that it is essentially free of other nucleic acids. Essentially free from other nucleic acids means that it is at least 90%, preferably at least 95% and, more preferably, at least 98% free of other nucleic acids.

Preferably, the molecule is essentially pure, which means that the molecule is free not only of other nucleic acids, but also of other materials used in the synthesis of the molecule, such as, for example, enzymes used in the synthesis of the molecule. The molecule is at least 90% free, preferably at least 95% free and, more preferably, at least 98% free of such materials.

The method comprises introducing into the cell a single-stranded microRNA molecule. In one aspect, said cells are myogenic cells, satellite cells, myoblasts, brown adipocyte progenitor cells, or brown pre-adipocytes.

Any miRNA-133 inhibitor can be used in the methods of the present invention. With regards to an oligonucleic miRNA-133 inhibitor, any such inhibitor can be used, as long as the anti-microRNA is complementary, subject to the restrictions described herein, to a microRNA-133.

Inhibition of miRNA Target(s) expression can be measured in ways which are routine in the art, for example by RT-PCR analysis, Northern blot assay of RNA expression or Western blot assay of protein expression as well known to the skilled artisan.

Preparation of Nucleic Acids:

A nucleic acid may be made by any technique known to one of ordinary skill in the art, such as for example, chemical synthesis, enzymatic production or biological production. Though synthetic miRNAs according to the invention could be produced using recombinant methods, it is preferred to produce synthetic miRNAs by chemical synthesis or enzymatic production. Likewise, miRNA inhibitors are preferentially produced by chemical synthesis or enzymatic production. Non-synthetic miRNAs can be produced by a number of methods, including methods involving recombinant DNA technology.

Nucleic acid synthesis is performed according to standard methods. See, for example, Itakura and Riggs (1980). Additionally, U.S. Pat. No. 4,704,362, U.S. Pat. No. 5,221,619, and U.S. Pat. No. 5,583,013 each describe various methods of preparing synthetic nucleic acids. Non-limiting examples of a synthetic nucleic acid (e.g., a synthetic oligonucleotide), include a nucleic acid made by in vitro chemically synthesis using phosphotriester, phosphite or phosphoramidite chemistry and solid phase techniques such as described in EP 266,032, incorporated herein by reference, or via deoxynucleoside H-phosphonate intermediates as described by Froehler et al., 1986 and U.S. Pat. No. 5,705,629, each incorporated herein by reference. In the methods of the present invention, one or more oligonucleotide may be used. Various different mechanisms of oligonucleotide synthesis have been disclosed in for example, U.S. Pat. Nos. 4,659,774, 4,816, 571, 5,141,813, 5,264,566, 4,959,463, 5,428,148, 5,554,744, 5,574,146, 5,602,244, each of which is incorporated herein by reference.

Pharmaceutical Formulations and Routes of Administration

The miRNA inhibitors of the present invention may be formulated in a conventional manner using one or more carriers, excipients or diluents. The composition may thus comprise the miRNA inhibitor of the invention and a carrier, excipient, and/or diluent; in a further aspect, the carrier, excipient, and/or diluent is a pharmaceutically-acceptable carrier, excipient, and/or diluent.

For pharmaceutical use, the miRNA inhibitor or a composition thereof is, for instance, administered orally, sublingually, rectally, nasally, vaginally, topically (including the use of a patch or other transdermal delivery device), by pulmonary route by use of an aerosol, or parenterally, including, for example, intramuscularly, subcutaneously, intraperitoneally, intraarterially, intravenously or intrathecally. Administration can be by means of a pump for periodic or continuous delivery. The miRNA inhibitor is administered alone, or is combined with a pharmaceutically-acceptable carrier or excipient according to standard pharmaceutical practice.

For the oral mode of administration, the inhibitors of the invention are used in the form of tablets, capsules, caplets, pellets, granules lozenges, chewing gum, troches, powders, syrups, elixirs, aqueous solutions and suspensions, and the like. In the case of tablets, carriers that are used include lactose, sodium citrate and salts of phosphoric acid. Pharmaceutically acceptable excipients include such as binding agents (e.g., pregelatinized maize starch, polyvinylpyrrolidone or hydroxypropyl methylcellulose); fillers (e.g., lactose, microcrystalline cellulose or calcium phosphate); lubricants (e.g., magnesium stearate, talc or silica); disintegrants (e.g., potato starch or sodium starch glycolate); or wetting agents (e.g., sodium lauryl sulphate). The tablets may be coated by methods well known in the art. In the case of tablets, capsule, caplets, pellets or granules for oral administration pH sensitive enteric coatings, such a Eudragits™ designed to control the release of active ingredients may be employed. If desired, certain sweetening and/or flavoring agents are added.

Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, methyl cellulose or hydrogenated edible fats); emulsifying agents (e.g., lecithin or acacia); non-aqueous vehicles (e.g., almond oil, oily esters or ethyl alcohol); and preservatives (e.g., methyl or propyl p-hydroxybenzoates or sorbic acid). Useful diluents include lactose and high molecular weight polyethylene glycols.

For parenteral administration, sterile solutions of the inhibitors of the invention are usually prepared, and the pH's of the solutions are suitably adjusted and buffered. For intravenous use, the total concentration of solutes should be controlled to render the preparation isotonic. For ocular administration, ointments or droppable liquids may be delivered by ocular delivery systems known to the art such as applicators or eye droppers. Such compositions can include mucomimetics such as hyaluronic acid, chondroitin sulfate, hydroxypropyl methylcellulose or polyvinyl alcohol, preservatives such as sorbic acid, EDTA or benzyl chromium chloride, and the usual quantities of diluents and/or carriers. For pulmonary administration, diluents and/or carriers will be selected to be appropriate to allow the formation of an aerosol. The inhibitors of the invention may be formulated for parenteral administration by injection, including using conventional catheterization techniques or infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulating agents such as suspending, stabilizing and/or dispersing agents. Alternatively, the active ingredient may be in a powder form for reconstitution with a suitable vehicle, e.g., sterile pyrogen-free water, before use.

In one aspect, the inhibitor of the invention is administered intramuscularly or is formulated for intramuscular administration.

Suppository forms of the inhibitors of the invention are useful for vaginal, urethral and rectal administrations. Such suppositories will generally be constructed of a mixture of substances that is solid at room temperature but melts at body temperature. The substances commonly used to create such vehicles include the obroma oil, glycerinated gelatin, cocao butter, other glycerides, hydrogenated vegetable oils, and mixtures of polyethylene glycols of various molecular weight and fatty acid esters of polyethylene glycol. See, Remington's Pharmaceutical Sciences, $16^{th}$ Ed., Mack Publishing, Easton, Pa., 1980, pp. 1530-1533 for further discussion of suppository dosage forms. Analogous gels or creams can be used for vaginal, urethral and rectal administrations.

For intranasal administration or administration by inhalation, the active inhibitors of the invention are conveniently delivered in the form of a solution, dry powder formulation or suspension from a pump spray container that is squeezed or pumped by the patient or as an aerosol spray presentation from a pressurized container or a nebulizer, with the use of a suitable propellant, e.g., dichlorodifluoromethane, trichlorofluoromethane, dichlorotetrafluoroethane, heptafluoroalkanes, carbon dioxide or other suitable gas. In the case of a pressurized aerosol, the dosage unit may be determined by providing a valve to deliver a metered amount. The pressurized container or nebulizer may contain a solution or suspension of the active compound. Capsules and cartridges (made, for example, from gelatin) for use in an inhaler or insufflator may be formulated containing a powder mix of a compound of the invention and a suitable powder base such as lactose or starch.

Numerous administration vehicles will be apparent to those of ordinary skill in the art, including without limitation slow release formulations, liposomal formulations and polymeric matrices. The inhibitors of the invention can also be formulated for sustained delivery according to methods well known to those of ordinary skill in the art. Examples of such formulations can be found in U.S. Pat. Nos. 3,538,214; 4,060, 598; 4,173,626; 3,119,742; and 3,492,397, which are incorporated herein by reference in their entirety.

The polynucleotide may be incorporated within a variety of macromolecular assemblies or compositions. Such complexes for delivery may include a variety of liposomes, nanoparticles, and micelles, formulated for delivery to a patient. The complexes may include one or more fusogenic or lipophilic molecules to initiate cellular membrane penetration. Such molecules are described, for example, in U.S. Pat. No. 7,404,969 and U.S. Pat. No. 7,202,227, which are hereby incorporated by reference in their entireties.

The composition or formulation may employ a plurality of therapeutic polynucleotides, each independently as described herein. For example, the composition or formulation may employ from 1 to 5 miRNA inhibitors.

The polynucleotides of the invention may be formulated as a variety of pharmaceutical compositions. Pharmaceutical compositions will be prepared in a form appropriate for the intended application. Generally, this will entail preparing compositions that are essentially free of pyrogens, as well as other impurities that could be harmful to humans or animals Exemplary delivery/formulation systems include colloidal dispersion systems, macromolecule complexes, nanocapsules, microspheres, beads, and lipid-based systems including oil-in-water emulsions, micelles, mixed micelles, and liposomes. Commercially available fat emulsions that are suitable for delivering the nucleic acids of the invention to cardiac and skeletal muscle tissues include Intralipid®, Liposyn®, Liposyn® II, Liposyn® III, Nutrilipid, and other similar lipid emulsions. A preferred colloidal system for use as a delivery vehicle in vivo is a liposome (i.e., an artificial membrane vesicle). The preparation and use of such systems is well known in the art. Exemplary formulations are also disclosed in U.S. Pat. No. 5,981,505; U.S. Pat. No. 6,217,900; U.S. Pat. No. 6,383,512; U.S. Pat. No. 5,783,565; U.S. Pat. No. 7,202,227; U.S. Pat. No. 6,379,965; U.S. Pat. No. 6,127,170; U.S. Pat. No. 5,837,533; U.S. Pat. No. 6,747,014; and WO03/093449, which are hereby incorporated by reference in theft entireties.

The compound (i.e. the inhibitor) of the invention including pharmaceutically acceptable salts and solvates thereof may be used on their own but will generally be administered in the form of a pharmaceutical composition in which the compound (active ingredient) is in association with a pharmaceutically acceptable adjuvant, diluent or carrier. The pharmaceutical compositions and formulations may employ appropriate salts and buffers to render delivery vehicles stable and allow for uptake by target cells. Aqueous compositions of the present invention comprise an effective amount of the delivery vehicle comprising the inhibitor polynucleotides (e.g. liposomes or other complexes), dissolved or dispersed in a pharmaceutically acceptable carrier or aqueous medium. The phrases "pharmaceutically acceptable" or "pharmacologically acceptable" refers to molecular entities and compositions that do not produce adverse, allergic, or other untoward reactions when administered to an animal or a human. As used herein, "pharmaceutically acceptable carrier" may include one or more solvents, buffers, solutions, dispersion media, coatings, antibacterial and antifungal agents, isotonic and absorption delaying agents and the like acceptable for use in formulating pharmaceuticals, such as pharmaceuticals suitable for administration to humans. The use of such media and agents for pharmaceutically active substances is well known in the art. Supplementary active ingredients also can be incorporated into the compositions.

Depending on the mode of administration, the pharmaceutical composition will preferably comprise from 0.05 to 99% w (percent by weight), more preferably from 0.10 to 70% w, of active ingredient, and, from 1 to 99.95% w, more preferably from 30 to 99.90% w, of a pharmaceutically acceptable adjuvant, diluent or carrier, all percentages by weight being based on total composition.

The physician or other health care professional can select the appropriate dose and treatment regimen based on the subject's weight, age, and physical condition. Dosages will generally be selected to maintain a serum level of inhibitors of the invention between 0.01 µg/cc and about 1000 µg/cc, preferably between about 0.1 µg/cc and about 100 µg/cc. For parenteral administration, an alternative measure of preferred amount is from about 0.001 mg/kg to about 10 mg/kg (alternatively, from about 0.01 mg/kg to about 10 mg/kg), more preferably from about 0.01 mg/kg to about 1 mg/kg (from about 0.1 mg/kg to about 1 mg/kg), will be administered. For oral administrations, an alternative measure of preferred administration amount is from about 0.001 mg/kg to about 10 mg/kg (from about 0.1 mg/kg to about 10 mg/kg), more preferably from about 0.01 mg/kg to about 1 mg/kg (from about 0.1 mg/kg to about 1 mg/kg). For administrations in suppository form, an alternative measure of preferred administration amount is from about 0.1 mg/kg to about 10 mg/kg, more preferably from about 0.1 mg/kg to about 1 mg/kg.

The miRNA inhibitors or microRNAs can be introduced into a cell by any method known to those skilled in the art. Useful delivery systems, include for example, liposomes and charged lipids. Liposomes typically encapsulate oligonucleotide molecules within their aqueous center. Charged lipids generally form lipid-oligonucleotide molecule complexes as a result of opposing charges. These liposomes-oligonucleotide molecule complexes or lipid-oligonucleotide molecule complexes are usually internalized by endocytosis. The liposomes or charged lipids generally comprise helper lipids which disrupt the endosomal membrane and release the oligonucleotide molecules.

Other methods for introducing an miRNA inhibitor or a microRNA into a cell include use of delivery vehicles, such as dendrimers, biodegradable polymers, polymers of amino acids, polymers of sugars, and oligonucleotide-binding nanoparticles. In addition, pluoronic gel as a depot reservoir can be used to deliver the anti-microRNA oligonucleotide molecules over a prolonged period. The above methods are described in, for example, Hughes et al., Drug Discovery Today 6, 303-315 (2001); Liang et al. Eur. J. Biochem. 269 5753-5758 (2002); and Becker et al., In *Antisense Technology in the Central Nervous System* (Leslie, R. A., Hunter, A. J. & Robertson, H. A., eds), pp. 147-157, Oxford University Press.

Targeting of an miRNA inhibitor or a microRNA to a particular cell can be performed by any method known to those skilled in the art. For example, the miRNA inhibitor or microRNA can be conjugated to an antibody or ligand specifically recognized by receptors on the cell.

Applicants have shown that local antagonism of microRNA-133 during muscle regeneration also augments energy expenditure, improves glucose tolerance and impedes the development of diet-induced obesity. In one embodiment, use of antisense oligonucleotides (antagomiR) for antagonizing miR-133 function in activated satellite cells in response to muscle injury, resulted in the induction of brown adipocytes within the muscle interstitium. Thus, the Applicant demonstrated that functional brown adipocytes are efficiently induced from satellite cells by inhibiting miR-133 function during muscle regeneration. In one aspect, the present invention provides for administration of the miRNA-133 inhibitor with activation of satellite cells. Satellite cells may be activated by injury and/or exercise. In one aspect, said activation may occur prior to, concurrently with, or after administration of said miRNA-133 inhibitor.

Assay

MicroRNAs are 20-23 nt non-coding small RNAs, which play pivotal roles in post-transcriptional gene expression regulation. MicroRNAs in the RNA-Induced Silencing Complex (RISC) bind to the target sites of the targeting mRNAs (frequently located in 3' untranslated regions and partially reverse complementary to the microRNA sequences) and repress the expression of the latter. As discussed above, Applicant recently discovered that miR-133, a muscle-enriched microRNA, controls the brown adipose determination of muscle stem cells, in one aspect by targeting Prdm16, and thus prevents the brown adipose tissue (BAT) formation within skeletal muscles. Applicant found that miR-133 antagonism, efficiently induced by intramuscular injection of miR-133 antisense oligonucleotide, lead to ectopic BAT formation and hence increased energy expenditure as well as resistance to diet-induced obesity in mouse models.

In one aspect, the present invention provides a screening assay for small molecules that regulate the functionality of miR-133. Advantageously, such miR-133-regulatory molecules are useful in elucidating the signalling pathways governing miR-133 expression in vivo. In a further aspect, such molecules are for use as anti-obesity drugs.

In one aspect, such an assay is a high throughput screenings (HTS) assay. In one aspect, the invention provides a simple yet robust system that transforms quantitative levels of miR-133 functionality in live cells into machine-readable signals. Although direct measurement of miR-133 expression levels is plausible by utilizing hybridization-based methods (e.g. qRT-PCR, NanoString technologies) or sequencing-based methods (e.g. high-throughput sequencing), application of such methods to HTS is greatly hindered by their associated costs, and laborious human-involved handling procedures.

The design of the miR-133 biosensor in this invention disclosure is based on the principle that recognition of microRNA target sites in 3'UTR by microRNA/RISC leads to the inhibition of the translation of the target mRNAs. Applicant designed an artificial 3'UTR containing optimized miR-133 target sites in tandem. This 3'UTR was cloned downstream of the open reading frames of firefly luciferases and green fluorescence protein (GFP), which together function as an miR-133 biosensor. While firefly luciferases and green fluorescence protein (GFP) were used in the particular embodiment, one or more other fluorescent or bioluminescent markers could be used in the biosensor cassette. Such markers are commonly used, for example, in assessing protein expression. And such markers would be known to a person of skill in the art. This miR-133 biosensor cassette was cloned downstream of a CMV promoter in a lentiviral vector with puromycin resistance gene driven by an EF-1 promoter. Other promoters, vectors, and optionally resistance genes would be known to a person of skill in the art and could be used. C2C12 myoblast clones, infected with lentiviruses carrying the miR-133 biosensor and selected by Puromycin, provide an HTS based on the reverse correlation between miR-133 functionality and luciferase/GFP intensities.

In one aspect, such an HTS assay or biosensor may have the following advantages:

a) the miR-133 target site in the biosensor is optimized to increase the likelihood of miR-133 targeting yet prevent the cleavage of biosensor transcripts by RISC. As microRNAs act to dynamically regulate the expression of their target mRNAs, the permanent cleavage of mRNA transcripts by RISC will in theory decrease the sensitivity of this biosensor in HTS. In addition, the cleavage of mRNAs by RISC is known to initiate siRNA-like effects including transcriptional gene silencing in nucleus, which would be detrimental to the responsiveness of the biosensor to miR-133 functionality;

b) the biosensor of the invention contains tandem array of miR-133 target sites, which in one aspect advantageously increases the sensitivity of biosensor in response to miR-133 levels;

c) the biosensor of the invention is cloned in a lentiviral vector, which facilitates the introduction of the biosensor into both proliferating cells and post-mitotic cells; and d) the feasibility of selection for single cell clones makes it possible that all cells used in a screening carry the same numbers of provirus in the genomes at the same insertion sites, which in one aspect decreases the variance.

In other aspect, the microRNA biosensor construct may be modified in the following ways:

1) replacing the puromycin resistance gene with *renilla* luciferase gene. The *renilla* luciferase gene servers as an internal reference control for normalization. This modification allows the application of this design of biosensor to non-proliferating cells (e.g. cardiomyocytes) and primary cells with limited in vitro expansion potentials due to cellular senescence or loss of stemness (e.g. primary adipogenic progenitors).

2) replacing the CMV promoter with weaker promoters (e.g. SV40 promoter or PK promoter). A weaker promoter reduces the possibility of deviating target microRNAs from their endogenous targets to the exogenous biosensor as well as theoretically eases the identification of regulatory mechanisms that repress the target microRNA functionality.

In one aspect, the present invention provides a polynucleotide comprising a sequence complementary to at least 6 contiguous nucleotides of miRNA-133a (5'-uuugguccccuu-caaccagcug-3', SEQ ID NO:4) or complementary to at least 6 contiguous nucleotides of microRNA-133b (5'-uuugguc-cccuucaaccagcua-3', SEQ ID NO:5), for use in detecting miR-133a or miR-133b expression and/or functionality in vitro or in vivo.

In one aspect, the present invention provides an polynucleotide having a sequence:

5'-tagctggttgccaggaccaaaa-3' (SEQ ID NO:13)

In this embodiment, the sequence at positions 1 to 10 (tagctggttg) can base-pair with nucleotides 1322 of microRNA-133a or microRNA-133b. The sequence at positions 14 to 21 (ggaccaaa) can base-pair with nucleotides 1-8 of microRNA-133a or microRNA-133b. The sequence at positions 1113 (cca) presumably does not base-pair with central nucleotides 9-12 of microRNA-133a or microRNA-133b.

In one aspect, the present invention provides a tandem array sequence, which contains 2 or more of said complementary sequences, for use in detecting miR-133a or miR-133b expression and/or functionality in vitro or in vivo.

In one aspect, the present invention provides a use of the sequence described above or the tandem array sequence described above as a 3' un-translated region (3' UTR) associated with a reporter gene (e.g. GFP, luciferase) for the purpose of detecting miR-133a or miR-133b expression and/or functionality in vitro or in vivo.

The microRNA biosensors according to the invention are useful for high-throughput screening aiming at identifying small molecule drugs that regulate the functionality of target microRNAs in cellular contexts, and for live-cell/animal imaging allowing real-time detection of microRNA functionality in vivo and in vitro.

EXPERIMENTAL

Single Satellite Cells are Multipotent and Differentiate into Brown Adipocytes:

In adult muscles, satellite cells are characterized by their specific expression of Pax7 in both quiescent and activated states (Seale et al., 2000). To investigate the capability of satellite cells in adult skeletal muscle to undergo brown adipogenic differentiation, Applicant utilized a Cre/LoxP-based system for satellite cell lineage tracing (Nishijo et al., 2009). Pax7-CreER; R26R-tdTomato mice were injected with tamoxifin for 5 consecutive days at 6-weeks of age to induce permanent tdTomato expression in satellite cells and their descendants (data not shown).

From the extensor digitorum longus (EDL) muscles of these mice, Applicant isolated single myofibers (n>600), carrying labeled satellite cells embedded within their native niche, and cultured them under established pro-adipogenic conditions (Seale et al., 2008). Applicant observed adipocytes at a low frequency, characterized by their presence of oil droplets and cytoplasmic Perilipin A staining, mixed together with elongated multinucleated myotubes in the culture (FIG. 1A). Importantly, these adipocytes were brown adipocytes as evidenced by their nuclear staining for Prdm16 (FIG. 1A). As expected, all multinucleated myotubes were labeled with tdTomato, indicating their satellite cell origin. Notably, those Prdm16$^{pos}$ brown adipocytes were also labeled with tdTomato, indicating that they were similarly derived from Pax7-expressing satellite cells (FIG. 1A). Overall, satellite cell-derived brown adipocytes (SC_BA) counted for 0.1% of tdTomato-labeled cells in these cultures. By contrast, brown adipogenic differentiation of satellite cells was not observed under pro-myogenic culture conditions (Kuang et al., 2007).

Satellite cells represent a heterogeneous population containing stem cells and committed cells (Wang and Rudnicki, 2011). By lineage tracing, Applicant has previously identified a satellite stem cell population (Pax7$^{pos}$, Myf5-Cre-YFP$^{neg}$) that can undergo asymmetric cell divisions to generate committed satellite myogenic progenitors (Pax7$^{pos}$, Myf5-Cre-YFP$^{pos}$) (Kuang et al., 2007). To measure the potential of these two satellite cell subpopulations to undergo brown adipogenesis, Applicant employed fluorescence activated cell sorting (FACS) to isolate total satellite cells from Pax7-ZsGreen; Myf5-Cre; R26R-tdTomato mice on the basis of their ZsGreen fluorescence (Bosnakovski et al., 2008), and further separate them into satellite stem cell (ZsGreen$^{pos}$, Myf5-Cre-tdTomato$^{neg}$) and satellite myogenic progenitor (ZsGreen$^{pos}$, Myf5-Cre-tdTomato$^{pos}$) subpopulations by tdTomato fluorescence.

Figure 1B:
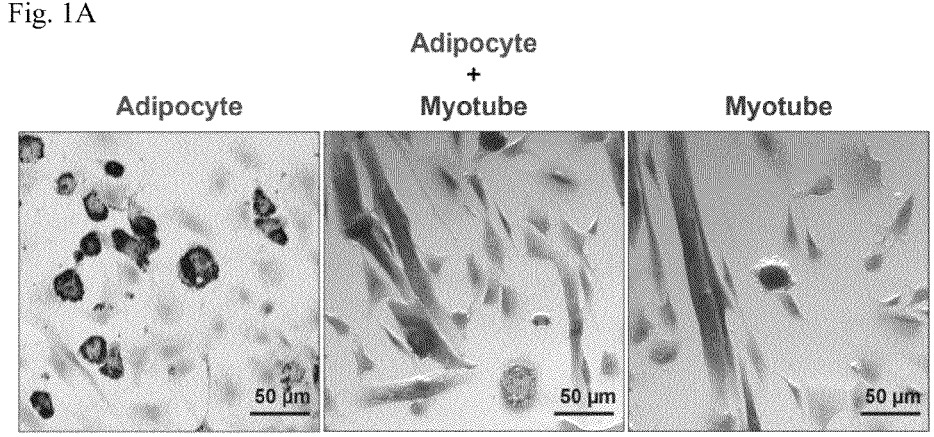
Figure 1B:
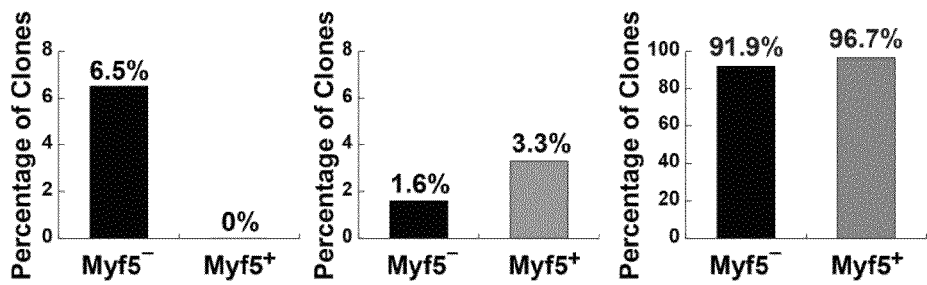

To address whether these two subpopulations of satellite cells are multipotent (myogenic and adipogenic) at the clonal level, Applicant sorted single satellite stem cells or satellite myogenic progenitors into individual wells (n>2,000 for each cell type). The reliability of sorting single satellite cells into individual wells was confirmed by visual inspection of all wells. Applicant found that 6.5% of single satellite stem cell-derived clones contained exclusively Oil Red O (ORO)-positive adipocytes whereas this kind of clone was not observed from satellite myogenic progenitor clones (FIG. 1B, left). Notably, 1.6% of satellite stem cell clones and 3.3% of satellite progenitor clones contained mixed adipocytes and myotubes supporting the notion that satellite cells are multipotent (FIG. 1B, middle). The majority of satellite cell clones exclusively formed muscle-containing colonies (FIG. 1B, right). These data demonstrate that satellite cells are multipotent and can clonally give rise to both myogenic and brown adipogenic cells.

Prdm16 is Targeted by miR-133:

Applicant hypothesized that brown adipose determination of satellite cells is controlled by microRNAs, which regulate the expression of Prdm16 or other brown adipose determinants Therefore, Applicant performed whole-transcriptome RNA sequencing (RNA-Seq) for satellite cells and brown preadipocytes isolated from adult hind limb muscles and interscapular BAT (iBAT), respectively, by established FACS schemes (Scime et al., 2005). Applicant identified 580 mRNAs and 88 microRNAs, which are differentially expressed between two cell lineages.

Figure 2A:
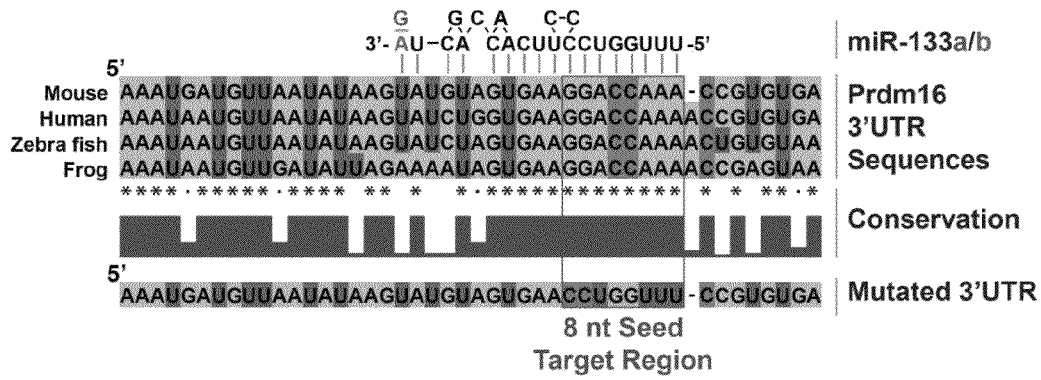
FIG. 2 shows Prdm16 Is Targeted By miR-133: (A) Prdm16 3'UTR contains a conserved target site for both miR-133a and miR-133b. The absolutely conserved 8-nt seed sequences in multiple genomes and a mutated seed sequence used in this study (Prdm16_mutUTR) were enclosed in a frame. (B) Luciferase assays and RT-qPCR indicate miR-133 targets Prdm16 3'UTR and represses Prdm16 expression. This repression depends on the predicted 8-nt seed sequence. Ectopic miR-133 was over-expressed in HEK293T cells together with Renilla luciferase reporter constructs containing either intact or mutated Prdm16 3'UTR. The repression of luciferase activity and the reduction of luciferase expression by miR-133 was abolished by mutating the predicted 8-nt seed sequence. (C) Immunoblots reveals that lentiviral miR-133 over-expression (ov.) in primary brown preadipocytes repressed Prdm16 and PGC1-α protein levels. (D) Representative images depict that adipogenic differentiation from primary brown preadipocytes was severely impaired by miR-133 over-expression. Oil Red O staining revealed drastically reduced number of differentiated adipocytes with oil droplets in the miR-133 ov. culture while DAPI staining of the same fields indicated that same near-confluent density of cells were present for both cultures. (E) RT-qPCR shows lentiviral over-expression of miR-133 or inhibition of miR-133 by antisense oligos impaired or enhanced brown adipogenic commitment in primary brown preadipocytes, respectively. Notably, impaired brown adipogenic commitment in the miR-133 ov. culture was companied with the emergence of myogenic differentiation as evidenced by increased expression of myogenic markers (Pax7, MyoD, Myog, MyHC) and white adipogenic differentiation as evidenced by increased expression of Leptin. Error bars: S.E.M., asterisk: significant pair-wise comparison by t-test, *: $p \leq 0.05$, : $p \leq 0.01$, *: $p \leq 0.001$.
Figure 2B:
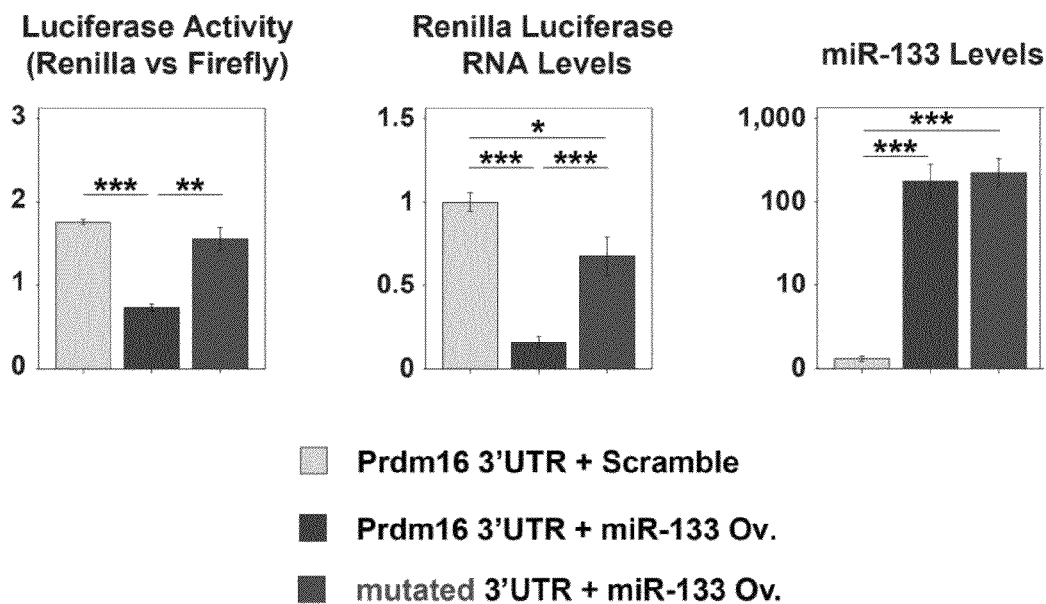

Satellite cell-enriched microRNAs and their predicted transcription factor targets enriched in brown preadipocytes were plotted to identify negative regulatory networks. Analysis of the network suggested that Prdm16 is repressed by the satellite cell-enriched miR-133a and miR-133b. Applicant thus identified a highly conserved target site for miR-133a and miR-133b with an absolutely conserved 8-nucleotide seed sequence in the 3'UTR of Prdm16 mRNA (FIG. 2A). The conservation of the seed sequence suggests biological relevance of these microRNAs in regulating Prdm16 expression in humans Applicant performed luciferase assays and RT-qPCR to investigate the direct targeting of Prdm16 3'UTR by miR-133. HEK293T cells transfected with reporter plasmids containing the Prdm16 3'UTRs showed markedly decreased luciferase activity and luciferase mRNA level in the presence of ectopic miR-133 (FIG. 2B). Mutation of the conserved 8-nt seed sequence abrogated the miR-133-induced repression of the Prdm16 3'UTR Similar results were also observed in C2C12 myoblasts.

miR-133 belongs to a group of myomiRs, which are specifically expressed in muscles and myogenic cells (Chen et al., 2006; Williams et al., 2009). Applicant confirmed the inverse expression patterns of Prdm16 and miR-133 in FACS-sorted BAT progenitors, satellite cell populations and cultured primary myoblasts. Applicant also determined that myogenic determinant Pax7 is a bona fide transcriptional activator of miR-133. Thus, Applicant hypothesized that direct targeting of Prdm16 by miR-133 represents a potential regulatory mechanism in brown adipose determination.

Over-Expression of miR-133 Impairs Lineage Commitment of Brown Preadipocytes:

Primary brown preadipocytes express low but evident levels of miR-133 (Walden et al., 2009). Therefore, Applicant tested the effects of miR-133 over-expression on the brown adipose lineage fate of primary brown preadipocytes. To avoid "off-target" and "overloading" side effects, Applicant utilized a lentivirus-based microRNA expression system to elevate the endogenous levels of miR-133 in primary brown preadipocytes within a physiological range.

Figure 2C:
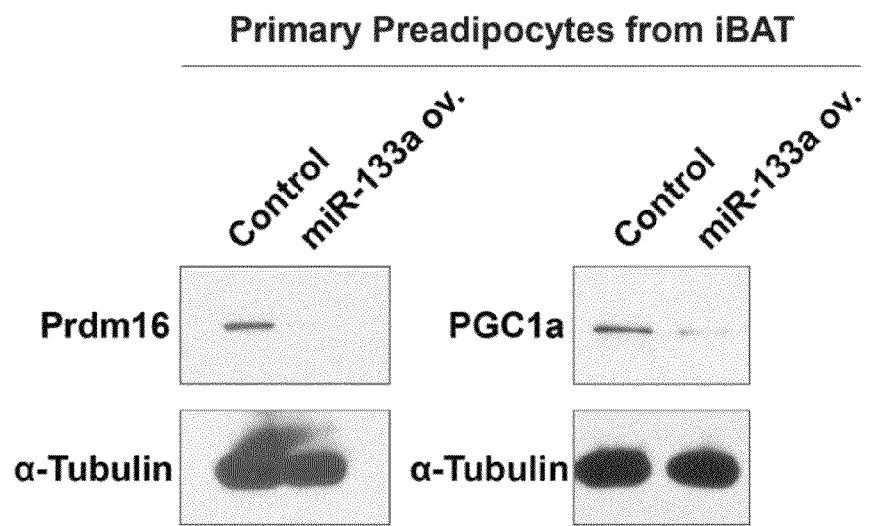
Figure 2D:
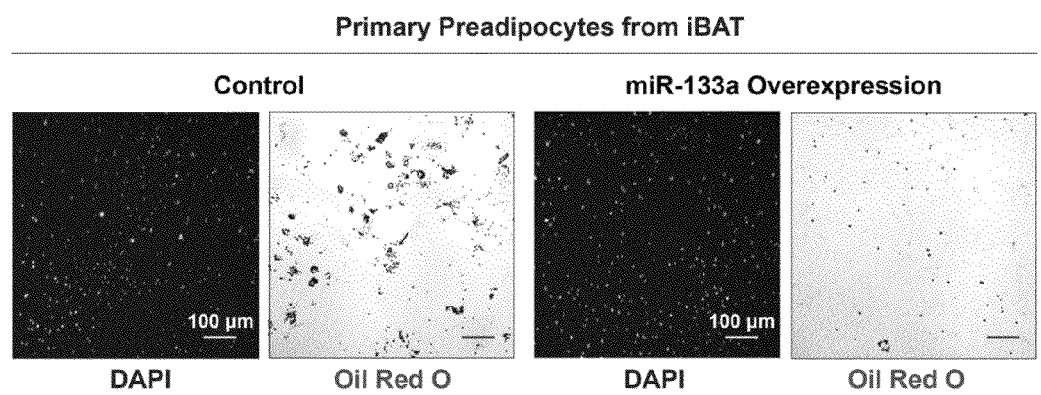

Lentiviral over-expression of miR-133 resulted in markedly reduced protein levels of Prdm16 and PGC1-α, which is a Prdm16 target and critical for BAT-specific thermogenic gene expression (Seale et al., 2007) (FIG. 2C). Moreover, over-expression of miR-133 strongly impaired adipogenic differentiation of brown preadipocytes at confluent density as evidenced by reduced number of ORO$^{pos}$ adipocytes in the differentiation cultures (FIG. 2D).

Figure 2E:
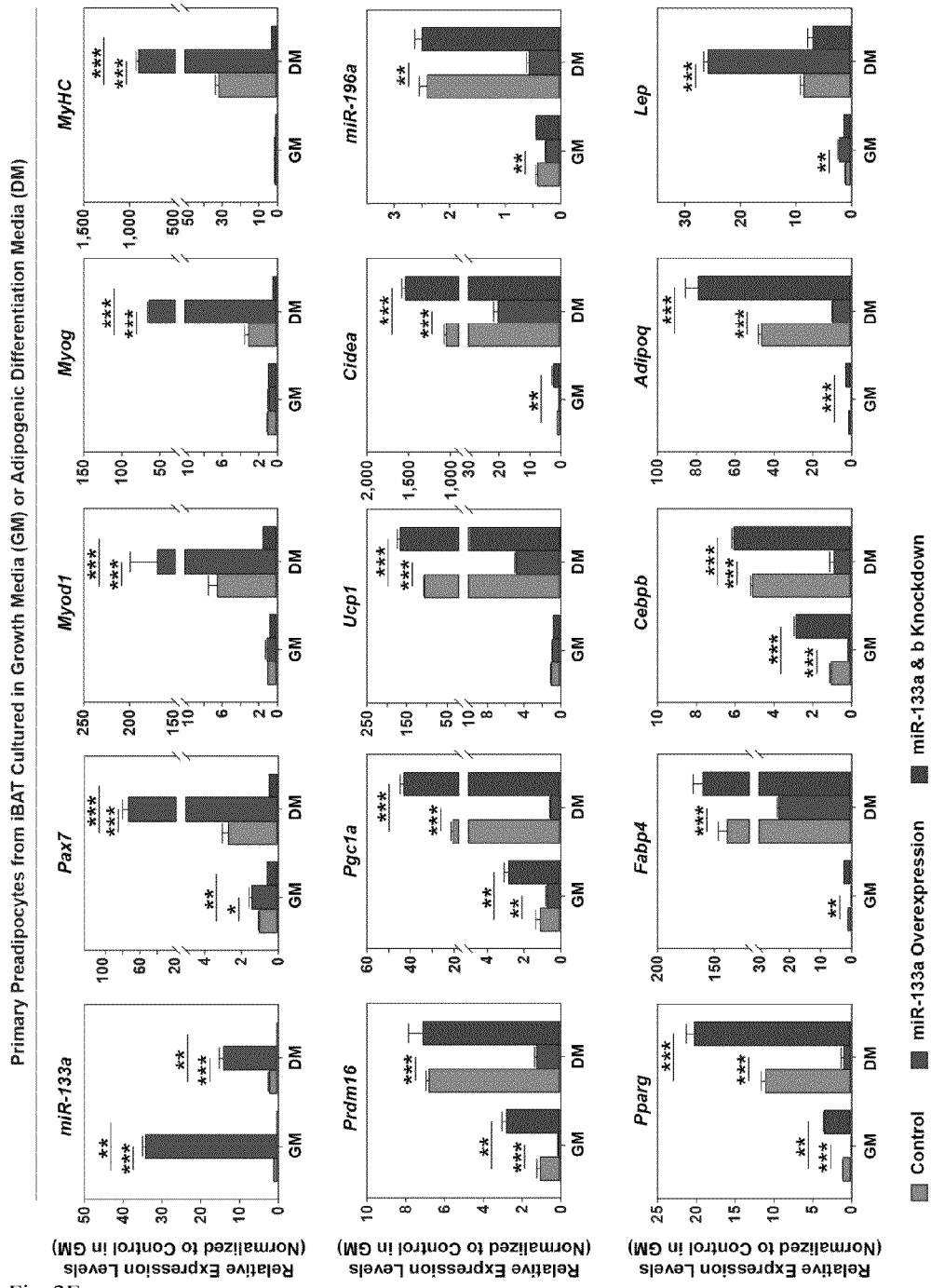

Applicant further performed RT-qPCR to investigate gene expression signatures associated with lineage commitment of brown preadipocytes in response to miR-133 over-expression or repression (FIG. 2E). Over-expression of miR-133 decreased the expression of brown adipogenic markers (Prdm16, Pgc1a, Ucp1, Cidea and miR-196a) as well as genes associated with general adipogenesis (Pparg, Fabp4, Cebpb and Adipoq). Notably, over-expression of miR-133 lead to markedly increased expression levels of myogenic transcription factors, Pax7, MyoD, Myogenin as well as a myogenic differentiation marker, myosin heavy chain 2 (MyHC). A white adipocyte-specific marker, Leptin, was also increased in miR-133 over-expression culture. By contrast, inhibition of miR-133 enhanced brown adipogenic commitment and differentiation as evidenced by increased expression of Prdm16, Pgc1a, Ucp1, Cidea, Pparg, Cebpb and Adipoq, as well as decreased expression of Pax7, MyoD, Myogenin and MyHC (FIG. 2E). These data indicate that miR-133 regulates brown adipose determination in primary brown preadipocytes by targeting Prdm16.

Applicant investigated whether miR-133 prevents brown adipose determination by targeting genes in addition to Prdm16. To address this question, Applicant transiently expressed ectopic miR-133 in C3H10T1/2 mesenchymal progenitors in the absence or presence of ectopic Prdm16 lacking its 3'UTR (Prdm16_CDS) during the adipogenic determination stage (before adipogenic induction). In this manner, Applicant could assess whether miR-133 targets any other brown adipogenic determinants during adipogenic determination, whose repression cannot be rescued by Prdm16 ectopic expression.

In absence of Prdm16, ectopic expression of miR-133 moderately compromised the white adipose determination and differentiation of C3H10T1/2 progenitors as evidenced by reduced Perilipin A expression combined with lack of Prdm16 or Ucp1 expression. On the other hand, ectopic expression of Prdm16 markedly promoted brown adipose determination and differentiation as evidenced by increased Perilipin A expression combined with strong induction of Ucp1 and Pgc1α. Critically, ectopic expression of miR-133 together with Prdm16 led to a comparable, if not improved, brown adipocyte phenotype as compared to Prdm16 over-expression alone. In addition, over-expression of miR-133 in C3H10T1/2 progenitors appeared not to induce myogenic determination as observed from brown preadipocyte cultures.

These findings are consistent with the absence of miR-133 seed sequence in the 3'UTRs of Pparg, Pgc1a/b, Cebpa/b/d and Ucp1. Therefore, Applicant concluded that miR-133 prevents brown adipose determination by primarily targeting Prdm16.

miR-133 Prevents Brown Adipose Determination in Satellite Cells:

To investigate whether knockdown of miR-133 promotes the brown adipose determination in satellite cells, Applicant transfected satellite cells embedded within individual myofibers with mixtures of either antisense oligonucleotide (ASO) inhibitors or mimetics for miR-133a and miR-133b (>300 myofibers per treatment group). Remarkably, inhibition of miR-133 resulted in a pronounced increase of brown adipocytes in the culture, characterized by their nuclear Prdm16 staining and presence of oil droplets. Conversely, no brown adipocyte was observed in myofiber cultures transfected with miR-133 mimetics. Consistent with this finding, Applicant observed that endogenous miR-133 acts an efficacious block for Prdm16-dependent brown adipose induction in C2C12 myoblasts.

Figure 3A:
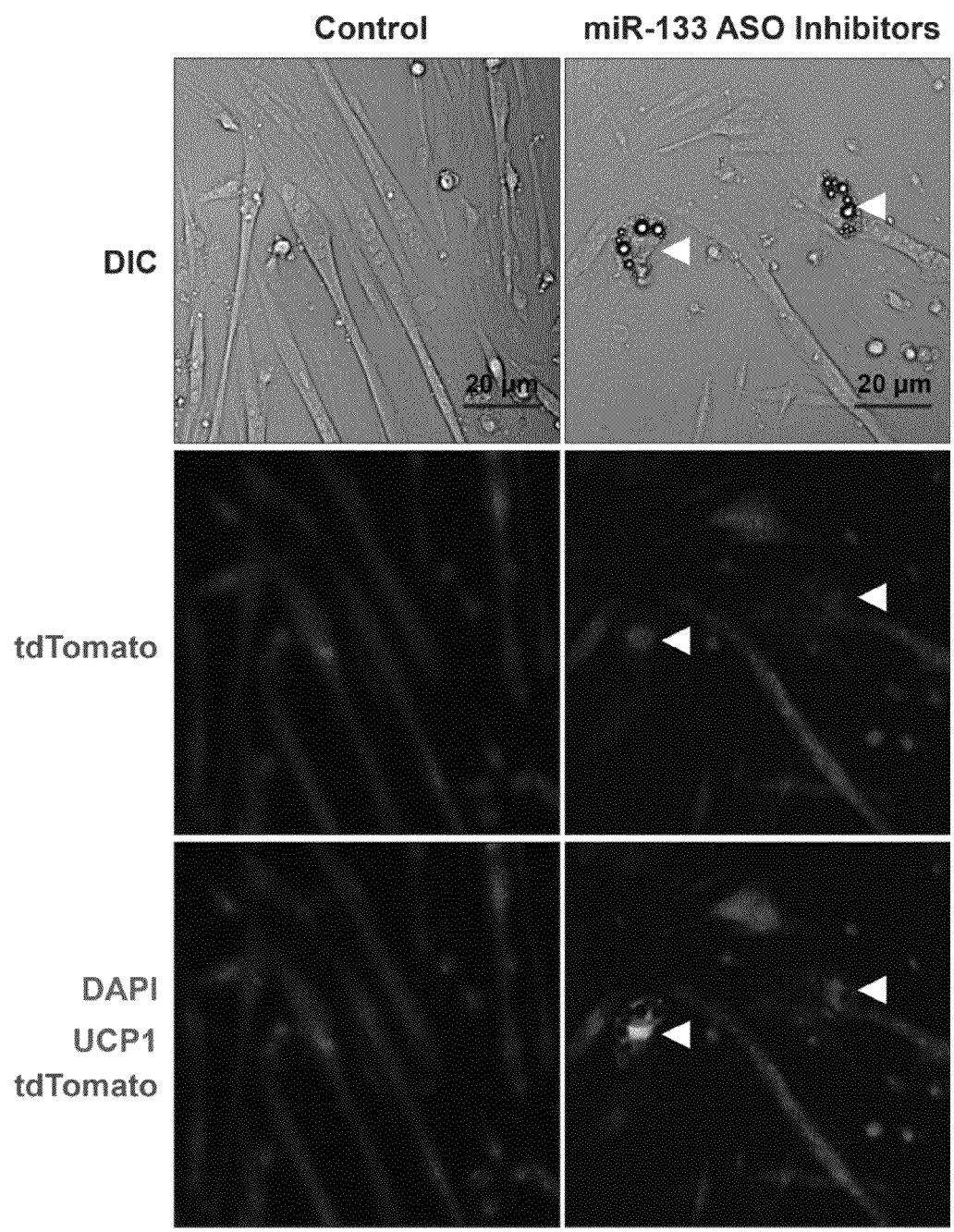
FIG. 3 shows miR-133 Prevents Brown Adipose Determination In Satellite Cells: (A) Inhibition of miR-133 induced satellite cells to differentiate into brown adipocytes (arrowheads) in myofiber cultures under pro-adipogenic conditions. Myofibers (n>300) with resident satellite cells were isolated from Pax7-CreER/R26R-tdTomato EDL muscles and transfected with mixed inhibitors for miR-133a and miR-133b or a control scramble inhibitor. Lineage marked satellite cell-derived brown adipocytes (SC_BA) expressed tdTomato and Ucp1. (B) RT-qPCR reveals gene expression signatures of SC_BAs as compared to those of myotubes and differentiated primary brown adipocytes. miR-133 inhibitor treated myofiber cultures were centrifuged to separate the supernatant faction enriched for SC_BAs and the pellet fraction which contains mostly myotubes. Error bars: S.E.M., asterisk: significant pair-wise comparison by t-test, *: p≤0.05, : p≤0.01, *: p≤0.001.

To confirm that these brown adipocytes were derived from satellite cells, tdTomato-labeled satellite cells on myofibers isolated from Pax7-CreER; R26R-tdTomato mice (>300 myofibers per treatment group) were transfected with miR-133 ASO inhibitors (FIG. 3A). Notably, Applicant observed a dramatic 16-fold increase in the number of satellite cell-derived brown adipocytes (SC_BA), as evidenced by their cytoplasmic Ucp1 and tdTomato double staining in response to miR-133 inhibition (FIG. 3A). Thus, Applicant concluded that miR-133 inhibition in satellite cells is sufficient to induce brown adipose determination.

Figure 3B:
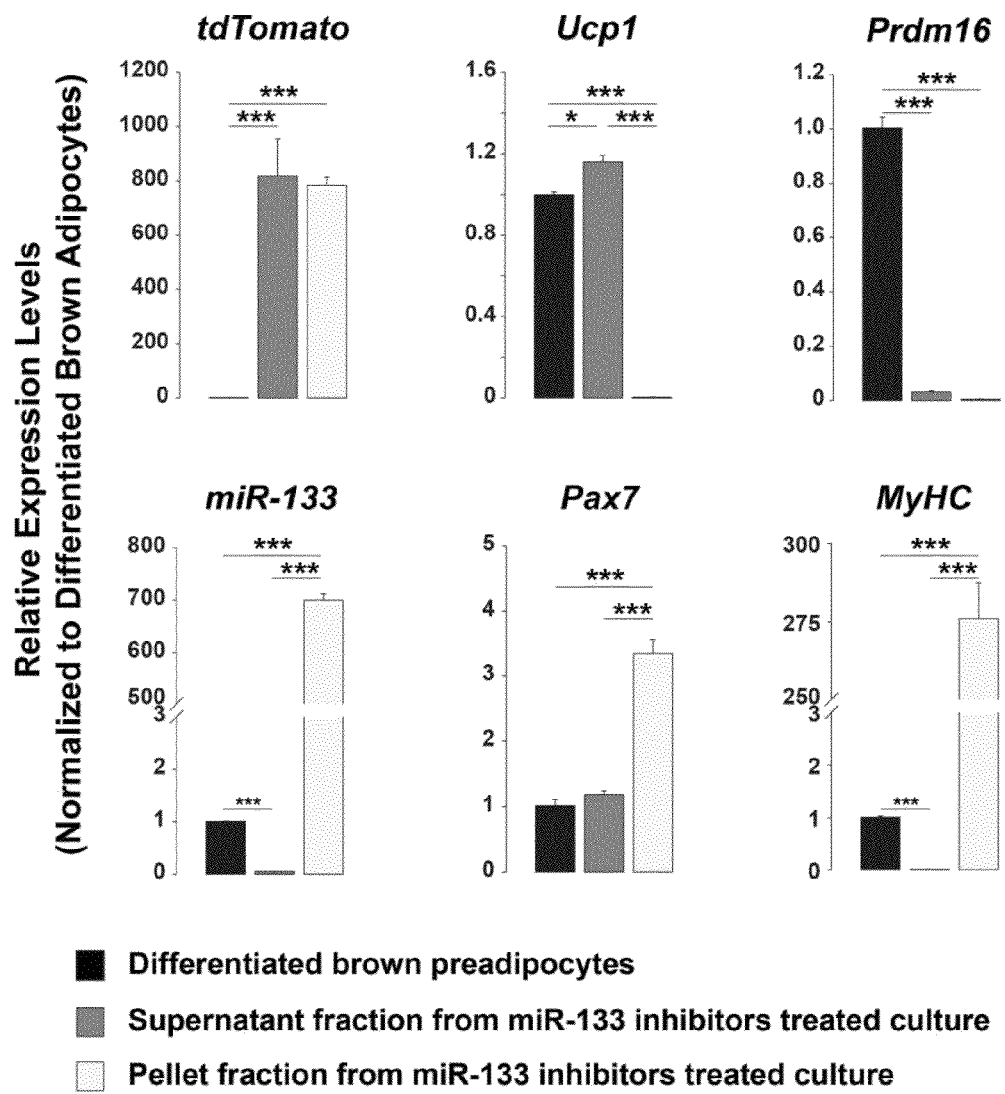

The molecular nature of SC_BA was characterized following their enrichment by centrifugation based on their low-density. After centrifugation, the supernatant fraction was enriched for SC_BA whereas the pellet fraction was enriched for myotubes. The gene expression profiles of these SC_BA and myotube fractions were then compared with those of cultured differentiated brown preadipocytes originally also isolated from Pax7-CreER; R26R-tdTomato mice (FIG. 3B). RT-qPCR revealed that the SC_BA-enriched supernatant fraction contained comparable levels of tdTomato mRNA relative to the myotube-enriched pellet fraction, consistent with the common satellite cell origin of these two types of cells. By contrast, the preadipocyte-derived brown adipocytes did not express tdTomato, confirming Pax7 was not expressed in iBAT during tamoxifen induction. Intriguingly, SC_BA expressed high level of Ucp1 but less Prdm16 relative to brown adipocytes, suggesting that a low level of Prdm16 is sufficient to support brown adipocyte determination in vitro. Consistent with miR-133 inhibitor treatment, SC_BA contained lower miR-133 levels relative to brown adipocytes. As expected, the myotube fraction was enriched for miR-133, Pax7 and MyHC yet devoid of Ucp1 mRNA. By contrast, inhibition of miR-133 in primary myoblasts was insufficient to induce brown adipogenesis, implying the existence of other inhibitory mechanisms. Taken together, these data support the hypothesis that miR-133 expression enforces myogenic commitment of satellite cells by targeting Prdm16 expression and repressing brown adipocytic determination.

Antagonism of miR-133 Induces Brown Adipose Determination of Satellite Cells During Muscle Regeneration:

To investigate miR-133 function in brown adipose determination of satellite cells in vivo, Applicant synthesized miR-133 antagomiR (miR-133 antisense oligonucleotide (ASO)) with an antisense sequence to both miR-133a and miR-133b, as well as a control "antagomiR" (control ASO) with the same chemical modifications and not antisense to any mouse gene or EST sequence (see Experimental Procedures). Applicant performed lineage tracing to distinguish effects of miR-133 ASO on satellite cells versus other cell types. Six week old Pax7-CreER; R26R-tdTomato mice were treated with tamoxifin as before (5 consecutive daily injections), then aged to 10 weeks of age prior to initiating the experiment. Control ASO versus miR-133 ASO were injected into tibialis anterior (TA) muscles 3 days following saline injection (quiescent state) or cardiotoxin injection (to induce activation). After one month, RT-qPCR was performed using RNA isolated from several tissues to evaluate the efficacy and scope of miR-133 ASO administration.

Figure 4A:
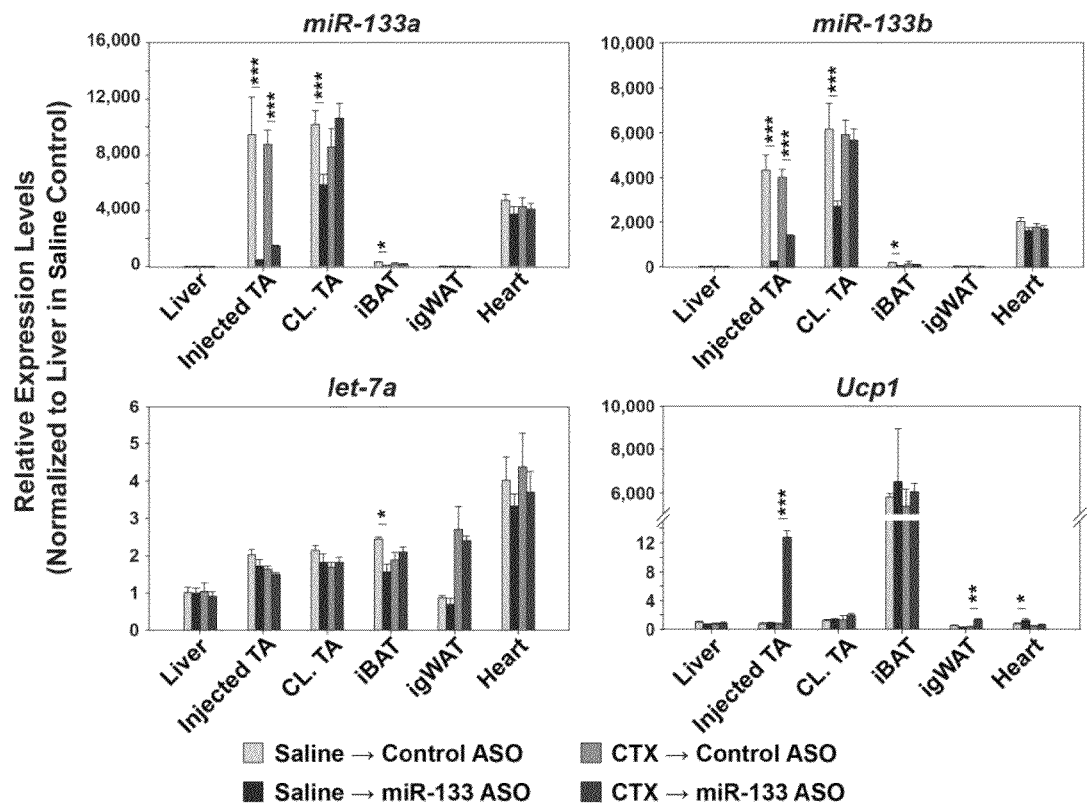
FIG. 4 shows antagonism of miR-133 Induces Brown Adipose Determination Of Satellite Cells During Muscle Regeneration: (A) High efficacy and specificity of miR-133 antagomiR (ASO) in vivo. RT-qPCR indicates reduced expression of both miR-133a and miR-133b but not let-7a in response to intramuscular miR-133 ASO administration. Ucp1 mRNA was drastically induced in regenerating TA muscles by miR-133 ASO. Error bars: S.E.M., asterisk: significant pair-wise comparison by t-test, *: p≤0.05, : p≤0.01, *: p≤0.001. (B) Immunoblots reveals the evident induction of Ucp1, but not UCP3, in regenerating TA muscles in response to miR-133 ASO treatment. Asterisk denotes the loading of the iBAT lane on the Ucp1 immunoblot was 1/100 of other lanes to avoid overloading. (C-D) miR-133 antagonism during muscle regeneration induced satellite cells to differentiate into brown adipocytes located within the muscle interstitium. Representative images of TA muscle cross-sections stained with Ucp1 and Laminin (C) or Prdm16 and Perilipin A (D) together with tdTomato native fluorescence revealed SC_BAs within the muscle interstitium.
Figure 4B:
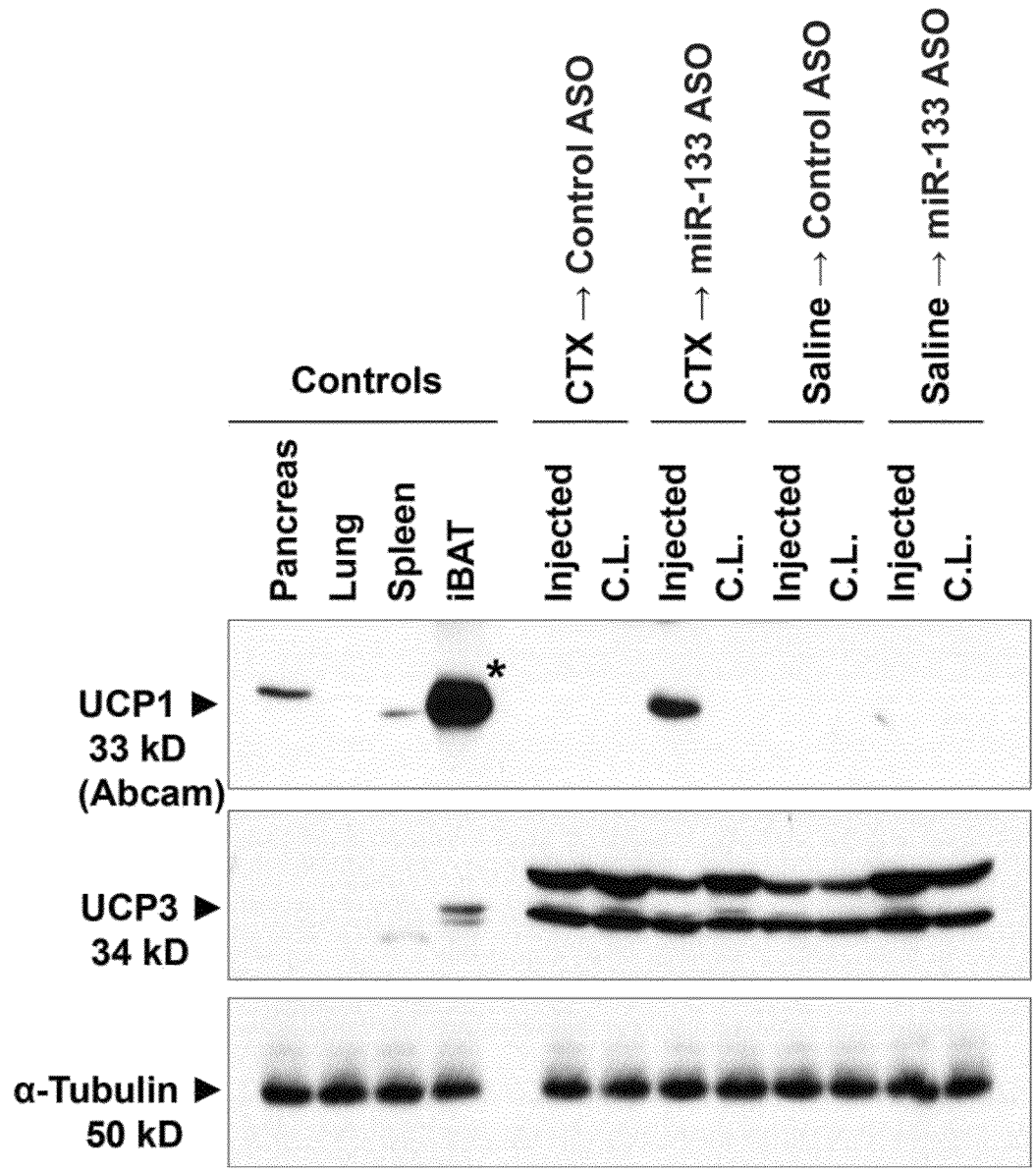

Applicant detected striking reduction of both miR-133a and miR-133b expression within the TA muscles administered with miR-133 ASO, with more prominent effects observed in resting muscles injected with miR-133 ASO (FIG. 4A). In fact, miR-133 ASO injected into resting muscles apparently also repressed miR-133a/b expression in the contralateral TA muscles, suggesting diffusion of this antagomiR under this condition. Such a "leaking" effect was not present when miR-133 ASO was injected into regenerating muscles. Notably, miR-133 expression in the myocardium was unaffected by the intramuscular administration of miR-133 ASO. In addition, miR-133 ASO had no effect on let-7a microRNA expression confirming its specificity. Accordingly, Applicant detected increased Ucp1 mRNA within miR-133 ASO injected regenerating muscle, yet not within other tissues or miR-133 ASO injected resting muscle (FIG. 4A). Similar repression of miR-133a/b and induction of Ucp1 mRNA were detected after 3 months of a single miR-133 ASO injection in regenerating muscle, indicating long-lasting effects of this ASO in muscle. Corroborating the RT-qPCR results, Ucp1 protein was specifically detected by immunoblotting of extracts from regenerated TA muscles that had received miR-133 ASO, but not in contralateral muscles or under other conditions (FIG. 4B). By comparison, Ucp3, a muscle abundant uncoupling protein, was largely unaffected by miR-133 ASO administration (FIG. 4B). miR-133 ASO treatment following frozen injury induced muscle regeneration similarly induced Ucp1 mRNA level in treated TA muscle.

Figure 4C:
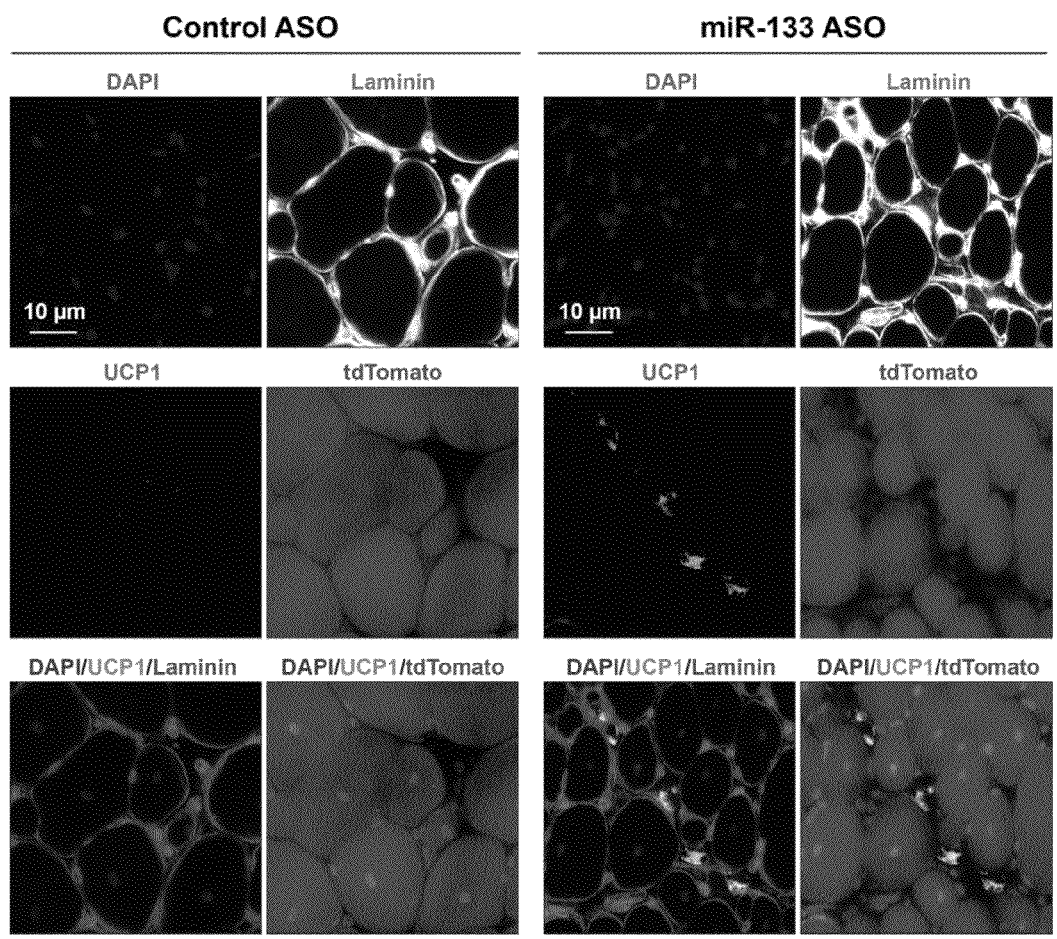
Figure 4D:
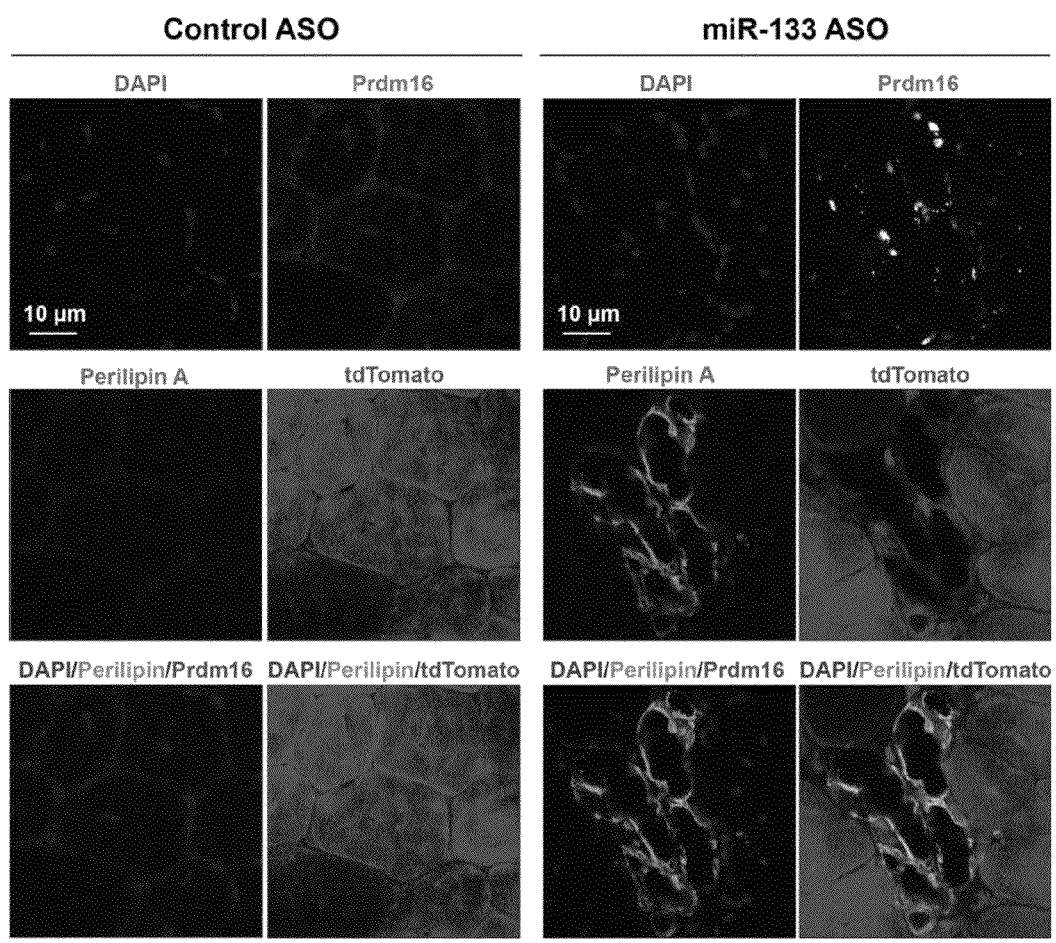

To investigate whether miR-133 ASO was inducing satellite cells to undergo brown adipose determination in vivo, Applicant performed immunofluorescence microscopy on cross-sections prepared from regenerating TA muscles treated with control- or miR-133 ASO (FIG. 4C-D) Staining for Ucp1 and basal lamina-located Laminin confirmed Ucp1 staining only within miR-133 ASO treated regenerating muscles. Moreover, Applicant found that Ucp1$^{pos}$ cells were located within muscle interstitium, distinct from surrounding myofibers ensheathed within the basal lamina (FIG. 4C). In addition, Applicant observed that these interstitial cells were immunoreactive to Perilipin A, a marker for differentiated adipocytes, and nuclear Prdm16 (FIG. 4D). Most importantly, the majority of these induced brown adipocytes were also labeled with tdTomato, indicating that they were derived from Pax7-expressing satellite cells (FIG. 4C-D).

Figure 8:
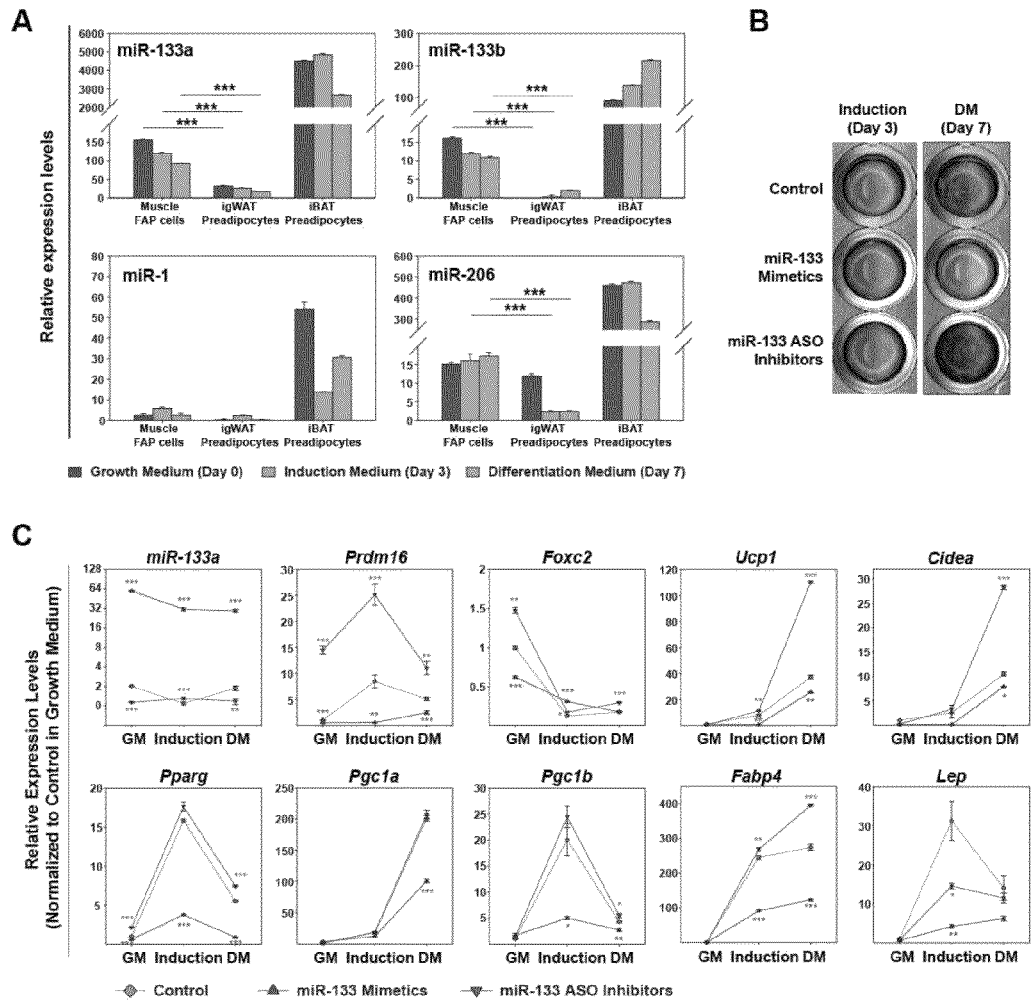
FIG. 8 shows miR-133 Regulates Brown Adipose Determination of Fibro/Adipogenic Progenitors: (A) qRT-PCR indicates that miR-133a and miR-133b were expressed in Fibro/Adipogenic Progenitors (FAPs). FACS-sorted FAPs isolated from hindlimb muscles were compared with primary white preadipocytes isolated from inguinal WAT (igWAT) and primary brown preadipocytes isolated from interscapular BAT (iBAT) under growth, adipogenic induction and adipogenic differentiation conditions. (B) ORO-staining depicts that over-expression of miR-133 impedes the adipogenic differentiation of FAPs in vitro. Shown are representative ORO-staining images of wells containing FAPs transfected with miR-133 mimetics or mixed miR-133a/b inhibitors after adipogenic induction (day 3) and differentiation (day 7). (C) qRT-PCR reveals miR-133 inhibition promoted the brown adipose determination and differentiation of FAPs in vitro. Shown are expression profiles of miR-133 and white- and brown adipogenic markers in FAPs treated with either miR-133 mimetics or miR-133 inhibitors under growth, adipogenic induction and adipogenic differentiation conditions. Error bars: S.E.M., asterisk: significant pair-wise comparison by t-test, *: $p \leq 0.05$, : $p \leq 0.01$, *: $p \leq 0.001$.

Applicant observed markedly increased numbers of interstitial cells and ORO-stained cells located between regenerating myofibers in response to miR-133 ASO treatment. ASO treated muscles contained on average 15.6 Ucp1$^{pos}$ brown adipocytes per section, of which 83.3% were derived from satellite cells. Also, each cross-section of miR-133 ASO treated muscle contained on average 31.6 Prdm16$^{pos}$ cells, of which 76.8% were derived from satellite cells. Presumably, this difference reflects the expression of Prdm16 in lineage committed yet undifferentiated brown preadipocytes. The remaining ~20% induced brown adipocytes, which were not labeled with tdTomato, possibly present either progeny of non-labeled satellite cells or of other cell sources (FIG. 8).

Figure 5A:
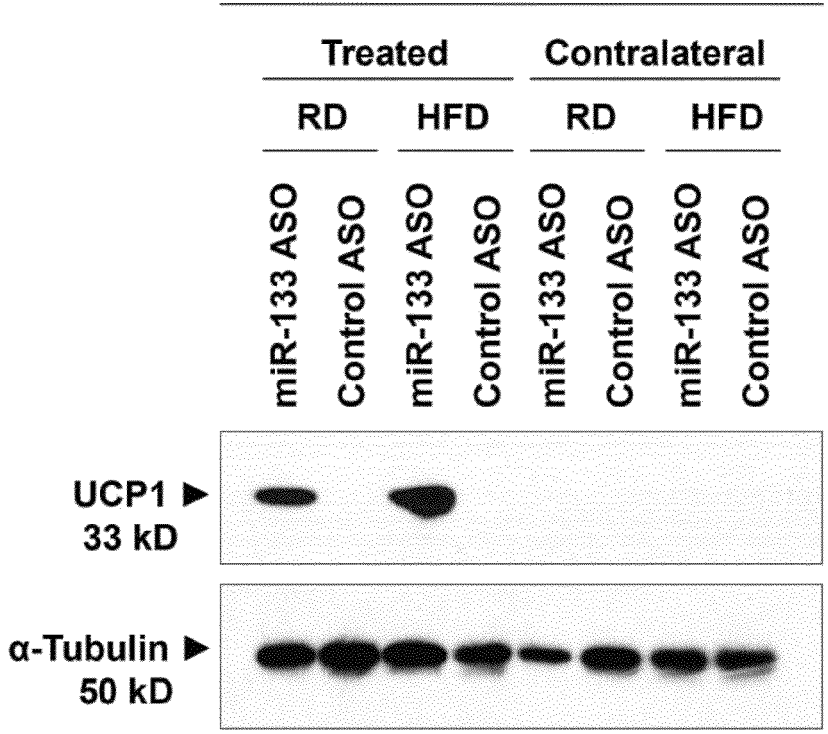
FIG. 5 shows miR-133 Antagonism Induces Metabolically Active Brown Adipocytes In Muscle. (A) Immunoblots reveals the evident induction of Ucp1 in regenerating TA muscles by miR-133 antagonism in C57BL/6 mice fed with either a regular diet (RD) or a high fat diet (HFD). The contralateral TA muscles were included as control. (B) Hematoxylin and Eosin (H/E) staining and immunohistochemistry (IHC) of Ucp1 protein reveal miR-133 antagonism induced brown adipocytes locate within the muscle interstitium (arrowheads) under both diet conditions. (C) Representative oxygraphs tracings from high-resolution respirometry depict markedly increased nonphosphorylating respiration in intact (non-permeabilized) miR-133 ASO treated TA muscles compared to control. Notably, fatty acids (FA, octanoyl carnitine) markedly increased the $O_2$ consumption in miR-133 ASO treated TA muscles compared to control. Responses before reoxygenation (which showed no $O_2$ diffusion limitation) and titration of antimycin A are shown. (D) High-resolution respirometry reveals marked increase of nonphosphorylating (uncoupled) respiration in miR-133 ASO treated TA muscles (intact cells) as well as comparable levels of FA β-oxidation mediated electron transport through electron transferring flavoprotein (ETF) and maximal oxidative phosphorylation capacity ($P_{I+II}$) in both control and miR-133 ASO treated, permeabilized TA muscles (n=6 per group). Notably, the respiration rate in control permeabilized muscle was significantly increased after titration of ADP (ETF) but remained the same in miR-133 ASO treated muscle. (E) Representative $^{18}$F-FDG microPET/CT images of miR-133 ASO treated mice depict evident increase of FDG uptake in the ASO treated TA muscle compared to the contralateral non-treated TA muscle in response to acute CL316,243 treatment. Notably, hot spots with extremely high $^{18}$F-FDG activities, presumably represent clusters of active brown adipocytes, were only present within miR-133 ASO treated TA muscles. Dashed lines denote the levels for transverse and saggital cross-sections. The position of miR-133 ASO treated TA muscle was demarcated by dots on these cross-sections. (F) Quantitative $^{18}$F-FDG activities within regions of interest (ROIs) reveal marked increase of FDG uptake in miR-133 ASO treated TA muscles after acute CL316,243 treatment (n=5 for miR-133 ASO treated group, n=4 for control ASO treated group). Applicant normalized the $^{18}$F-FDG activities within ROIs of treated TA muscles to those of contralateral TA muscles in order to cancel out potential effect of CL316, 243 on FDG uptake in differentiated muscle cells or physical activity. FDG uptake by interscapular BAT (iBAT) was also dramatically induced by CL316,243. (G) Representative thermographic images depict evident increase of surface temperatures in the miR-133 ASO treated hindlimbs of mice fed with either a regular diet (RD, arrowhead) or a high fat diet (HFD, arrowhead) compared to the contralateral hindlimbs or both hindlimbs in control ASO treated mice. Arrowheads denote ASO treated right hindlimbs. Whole-body thermographic images (lower panels) are shown to denote the representative temperatures at both hindlimbs and neck areas. (H) Quantitative temperature measurement by thermographic imaging reveal marked increase of surface temperatures in hindlimbs received miR-133 ASO treatment (n=5 per treatment group per diet group). Error bars: S.E.M., asterisk: significant pair-wise comparison by t-test, *: p≤0.05, : p≤0.01, *: p≤0.001, n.s.: not significant.
Figure 5B:
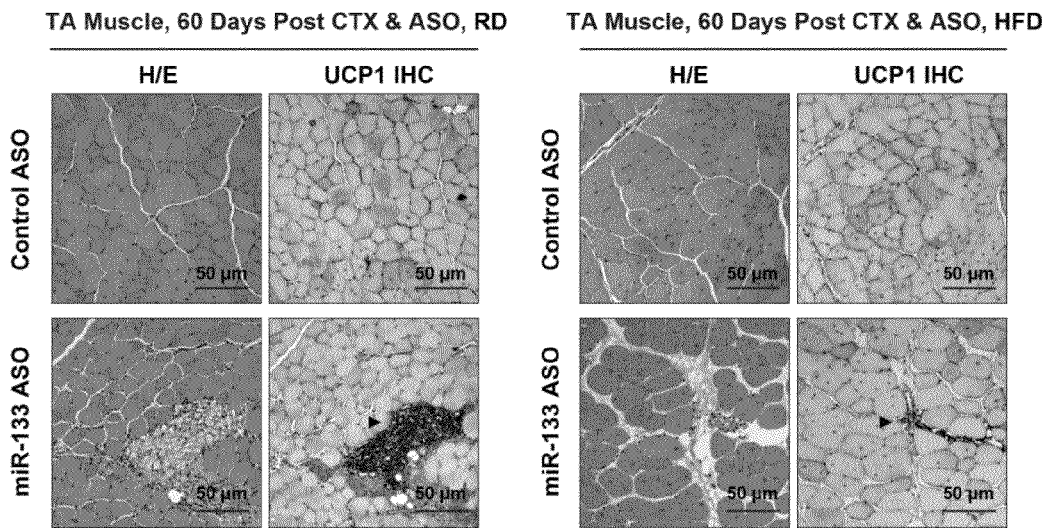
Figures 5C, 5D:
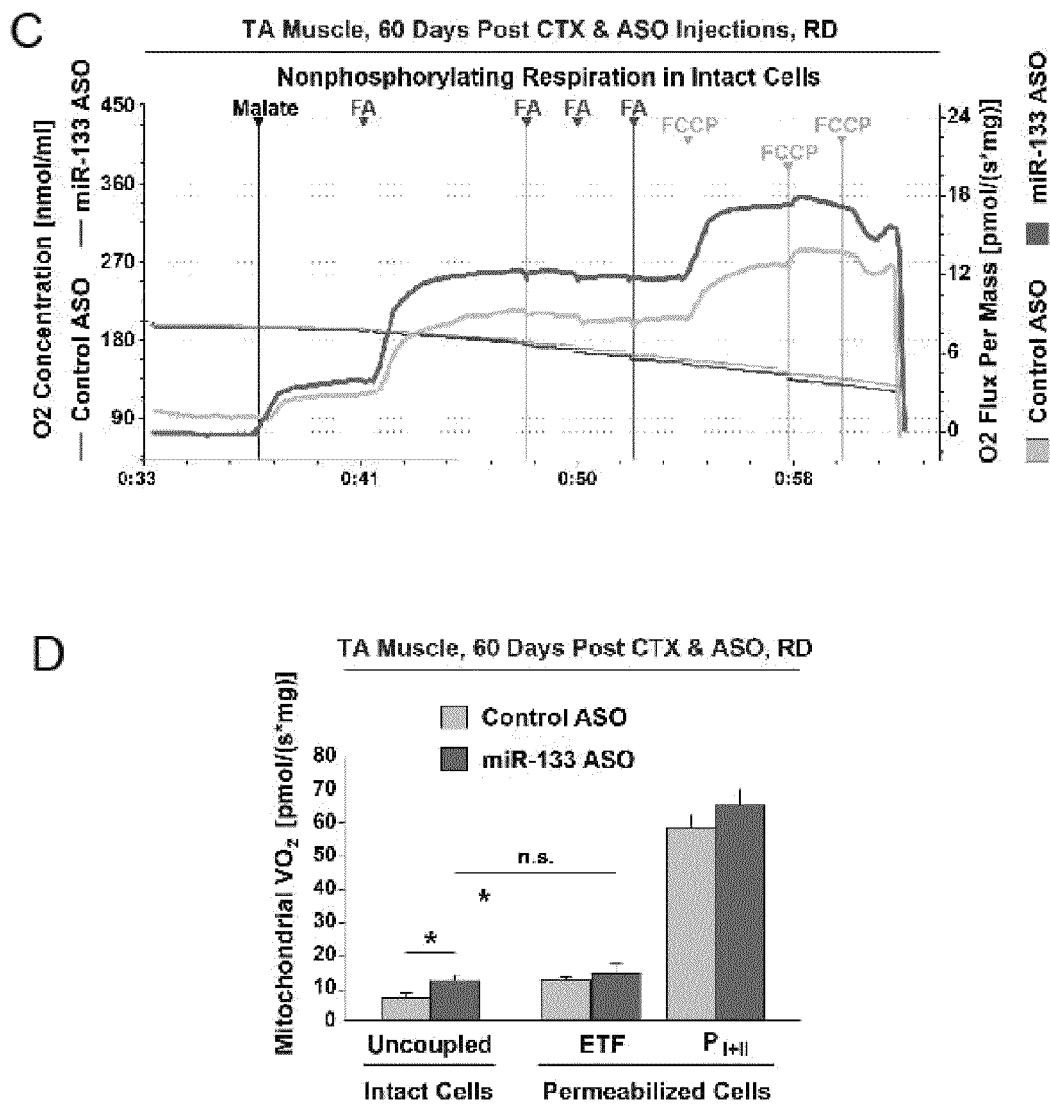

Small amounts of BAT have previously been reported to exist in hind limb muscles of obesity-resistant 129S6/SvEvTac mice, but not in obesity-prone C57BL/6 mice (Almind et al., 2007). By immunoblotting, Applicant detected ectopically induced Ucp1 protein expression in miR-133 ASO treated muscles (2 months after treatment) of C57BL/6 mice fed with either a regular diet (RD) or a high fat diet (HFD) (FIG. 5A). Consistently, Applicant did not observe Ucp1 expression in either control ASO treated muscles or contralateral resting muscles under either diet condition. H/E staining and Ucp1 immunohistochemistry further confirmed the efficacy of miR-133 ASO in inducing ectopic Ucp1$^{pos}$ brown adipocytes within muscle interstitium of C57BL/6 mice under both diet conditions (2 months after treatment) (FIG. 5B).

miR-133 Antagonism Induces Metabolically Active Brown Adipocytes In Muscle:

To quantify bioenergetic effects of miR-133 ASO induced BAT in muscle, Applicant performed high-resolution respirometry on TA muscles after 2 months of either control- or miR-133 ASO treatment (C57BL/6 male fed on RD, n=6 in each treatment group). Applicant reasoned that the study of intact muscle preparations might reveal some conspicuously higher uncoupled respiration rates due to the presence of brown adipocytes, particularly after the addition of fatty acids (FA) to the respiratory chambers (FIG. 5C). Applicant found that titration of FA (octanoyl carnitine) increased mitochondrial respiration rate to 13.5±1 pmol·sec$^{-1}$·lo$^{-1}$ in treated TA muscle compared to 7.7±1 pmol·sec$^{-1}$·ln$^{-1}$ in control (FIG. 5D, uncoupled/intact cells). This marked difference in the response to FA is consistent with reported acute activation of mitochondrial respiration rates in brown adipocytes exposed to fatty acids (Matthias et al., 2000).

To test whether this 1.75-fold higher respiration rate in miR-133 ASO treated muscle was attributed to FA-stimulated uncoupling in brown adipocytes, Applicant permeabilized a separate bundle of TA muscle to allow FA to quickly enter all cell types (see Procedures) and measured FA β-oxidation mediated electron transport through electron transferring flavoprotein (ETF) in a separate portion of the TA muscles after permeabilization (which allows various substrates to pass through the cell membrane; Procedures). In response to ADP to induce state-3 respiration mediated by ETF, the respiration rate increased to 13.0±1 pmol·sec$^{-1}$·le$^{-1}$ in the control, but was unchanged in the treated muscles (FIG. 5D, ETF/permeabilized cells). This response strongly supports the hypothesis that the higher respiration rate with FA supply in intact (non-permeabilized) cells was due to rapid FA uptake and uncoupling, which is characteristic of brown adipocytes. By calculation, Applicant predicted that the induction of uncoupling respiration by miR-133 ASO leads to additional 0.3 cal·hour$^{-1}$·mg$^{-1}$ of energy expenditure in the treated TA muscle.

To test whether miR-133 ASO also has bioenergetic effects on differentiated muscle cells, Applicant compared coupled state-3 respiration rates in treated and control permeabilized muscles under full electron supply through complexes I and II (FIG. 5D, permeabilized cells). No difference in electron transport through complex I (NADH dehydrogenase) between control and treated muscles was observed after electron transport through ETF (FA respiration) is inhibited by the titration of glutamate (treated=33±3 pmol·sec$^{-1}$·lo$^{-1}$, control=28±2 pmol·sec$^{-1}$·lc$^{-1}$, p=0.2). Maximal cellular state 3 respiration or oxidative phosphorylation capacity (P I+II) was induced with the addition of succinate to provide additional electron flow through complex II (succinate dehydrogenase), probing the maximal mitochondrial capacity to catalyze Redox reactions that are primarily coupled to the production of ATP via ATP synthase. Again, no difference in state 3 respiration rates with complex I+II substrates was observed, indicating comparable maximal coupled respiration between control- and miR-133 ASO treated muscles (FIG. 5D, P$_{I+II}$/permeabilized cells) Similar results were derived from contralateral soleus muscles of control- or miR-133 ASO treated mice, thus ruling out a systematic effect of miR-133 ASO on muscle groups outside of the treated limb.

Altogether, these data support the assertion that miR-133 ASO treatment in regenerating muscle results in unaltered coupled respiration in treated muscle but elicits drastic increases in uncoupled respiration, presumably owing to ectopically induced brown adipocytes within interstitium.

Metabolically active BAT has been identified in adult human by [$^{18}$F]-fluorodeoxyglucose positron emission tomography ([$^{18}$F]-FDG PET), due to dramatic glucose uptake by this tissue after sympathetic activation (Nedergaard et al., 2007). To visualize active brown adipose tissue within muscle, Applicant performed [$^{18}$F]-FDG PET imaging on control- or miR-133 ASO treated mice (n=5 for 133 ASO treated mice, n=4 for control treated muscle; 2 months after treatment) after acute sympathetic activation by selective β3-adrenergic receptor agonist, CL316,243 (FIG. 5E). Applicant observed a dramatic increase of FDG uptake in miR-133 ASO treated TA muscles compared to contralateral TA muscles or TA muscles within control ASO treated mice. To rule out possible direct and indirect effects of CL316,243 on glucose/FDG uptake by skeletal muscle cells, Applicant normalized FDG activities derived from ROIs of treated TA muscles to those of contralateral TA muscles (FIG. 5F). On average, miR-133 ASO treated TA muscles after CL316,243-stimulated sympathetic activation exhibited a 1.3-fold increase of glucose/FDG uptake compared to control, strongly arguing that the ectopic induced brown adipocytes in miR-133 ASO treated TA muscles are metabolically active. Such a drastic increase was not observed without the sympathetic activation preceding anesthesia (baseline). As a reference, glucose/FDG uptake by interscapular BAT expectedly increased 2.3~2.5 fold after CL316,243-stimulated sympathetic activation in both control- and miR-133 ASO treated mice (FIG. 5F).

A hallmark of active brown adipocytes is their unique thermogenic capability via extensive uncoupled respiration in abundant mitochondria (Cannon and Nedergaard, 2004). Therefore, Applicant directly assessed the thermogenic capability of muscle-embedded brown adipocytes by thermographic imaging of control- or miR-133 ASO treated mice fed with either RD or HFD (n=5 per treatment group per diet group; FIG. 5G). Applicant observed evident increased surface temperatures on miR-133 ASO treated hindlimbs compared to contralateral hindlimbs or hindlimbs within control ASO treated mice (FIG. 5G). On average, the surface temperatures on miR-133 ASO treated hindlimbs were 0.7° C. or 0.9° C. higher than control hindlimbs for mice fed with RD or HFD, respectively (FIG. 5H). Applicant observed no difference in expression of IL-1β and TNF-α between control- and treated muscles supporting the assertion that the temperature increase is not due to inflammation.

Taken together, Applicant's data provides compelling evidence that the induced intramuscular BAT induced by miR-133 ASO treatment is metabolically active.

Antagonism of miR-133 during Muscle Regeneration Reduced Adiposity, Augmented Energy Expenditure and Improved Glucose Tolerance:

Intramuscular brown adipocytes have been described in 129S6/SvEvTac mice and in Lxr$^{-/-}$ mice (deficient for Liver X receptors), both of which display increased energy expenditure and resistance to obesity (Almind et al., 2007; Kalaany et al., 2005). Applicant therefore assessed systematic metabolic consequence of miR-133 ASO treatment in regenerating TA muscle.

Treated and control C57BL/6 male mice were raised on either RD or HFD in individual cages at 22° C. (n=5 per treatment per diet group). In both diet groups, miR-133 ASO treated mice were obviously leaner than the control mice at 4-month after treatment (FIG. 6A). Quantitatively, miR-133 ASO treated mice displayed reduced gain in body weight over the 4-month period after ASO administration (FIG. 6B). Close examination revealed significant reduction of igWAT and epiWAT weights, yet the mass of iBAT depots and treated TA muscles were unaffected (FIG. 7A).

To assess whether miR-133 ASO treatment leads to increased whole-body energy expenditure, Applicant carried out indirect calorimetry studies at 2-3 months after ASO treatment on control- and miR-133 ASO treated mice (C57BL/6, male, individually caged, n=5 per treatment group per diet group; FIGS. 6C & 7B). Applicant detected significant increase of total energy expenditure in miR-133 ASO treated mice during light cycle (FIG. 6C, left) without change in physical activities (FIG. 6D, left). Intriguingly, this amount of energy expenditure is coincident with the increase of mitochondrial respirometry-measured energy expenditure in miR-133 ASO treated TA muscles after adjustment with TA muscle mass (FIG. 7A; 0.3 cal·hour$^{-1}$·le$^{-1}$×75 mg=0.0225 kcal·hour$^{-1}$). Thus, Applicant reasoned that increased uncoupled respiration due to ectopically induced intramuscular BAT likely underlies ~90% of total energy expenditure increase in light cycle. In dark cycle (when mice are active and feeding), the energy expenditure is conspicuously high in miR-133 ASO treated mice (FIG. 6C, right), which is associated with increased physical activities for the mice during the dark cycle (FIG. 6D, right).

Figure 6E:
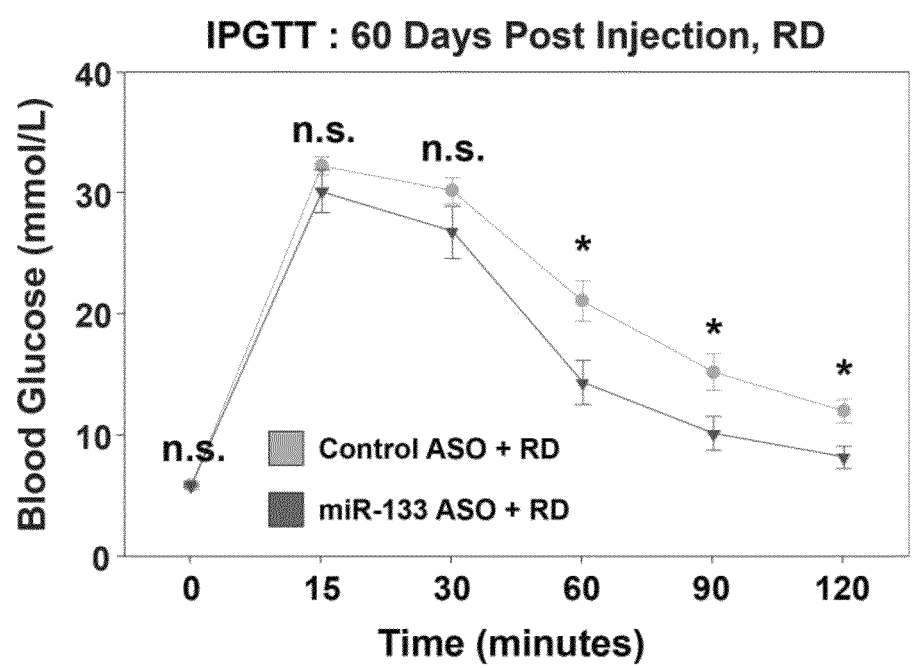
FIG. 6 shows Antagonism of miR-133 During Muscle Regeneration Reduced Adiposity, Increased Total Energy Expenditure And Improved Glucose Tolerance. (A) Representative images of direct comparisons of C57BL/6 mice fed the RD or HFD and received control- or miR-133 ASO treatment during TA muscle regeneration depicts the miR-133 ASO treated mice displayed leaner phenotype. (B) Retarded body weight increase over a 16-week body weight monitoring time course in mice received miR-133 ASO treatment during TA muscle regeneration (n=6 per treatment group per diet group). (C) miR-133 ASO treatment increased total energy expenditure. Indirect calorimetry reveals that mice received miR-133 ASO treatment during TA muscle regeneration recorded higher energy expenditure than the control mice (n=5 per group), measured at 22° C. during light and dark cycles (fed the RD). Values of total energy expenditure were plotted without normalization to lean body mass. (D) Physical activities measured within light and dark cycles during indirect calorimetry (C) reveal increased physical activities within the dark cycle for miR-133 ASO treated mice (fed the RD). Physical activities are presented as arithmetic means of beam breaking events at X-, Y- and Z-dimensions. (E) IPGTT tests for C57BL/6 mice received either control- or miR-133 ASO treatment (fed the RD; n=6 per group). Error bars: S.E.M., asterisk: significant pair-wise comparison by t-test, *: p≤0.05, : p≤0.01, *: p≤0.001, n.s.: not significant.

Similarly, Applicant detected significantly increased total energy expenditure in miR-133 ASO treated mice fed the HFD during the light cycle (FIG. 7B, left) without difference in physical activities (FIG. 7C, left). No significant increase in energy expenditure or physical activity was recorded in these mice over the dark cycle when compared to control mice (FIGS. 7B & 7C, right panels). This discrepancy may be related to the abnormally low respiratory exchange ratio (~0.76) in the control mice fed with HFD (FIG. 7D), which indicates an increased proportion of lipid oxidation in the control mice. The 24-hour food intake in miR-133 ASO treated mice was comparable to that of control mice for both diet groups (FIG. 7E), suggesting the reduction of body weight is likely due to the enhanced thermogenesis, and hence lower food efficiency in the mice. In addition, miR-133 ASO treatment also led to much improved glucose tolerance in both diet groups (FIGS. 6E & 7F). Notably, H/E staining and microscopy of tissue sections from fat depots and liver revealed that miR-133 ASO treated mice exhibited reduced numbers of infiltrating inflammatory cells in the epididymal white fat depots and reduced steatosis of the liver of mice fed the HFD (FIG. 7G).

Therefore, Applicant concluded that miR-133 antagonism by ASO injection during muscle regeneration elicits profound changes in energy metabolism at the whole body level, consistent with a leaner and healthier phenotype.

Figure 7:
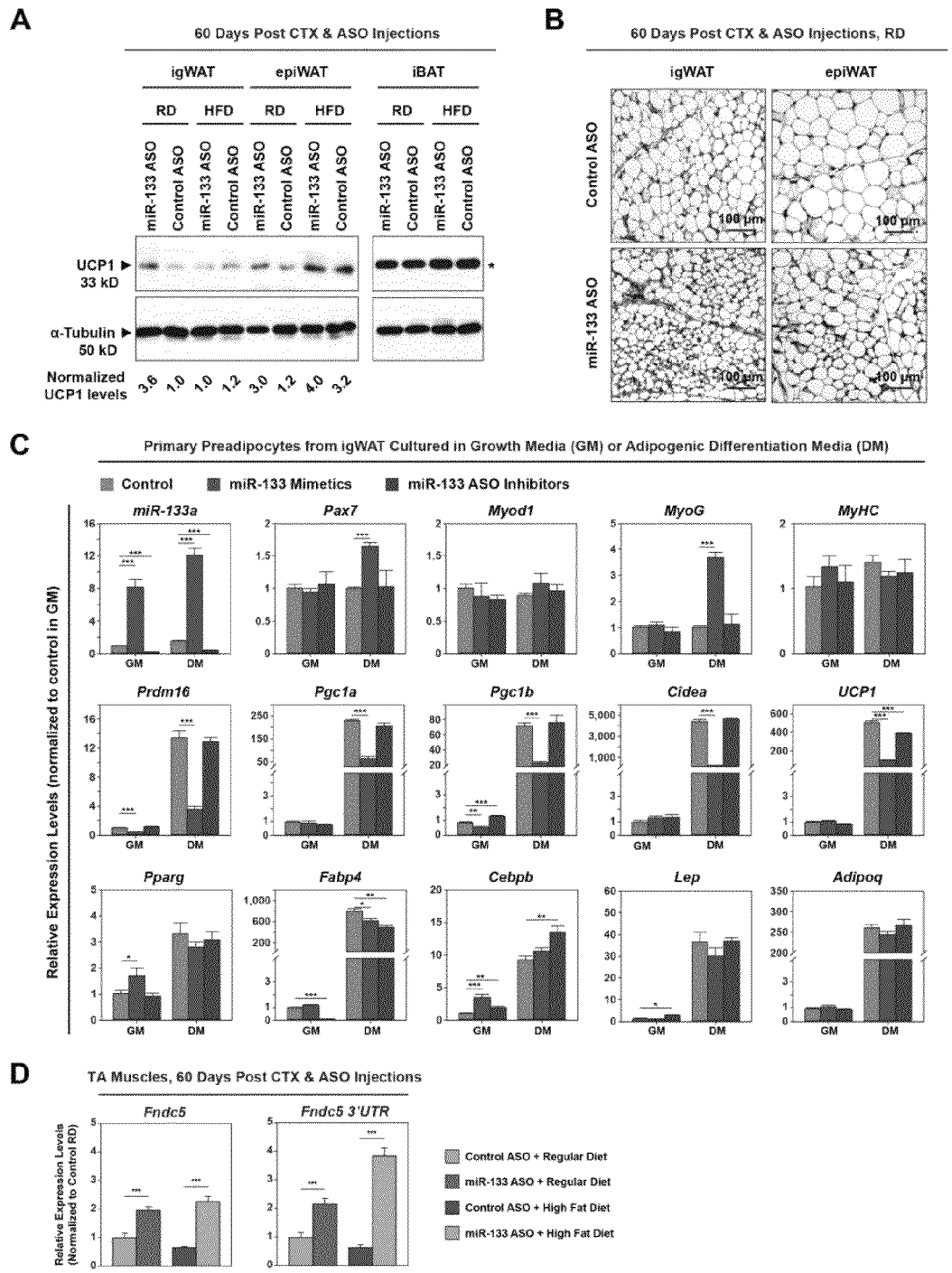
FIG. 7 shows miR-133 Antagonism Indirectly Promotes the Emergence of Beige Adipocytes within White Adipose Tissues: (A) Immunoblots reveals the increase of UCP1 in inguinal and epididymal white adipose tissues in response to CTX and miR-133 antagonism in C57BL/6 mice fed with a regular diet (RD). Notably, such an effect of miR-133 antagonism was not present in C57BL/6 mice fed with a high fat diet (HFD). Normalized UCP1 levels were calculated based on the densitometry analysis of the UCP1 immunoblot and the α-Tubulin immunoblot. The interscapular brown adipose tissue (iBAT) were included as a control. Asterisk denotes the loading of the iBAT lanes on the UCP1 immunoblot was 1/100 of other lanes to avoid overloading. (B) Immunohistochemistry (IHC) of UCP1 protein reveal miR-133 antagonism induced beige adipocytes within inguinal and epididymal white adipose tissues. (C) qRT-PCR reveals lentiviral overexpression of miR-133 repressed the expression of brown adipogenic markers (Prdm16, Pgc1a, Pgc1b, Cidea and Ucp1) in primary white preadipocytes isolated from inguinal white adipose tissues. Distinct from primary brown preadipocytes, inhibition of miR-133 by antisense oligos did not elicit brown adipogenic commitment in primary white preadipocytes. Notably, impaired brown adipogenic commitment in the miR-133 ov. culture was companied only with mediocre increase of two myogenic commitment/differentiation markers (Pax7, Myogenin). (D) qRT-PCR reveals the expression of Fndc5 (the precursor gene for muscle-released hormone Irisin) was increased in miR-133 ASO treated muscles as compared to control muscles under both RD and HFD conditions. Error bars: S.E.M., asterisk: significant pair-wise comparison by t-test, *: $p \leq 0.05$, : $p \leq 0.01$, *: $p \leq 0.001$.

Prdm16 acts as a "master regulator" to control BAT lineage determination (Seale et al., 2008). Applicant has identified a microRNA expressed in satellite cells, and upregulated as the myogenic program progresses—miR-133—that directly represses the expression of Prdm16 to enforce myogenic commitment Inhibition of miR-133 function in satellite cells or adipogenic progenitors in muscle (FAPs) results in upregulation of Prdm16 and brown adipose determination (FIGS. 3-5 and 8). By contrast, over-expression of miR-133 in brown preadipocytes markedly inhibits brown adipose differentiation and induces muscle-specific genes (FIG. 7). In all, these data support a central role of miR-133 in the regulation of brown adipose determination by directly modulating Prdm16 expression.

Here, Applicant has shown that satellite cells can differentiate into either myocytes or brown adipocytes. In addition, Applicant has demonstrated that miR-133 regulates a lineage switch between myogenic and brown adipogenic commitment. Functional brown adipocytes are efficiently induced from satellite cells by inhibiting miR-133 function during muscle regeneration. Therefore, targeting miR-133 activity in adult muscle stem cells represents an attractive strategy to stimulate a physiological effective increase in the numbers of active brown adipocytes in vivo.

miR-133 Regulates Brown Adipose Determination of Fibro/Adipogenic Progenitors:

The observation that ~20% of induced brown adipocytes were not derived from satellite cells suggested the involvement of other types of cells within miR-133 ASO treated muscles. For example, mesenchymal progenitor cells of adipogenic differentiation potential have been shown to reside within murine and human skeletal muscles (Crisan et al., 2008; Joe et al., 2010; Pisani et al., 2010; Schulz et al., 2011; Uezumi et al., 2010). Of particular interest, muscle-resident fibro/adipogenic progenitor cells (FAPs) are capable of differentiation into white adipocytes both in vitro and in vivo (Joe et al., 2010).

Applicant characterized expression profiles of miR-133a, miR-133b, miR-1 and miR-206 in cultured FAPs isolated from hind limb muscle and compared to those of preadipocytes isolated from inguinal white fat depots (igWAT) and iBAT, through adipogenic differentiation (day 0 in growth media, day 3 in adipogenic induction media, day 7 in adipogenic differentiation media) (FIG. 8A). All four myomiRS were relatively abundant in brown preadipocytes as opposed to FAPs and igWAT preadipocytes, supporting previous findings that preadipocytes from BAT express these myomiRS (Walden et al., 2009).

Intriguingly, miR-133a and miR-133b, but not miR-1 or miR-206, were relatively enriched in FAPs as compared to igWAT preadipocytes. Applicant hypothesized that this elevated expression of miR-133 in FAPs prevents the brown adipose determination both in vitro and in vivo. Applicant therefore transfected FAPs with either miR-133 mimetics or miR-133 inhibitors before adipogenic induction and differentiation (FIG. 8B). ORO staining at day 7 of differentiation revealed that miR-133 over-expression drastically impeded the adipogenic differentiation of FAPs, whereas miR-133 inhibition slightly increased it.

Applicant further profiled the expression of miR-133 along with markers specific to brown- or white adipocytes, and markers common to both, in response to miR-133 inhibition and over-expression (FIG. 8C). In proliferating FAPs, the expression level of Prdm16 was increased about 15-fold with miR-133 inhibition. By contrast, Foxc2, a gene that induces the BAT phenotype when overexpressed in WAT (Cederberg et al., 2001), was increased 1.5-fold after miR-133 inhibition, and modestly decreased after miR-133 over-expression Importantly, miR-133 inhibition led to significant increases in the expression levels of the brown adipocyte-specific genes, Ucp1 and Cidea, after adipogenic differentiation. In addition, BAT induction by miR-133 inhibition did not alter Pparg, Pgc1α or Pgc1β mRNA levels. By contrast, miR-133 over-expression resulted in dramatic reduction of these adipogenic transcription factors critical for both brown- and white adipogenesis. In agreement, miR-133 over-expression also blunted the expression of Fabp4 and Leptin, supporting the notion that the white adipogenesis was abrogated. Conversely, miR-133 inhibition evidently increased Fabp4 expression yet decreased the Leptin expression in differentiated adipocytes. Therefore, in a similar manner to satellite cells, Applicant concluded that miR-133 regulates brown adipose determination of FAP cells.

Reporter Assay can be Used to Identify Inhibitors and Activators (or Mimetics) of miR-133:

In order to be able to rapidly test designed miR-133 oligonucleotide-based inhibitors and search for small molecule-based inhibitors effective in a relevant cellular context by high-throughput screening, the Applicant has designed, generated and tested a simple yet robust system that can transform quantitative levels of miR-133 functionality in live cells into machine-readable signals.

Figures 9A, 9B:
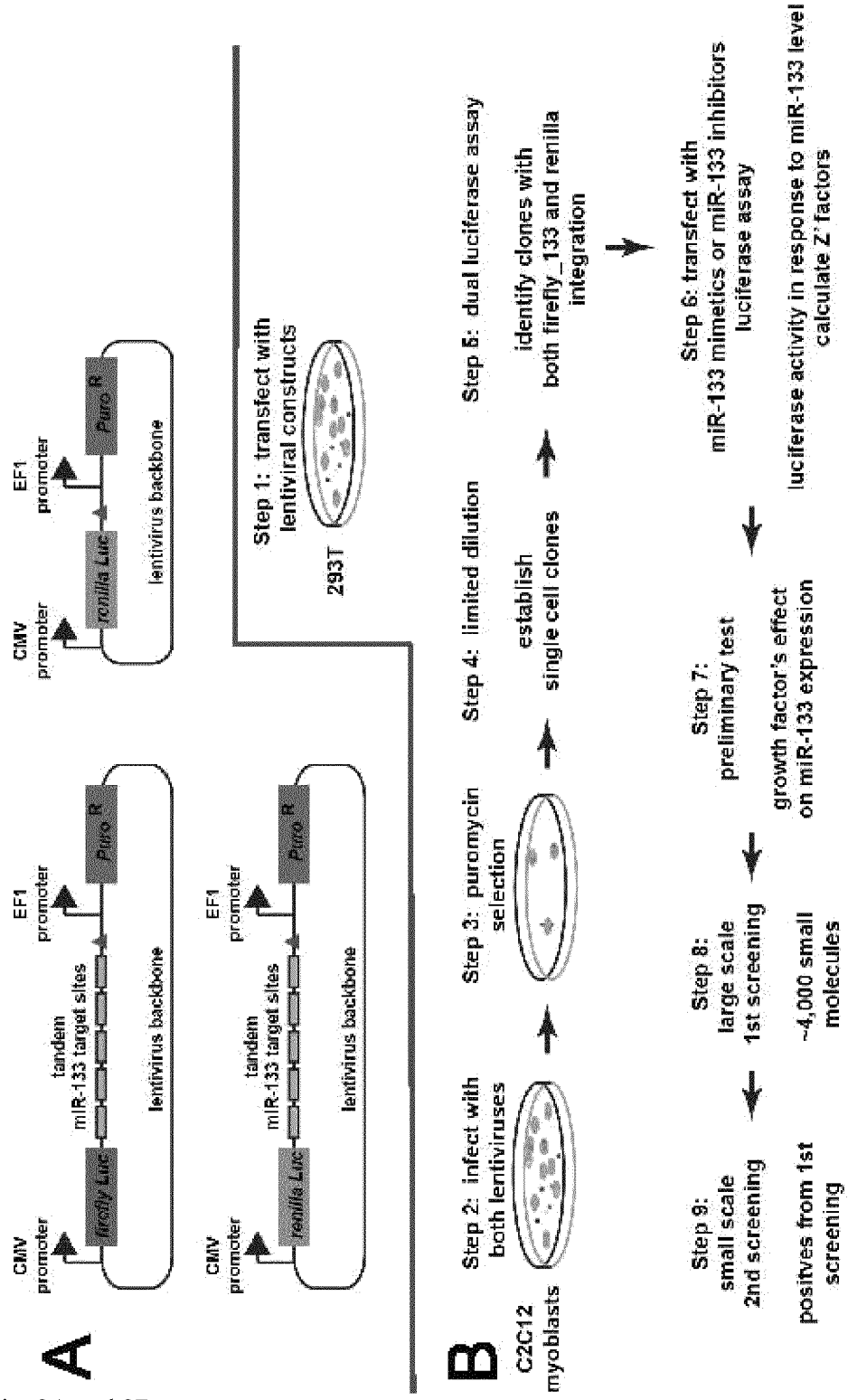
FIG. 9 shows the design and testing of a biosensor assay for miR-133 modulators. (A) Schematic representation of 2 biosensor plasmids—pCMV-FireflyLuc__miR133TS_EF1_Puro and pCMV-RenillaLuc__133TS_EF1_Puro. Both luciferase reporters were constructed on a lentivirus backbone containing a puromycin resistance gene for stable expression clone selection. Five tandem miR-133 target sites (miR133TS; 5'-TAGCTGGTTGCCAGGACCAAAA-3', SEQ ID NO:22) serving as an artificial 3'UTR to the luciferase transcript. (B) Schematic representation of the steps involved in performing the biosensor assay. (C) Testing of different clones show that assay is responsive to known miR-133 mimetics and miR-133 inhibitors. (D) Small molecule screening of a test library identifies modulators of miR-133 activity.

The design of the miR-133 biosensor is based on the principle that recognition of microRNA target sites in 3'UTR by microRNA/RISC leads to the inhibition of the translation of the target mRNAs. An artificial 3'UTR containing optimized miR-133 target sites in tandem was designed and cloned downstream of the open reading frames of firefly luciferases and GFP, which in together function as miR-133 biosensor (FIG. 9A), in a lentiviral vector. C2C12 myoblast clones were infected with lentiviruses carrying the miR-133 biosensor and selected for stable expression of the reporter construct. Activity of potential modulators or miR-133 is tested and read as a reverse correlation between miR-133 functionality and luciferase/GFP intensities. The construct can be used for live-cell imaging (in vitro and in vivo) and allows real-time detection. A schematic representation of the steps involved in performing the biosensor assay is shown in FIG. 9B.

Figure 9C:
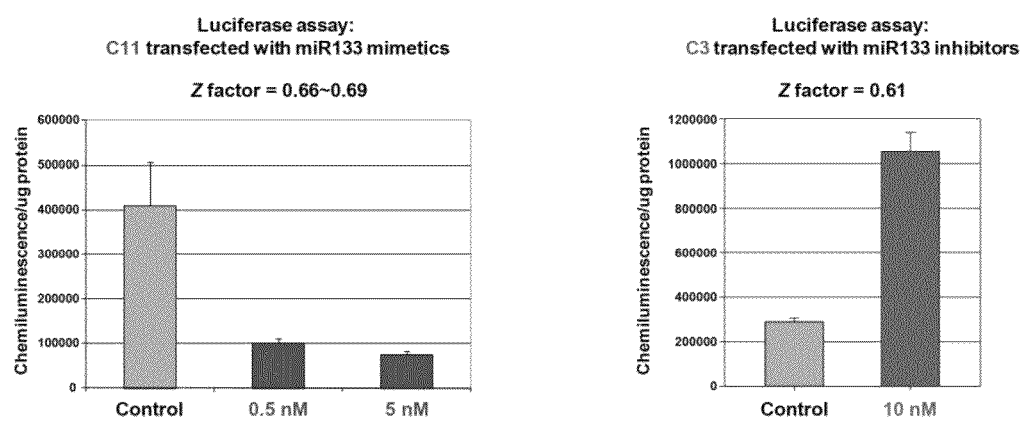
Figure 9D:
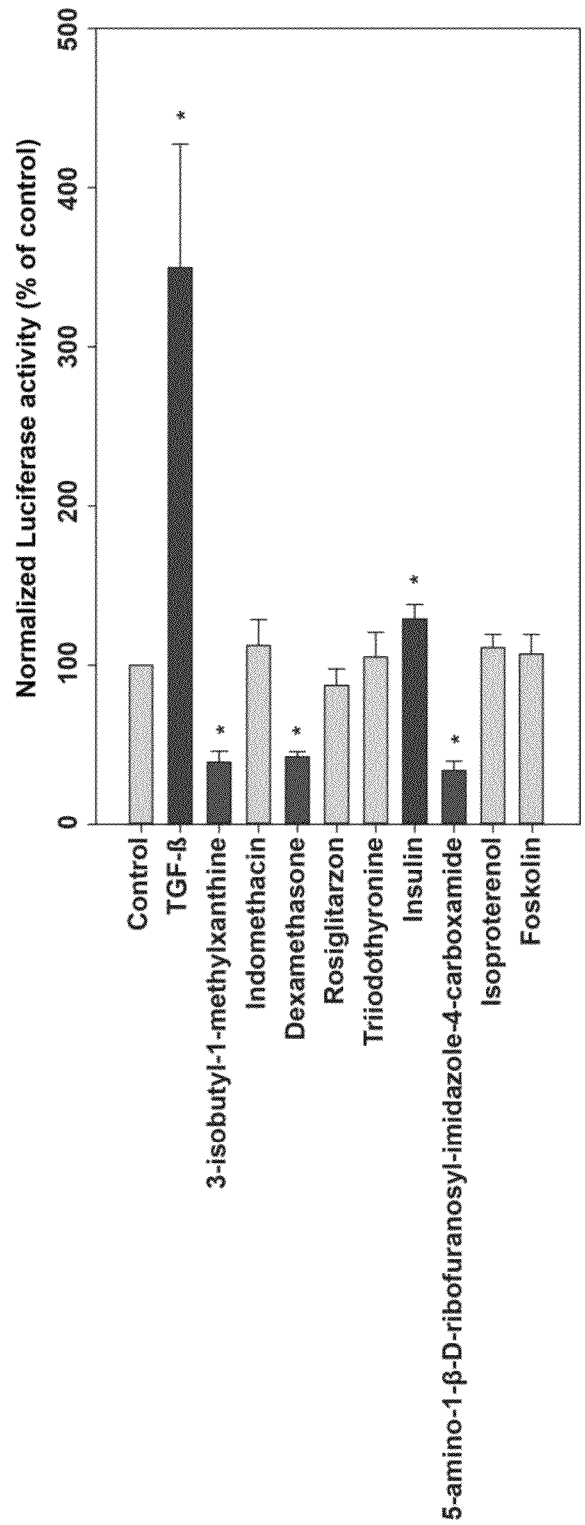

The Applicants have tested the biosensor assay with mimetics and inhibitors of miR-133 (both oligo-based and small-molecule-based) and shown that the system is sensitive and adequate to identify and quantify the activity of both inhibitors and activators (FIG. 9C). Screening of a test small molecule library demonstrates that modulators of miR-133 can be identified by high-throughput screening using the biosensor assay (FIG. 9D).

Procedures

Animals:

All animal procedures conform with the Canadian Council on Animal Care's Guide to the Care and Use of Experimental Animals, the Animals for Research Act, and were approved by the Animal Care Committee at University of Ottawa. Individual caged C57BL/6 male mice were purchased from Charles River. All other mice were maintained on a C57BL/6 background. The following mice were used in this study: Pax7-CreER/+ mice (Nishijo et al., 2009) (a kind gift from Dr. Charles Keller), Gt(ROSA)26Sortm9(CAG-tdTomato)$^{Hze}$ mice (Jackson laboratory), Pax7-ZsGreen mice (Bosnakovski et al., 2008) (a kind gift from Dr. Michael Kyba), Myf5-Cre/+ mice (Tallquist et al., 2000). To induce Cre expression from Pax7-CreER locus, 200 μL Tamoxifen/corn oil solution (20 mg/mL) was intraperitoneally injected into 6-week-old mice for consecutive 5 days.

Myofiber Isolation and Culture:

Single myofibers were isolated from extensor digitorum longus (EDL) muscles of 8~10 weeks old mice as previously described (Kuang et al., 2007). Myofibers were cultured in Dulbecco's modified eagle medium (DMEM) supplemented with 4.5 g/L glucose, L-glutamine, sodium pyruvate, 20% FBS and 1% chicken embryo extract without Penicillin or Streptomycin.

Induce Brown Adipocytes In Vivo:

To induce brown adipocytes in vivo, 10 mg/mL Cardiotoxin solution (50 μl) was intramuscularly injected into TA muscles of 10-week old Pax7-CreER/R26R-tdTomato mice (FIG. 4) or C57BL/6 mice (FIG. 5 and FIG. 6). Alternatively, frozen injury was performed by applying liquid nitrogen cooled tweezers tips directly onto the anterior sides of TA muscles. After 3 days, 20 μg of miR-133 antagomiR or control antagomiR in saline (50 μl) was intramuscularly injected into the same injured TA muscles (on right hindlimbs). To test efficacy of miR-133 ASO in intact muscles, saline, instead of Cardiotoxin, was injected to TA muscles before miR-133 ASO administration (FIGS. 4A, 4B). miR-133 antagomiR and scramble antagomiR were designed as previously described (Krutzfeldt et al., 2005).

miR-133 antagomiR sequence and modifications (shown 5' to 3):

*mA*mUmAmGmCmUmGmGmUmUmGmAmAmGm-GmGmGmAmC*mC*mA*mA*mAChl

Scramble antagomiR sequence and modifications (shown 5' to 3):

*mA*mAmGmAmAmUmGmAmCmGmAmUmCmGm-GmUmAmGmG*mG*mC*mA*mCChl

'm' represents a 2'-O-methyl-modified nucleotide. '*' indicates a phosphorothioate linkage 'Chl' denotes a 3' cholesterol moiety.

Fluorescence Activated Cell Sorting (FACS):

FACS analysis and sorting were performed on a MoFlo High Speed Sorter (DAKO-Cytomation) equipped with 488 mu, 633 nm and UV lasers. Primary brown preadipocytes were FACS-sorted from interscapular BAT of neonatal mice as previously described (Seale et al., 2008). Primary white preadipocytes were FACS-sorted from subcutaneous (inguinal) white fat depots of 10-week-old mice as previously described (Rodeheffer et al., 2008). Fibro/adipogenic progenitors were FACS-sorted from hindlimb muscles of 10-week-old mice as previously described (Joe et al., 2010). FlowJo version 8.7 software suites were used to analyze FACS data.

Cell Culture:

C2C12 myoblasts and C3H10T1/2 mesenchymal progenitors were purchased from ATCC and cultured following manufacturer's recommendations. Primary myoblasts were derived from FACS-sorted satellite cells from homozygous Pax7-ZsGreen mice and were cultured in Ham's F-10 medium supplemented with 20% FBS and 2.5 ng/L bFGF. Preadipocytes and FAPs were cultured in DMEM supplemented with 20% FBS. Adipocyte differentiation was performed as previously described (Seale et al., 2008). For myogenic differentiation, cells were cultured in DMEM supplemented with 2% horse serum.

Indirect Calorimetry:

Whole-body $O_2$ consumption and $CO_2$ production was measured using an open circuit four-chamber indirect calorimetry system with automatic temperature and light controls (Columbus Instruments). Physical activities during indirect calorimetry was measured using infrared laser beam sets. Mice had access ad libitum to food and water in respiration chambers. Data were recorded for a 24 hour period with light between 06:00-18:00.

High-Resolution Respirometry:

Surgically extracted tibialis anterior (TA) and contralateral soleus (SOL) muscles were immediately placed in ice-cold biopsy preservation solution (BIOPS) containing 10 mM $CaK_2EGTA$ buffer, 7.23 mM $K_2EGTA$ buffer, 0.1 µM free calcium, 20 mM imidazole, 20 mM taurine, 50 mM 2-(N-Morpholino)ethanesulfonic acid hydrate (K-MES), 0.5 mM dithiothreitol (DTT), 6.56 mM $MgCl_2.GT_2O$, 5.77 mM ATP, and 15 mM phosphocreatine (pH 7.1). The TA muscle was cut longitudinally into 4 equal parts, 2 of which were assessed by respirometry as intact cells and 2 after chemical permeabilization of the sarcolemma. The SOL muscle was cut in half longitudinally and both sections were permeabilized before respirometry. Prior to permeabilization muscle samples were gently dissected with two pairs of sharp forceps, achieving a high degree of fibre separation verified microscopically. Chemical permeabilization was achieved by incubation of the fibres with saponin (50 µg/mL) in 2 mL of BIOPS for 30 minutes at 4° C. (Gnaiger, 2009b). Permeabilized samples were then rinsed with a mitochondrial respiration medium (MiR05) containing 0.5 mM EGTA, 3 mM $MgCl_2.6H_2O$, 60 mM K-lactobionate, 20 mM taurine, 10 mM $KH_2PO_4$, 20 mM HEPES, 110 mM sucrose, and 1 g/L bovine serum albumin (pH 7.1).

Mitochondrial Respiration:

Muscle bundles (both intact TA, and permeabilized TA and SOL) were blotted and measured for wet weight in a balance controlled for constant relative humidity, providing hydration consistency and stability of weight measurements. Each sample was then placed into a single chamber of the high-resolution Oroboros Oxygraph-2k (Oroboros, Innsbruck, Austria) containing MiR05 solution and measured at 37° C. The Oxygraph is a two-chamber titration-injection respirometer with an oxygen detection limit of up to 0.5 $pmol \cdot sec^{-1} \cdot mL^{-1}$. Standardized instrumental calibrations were performed to correct for back-diffusion of oxygen into the chamber from the various components, leak from the exterior, and sensor oxygen consumption. Oxygen flux was resolved by software allowing nonlinear changes in the negative time derivative of the oxygen concentration signal (Oxygraph 2k, Oroboros, Innsbruck, Austria).

Respiratory Titration Protocol:

Intact Cells:

Leak respiration was induced with the addition of malate (2 mM) and octanoyl carnitine (0.2 mM). This state represents the oxygen consumption of an unaltered and intact electron transport system (ETS) without the exogenous provision of adenylates. In the $L_N$ state, the chemiosmotic gradient is at maximum and oxygen flux represents proton leak, slip, and cation cycling in muscle (Pesta and Gnaiger, 2011) and maximal respiration in BAT induced by fatty acids (Matthias et al. 2000). Further uncoupling of the ETS in muscle cells was assessed with the proton ionophore, carbonyl cyanide p-(trifluoromethoxy) phenylhydrazone (FCCP; 0.7 µM per titration up to concentrations ranging from 2.5-4 µM) to achieve a maximal uncoupling response.

Permeabilized Cells:

Leak respiration in the absence of adenylates ($L_N$) was induced with the addition of malate (2 mM) and octanoyl carnitine (0.2 mM). Lipid oxidative phosphorylation capacity ($P_{ETF}$) and maximal electron flow through electron transferring-flavoprotein (ETF) was determined following the addition of ADP (5 mM). ETF is located on the matrix face of the inner mitochondrial membrane and supplies electrons from β-oxidation to coenzyme Q. The ETF linked transfer of electrons requires the metabolism of acetyl-CoA, requiring the addition of malate in order to facilitate convergent electron flow into the Q-junction from both CI and ETF allowing β-oxidation to proceed in permeabilized cells. The contribution of electron flow through CI is far below capacity and hence the rate limiting metabolic pathway is electron transport through ETF such that malate+octanoyl carnitine+ADP stimulated respiration is representative of, rather than specific to, electron capacity through ETF (Gnaiger, 2009a; Pesta and Gnaiger, 2011; Pesta et al., 2011; Saks et al., 1998). Maximal NADH dehydrogenase (Complex I-specific) state 3 respiratory capacity ($P_{CI}$) was induced with glutamate (10 mM) which inhibits electron transport through ETF, isolating the transport of electrons through CI (Saks et al., 1998). Maximal mitochondrial state 3 respiration and oxidative phosphorylation capacity (P) was induced with the addition of succinate (10 mM) through succinate dehydrogenase, (complex II), and represents the mitochondrial capacity to catalyze a sequential set of Redox reactions primarily coupled to the production of ATP via ATP synthase. Convergent electron input to CI and CII, elicits higher respiratory values compared to the isolated respiration of either CI (pyruvate+malate or glutamate+malate) or CII (succinate+rotenone) (Gnaiger, 2009a) and accordingly is the physiologically relevant to the study of maximal coupled mitochondrial respiration. Oligomycin (1 µM) was then added to inhibit ATP synthase demonstrating oligomycin-induced leak respiration ($L_{Omy}$) Finally, Antimycin A (2.5 µM) was added to terminate respiration by inhibiting cytochrome $bc_1$ complex, allowing for the determination of residual oxygen consumption in the oxygraph chamber. Experiments were carried out in a hyperoxygenated environment (chamber oxygen concentration maintained above 300 nmol/ml) to prevent potential limitations in oxygen diffusion at high cell respiration rates Finally, provision of the Redox substrates ascorbate (2 mM) and N,N,N',N'-tetramethyl-1,4-benzenediamine, dihydrochloride (TMPD, 5 mM) allowed for assessment of the isolated activity of cytochrome c oxidase (COX), the terminal respiratory chain complex that catalyzes the reduction of oxygen to water at the cytochrome aa3 subunit. Auto-oxidation of TMPD was corrected for by addition of sodium azide (100 mM). In permeabilized cell experiments, the oxygraph chambers were hyperoxynated (oxygen concentration above 300 nmol/L) to prevent potential oxygen diffusion limitation.

[$^{18}$F]-FDG PET Imaging and X-Ray Computed Tomography (CT):

Mouse PET imaging was performed with an Inveon PET scanner (Siemens Preclinical Solutions, Knoxyille, Tenn., USA). Control- or miR-133 ASO treated C57BL/6 male mice fed with regular diet were anesthetized under 2% isoflurane. Mice were administrated with ~1 mCi [$^{18}$F] fluoro-2-deoxyglucose ([$^{18}$F] FDG) via tail vein injection and subjected to an 80 minute dynamic scan. Data analysis was performed using the Inveon Research Workplace software to determine the standardize uptake values (SUVs) (activity concentration/injected dose×body weight) based on drawn regions of interest (ROI) at the end of the 80 minute scanning period. CT with hindlimbs centered in the field of view was performed before the microPET imaging. Reconstructed CT images were registered with microPET images to precisely identify TA muscles on hindlimbs. To activate brown adipocytes, a β3-adrenergic selective agonist, CL-316,243, was administrated (1 mg/kg body weight; I.P. injection) 20 minutes before the anesthesia.

Thermographic Imaging:

Mouse thermographic imaging was performed with a FUR T640 infrared camera with highest sensitivity set to ~35° C. Control- or miR-133 ASO treated C57BL/6 male mice fed with either a regular diet or a high fat diet were shaved at both of the hindlimbs one day before the imaging. Subject mice were quickly anesthetized under ~1% isoflurane and thermographic images were taken immediately after the mice were anesthetized (within 2 minutes). Data analysis was performed using FUR QuickReport software with measuring crosses set on the TA muscle areas on lower hindlimbs and the neck areas.

Transfection of MicroRNA Precursors and Inhibitors:

50 nM miR-133a and miR-133b Pre-miR™ Precursor (Ambion), 50 nM miR-133a/miR-133b PNA inhibitors (Panagene, Korea), or 50 nM miR-133a-1, miR-133a-2, miR-133b miRIDIAN hairpin inhibitors (Dharmacon) were transfected into target cells by Lipofectamine RNAiMax reagent (Invitrogen) following manufacturers' recommendations.

Plasmid Construction:

A 293 bp fragment of Prdm16 3' UTR region, containing the miR-133 target site, was amplified from genomic DNA by PCR (sense primer: 5'-ACTCGAGTTCTCTGCTTGGATGGGCT-3' (SEQ ID NO: 7); antisense primer: 5'-AGCGGCCGCGACAC-AGGGGTATTTGGCA-3' (SEQ ID NO:8)). To generate the psiCheck2-Prdm16_wtUTR, amplified Prdm16 3'UTR fragment was cloned into XhoI/NotI site on psiCheck2 plasmid (Promega). To generate the psiCheck2-Prdm16_mutUTR, a site-directed mutagenesis PCR was performed on the psiCheck2-Prdm16_wtUTR template with Phusion® Site-Directed Mutagenesis Kit (Thermo Scientific);

```
forward primer:
                                    SEQ ID NO: 9
5'-pGCCCCCGTGTGATAAGGTTGTGTGCTGTGTG-3';

reverse primer:
                                    SEQ ID NO: 10
5'-pCGTTTTCACTACATACTTATATTAACATCATTTCTTCAGAATAAG
TTGTCC-3'
```

For lentiviral overexpression of miR-133, a 619 bp region including the miR-133a hairpin precursor sequence was amplified from genomic DNA by PCR:

```
forward primer:
                                    SEQ ID NO: 11
5'-AGAATTCTGAGCTGCAAGAACAGCAGTGT-3';

reverse primer:
                                    SEQ ID NO: 12
5'-AGCGGCCGCTCCCATCATGTTTTTAGGTGAGTTTTTG-3'.
```

The amplified sequence was cloned into EcoRI/NotI sites of pCDH-CMV-MCS-EF1-Puro plasmid (System Biosciences).

Luciferase Assays:

For miR-133 targeting assays, HEK293T cells were co-transfected with combinations of psiCheck2-Prdm16_wtUTR plasmid with Pre-miR™ Negative Control #1 Precursor (Ambion), or psiCheck2-Prdm16_wtUTR plasmid with miR-133a Pre-miR™ Precursor (Ambion), or psiCheck2-Prdm16_mutUTR plasmid with miR-133a Pre-miR™ Precursor.

Immunofluorescence Staining:

The following antibodies and dilutions were used: anti-MyHC antibody (MF20, Developmental Studies Hybridoma Bank), 1:20 dilution; anti-Prdm16 antibody (generated in Dr. Patrick Seale's laboratory), 1:1,000 dilution; anti-Perilipin A antibody (Vala Sciences), 1:500 dilution; anti-Ucp1 antibody (Calbiochem), 1:200 dilution; anti-Laminin B2 antibody (Upstate), 1:500 dilution.

Immunoblotting:

The following antibodies and dilutions were used: anti-Prdm16 antibody (generated in Dr. Patrick Seale's laboratory), 1:5,000 dilution; anti-Perilipin A antibody (Vala Sciences), 1:5,000 dilution; anti-Ucp1 antibody (Ab10983, Abeam), 1:1,000 dilution (FIGS. 4B, 5A, 7A); anti-Ucp1 antibody (Calbiochem), 1:1,000 dilution (FIG. 8C); anti-Ucp3 antibody (Ab3477, Abeam), 1:1,000 dilution; anti-Pgc1α antibody (Abeam), 1:1,000 dilution; anti-pan myosin heavy chain (MyHC) antibody (Developmental Studies Hybridoma Bank), 1:500; anti-DsRed (tdTomato) antibody (Ablab), 1:500; anti-α-Tubulin antibody (Sigma-Aldrich), 1:10,000 dilution.

Immunohistochemistry (IHC):

Paraffin embedded tissue sections of TA muscles, inguinal white fat depots (igWAT) and epididymal white fat depots (epiWAT) were deparaffinized in CitriSolv. After rehydration, tissue sections were boiled in 0.01M citrate buffer (1.8 mM citric acid, 8.2 mM sodium citrate, pH 6.0) for 16 minutes. Endogenous peroxidase activity was neutralized by 0.3% $H_2O_2$ in 70% methanol Anti-Ucp1 antibody (Calbiochem) was 1:200 diluted and incubated with tissues sections overnight. IHC signals were developed by Vectastain ABC kit.

Quantitative Reverse Transcription PCR(RT-qPCR):

Total RNA was extracted from cells by TRIzol or Arcturus® PicoPure® RNA Isolation Kit (Applied Biosystems) following manufactures' recommendations. For RT-qPCR of mRNAs, total RNAs were reverse transcribed into cDNAs by SuperScript III (Invitrogen) and a mixture of oligodT$_{18-20}$ primers and random hexamers. microRNA RT-qPCRs were performed as previously described (Shi and Chiang, 2005). Primer sequences used in RT-qPCR for miR-133 were:

```
sense primer (5'-3')
                                    SEQ ID NO: 14
TTTCCTCCCCTTCAACCAGCTG antisense primer (5'-3')
                                    SEQ ID NO: 15
GCATACGAGCTCTTCCGATCT (universal)
```

Primer sequences used in RT-qPCR for the remaining genes are not provided here. Relative expression ratios were calculated by REST2009 (Qiagen).

Biosensor Generation and Testing:

Two miR-133 biosensor plasmids were constructed—pCMV-FireflyLuc_miR133TS_EF1_Puro and pCMV-RenillaLuc_133TS_EF1_Puro. In the pCMV-FireflyLuc_133TS_EF1_Puro plasmid, five tandem miR-133 target sites (miR133TS; 5'-TAGCTGGTTGCCAGGACCAAAA-3', SEQ ID NO:22) was cloned downstream of a firefly luciferase ORF (with a stop codon), which is driven by a CMV promoter. These miR-133 target sites in whole serve as an artificial 3' UTR of firefly luciferase transcript. The "GGAC-CAAA" sequence in the miR-133 target sites is complementary to the nucleotide positions 1-8 in miR-133a and miR-133b. The "TAGCTGGTTG" sequence in the miR-133 target sites is complementary to the nucleotide positions 13-22 in miR-133a and miR-133b. The remaining sequence "CCA" sequence in the middle will not anneal to the miR-133a or miR-133b, which will form a "bulge" structure when miR-133a/b anneal to the RNA transcript of miR-133 target sites. This fireflyLuc_miR133TS cassette was further cloned into a lentivirus backbone. In the pCMV-RenillaLuc_133TS_EF1_Puro plasmid, the firefly luciferase ORF was replaced by a *renilla* luciferase ORF. pCMV-FireflyLuc_miR133TS_EF1_Puro and pCMV-RenillaLuc_133TS_EF1_Puro plasmids were used to generate lentivirus particles in 293T cells, which were used to infect C2C12 myoblasts. Infected C2C12 myoblasts were selected by Puromycin (2 mg/L) and clonally expanded. C2C12 clones, C11 and C3, were used in subsequent experiments.

In one experiment, a C2C12 clone C11 (25,000 cells per well on 24-well plates), was transfected with 0.5 nM and 5 nM miR-133 mimetics (Life Technologies/Ambion), which can be processed into mature miR-133 in cells. As expected, the firefly luciferase activities in miR-133 mimetics transfected cells were significantly reduced. In another experiment, a C2C12 clone C3 (25,000 cells per well on 24-well plates) was transfected with 10 nM synthetic miR-133 inhibitors (antisense PNA oligonucleotides; PNABio), which can hybridize with endogenous miR-133 and hence block its function. As expected, the firefly luciferase activities in miR-133 inhibitors transfected cells were significantly increased. Both experiments were performed with 6 replicates and Z-scores above 0.5 were achieved.

In one experiment, a C2C12 clone (A10; 25,000 cells per well in 24-well plates) was treated with drugs and biologics for 48 hours in growth media. Luciferase assays indicated that TGF-β and Insulin are inhibitors of miR-133 whereas 3-isobutyl-1-methylxanthine (IBMX), Dexamethasone and 5' amino-1-βD-ribofuranosyl-imidazole-4-carboxamide (AICAR) are enhancers of miR-133. The concentrations used are: TGF-β: 10 ng/mL, IBMX: 0.5 mM, Indomethacin: 125 nM, Dexamethasone: 1 Rosiglitarzon: 1 µM, Triiodothyronine: 1 nM, Insulin: 850 nM, AICAR: 0.5 mM, Isoproterenol: 100 Foskolin: 25 µM.

The above-described embodiments are intended to be examples only. Alterations, modifications and variations can be effected to the particular embodiments by those of skill in the art without departing from the scope, which is defined solely by the claims appended hereto.

REFERENCES

Almind, K., Manieri, M., Sivitz, W. I., Cinti, S., and Kahn, C. R. (2007). Ectopic brown adipose tissue in muscle provides a mechanism for differences in risk of metabolic syndrome in mice. Proc Natl Acad Sci USA 104, 2366-2371.

Atit, R., Sgaier, S. K., Mohamed, O. A., Taketo, M. M., Dufort, D., Joyner, A. L., Niswander, L., and Conlon, R. A. (2006). Beta-catenin activation is necessary and sufficient to specify the dorsal dermal fate in the mouse. Dev Biol 296, 164-176.

Bachmanov, A. A., Reed, D. R., Beauchamp, G. K., and Tordoff, M. G. (2002). Food intake, water intake, and drinking spout side preference of 28 mouse strains. Behav Genet. 32, 435-443.

Bosnakovski, D., Xu, Z., Li, W., Thet, S., Cleaver, O., Perlingeiro, R. C., and Kyba, M. (2008). Prospective isolation of skeletal muscle stem cells with a Pax7 reporter. Stem Cells 26, 3194-3204.

Bowman, W. C., and Nott, M. W. (1969). Actions of sympathomimetic amines and their antagonists on skeletal muscle. Pharmacol Rev 21, 27-72.

Cannon, B., and Nedergaard, J. (2004). Brown adipose tissue: function and physiological significance. Physiol Rev 84, 277-359.

Charge, S. B., and Rudnicki, M. A. (2004). Cellular and molecular regulation of muscle regeneration. Physiol Rev 84, 209-238.

Chen, J. F., Mandel, E. M., Thomson, J. M., Wu, Q., Callis, T. E., Hammond, S. M., Conlon, F. L., and Wang, D. Z. (2006). The role of microRNA-1 and microRNA-133 in skeletal muscle proliferation and differentiation. Nat Genet. 38, 228-233.

Cypess, A. M., and Kahn, C. R. (2010). Brown fat as a therapy for obesity and diabetes. Curr Opin Endocrinol Diabetes Obes 17, 143-149.

Cypess, A. M., Lehman, S., Williams, G., Tal, I., Rodman, D., Goldfine, A. B., Kuo, F. C., Palmer, E. L., Tseng, Y. H., Doria, A., et al. (2009). Identification and importance of brown adipose tissue in adult humans N Engl J Med 360, 1509-1517.

Dellavalle, A., Maroli, G., Covarello, D., Azzoni, E., Innocenzi, A., Perani, L., Antonini, S., Sambasivan, R., Brunelli, S., Tajbakhsh, S., et al. (2011). Pericytes resident in postnatal skeletal muscle differentiate into muscle fibres and generate satellite cells. Nat Commun 2, 499.

Farmer, S. R. (2008). Brown fat and skeletal muscle: unlikely cousins? Cell 134 726.

Frontini, A., and Cinti, S. (2010). Distribution and development of brown adipocytes in the murine and human adipose organ. Cell Metab 11, 253-256.

Ghorbani, M., and Himms-Hagen, J. (1997). Appearance of brown adipocytes in white adipose tissue during CL 316, 243-induced reversal of obesity and diabetes in Zucker fa/fa rats. Int J Obes Relat Metab Disord 21, 465-475.

Gnaiger, E. (2009a). Capacity of oxidative phosphorylation in human skeletal muscle: new perspectives of mitochondrial physiology. Int J Biochem Cell Biol 41, 1837-1845.

Gnaiger, E. (2009b). Capacity of oxidative phosphorylation in human skeletal muscle: new perspectives of mitochondrial physiology. Int J Biochem Cell Biol 41, 1837-1845.

Granjon, A., Gustin, M. P., Rieusset, J., Lefai, E., Meugnier, E., Guller, I., Cerutti, C., Paultre, C., Disse, E., Rabasa-Lhoret, R., et al. (2009). The microRNA signature in response to insulin reveals its implication in the transcriptional action of insulin in human skeletal muscle and the role of a sterol regulatory element-binding protein-1c/myocyte enhancer factor 2C pathway. Diabetes 58, 2555-2564.

Gupta, R. K., Mepani, R. J., Kleiner, S., Lo, J. C., Khandekar, M. J., Cohen, P., Frontini, A., Bhowmick, D. C., Ye, L., Cinti, S., et al. (2012). Zfp423 expression identifies committed preadipocytes and localizes to adipose endothelial and perivascular cells. Cell Metab 15, 230-239.

Himms-Hagen J. (1979) Can Med Assoc J. 121(10):1361-4. Review.

Himms-Hagen J, Cui J, Danforth E Jr, Tootles D J, Lang S S, Waters B L, Claus T H. Am J. Physiol. (1994) 266(4 Pt 2):R1371-82.

Ishibashi, J. and Seale, P., (May 28, 2011). Beige can be Slimming Science 328(5982): 1113-1114.

Joe, A. W., Yi, L., Natarajan, A., Le Grand, F., So, L., Wang, J., Rudnicki, M. A., and Rossi, F. M. (2010). Muscle injury activates resident fibro/adipogenic progenitors that facilitate myogenesis. Nat Cell Biol 12, 153-163.

Kajimura, S., Seale, P., Tomaru, T., Erdjument-Bromage, H., Cooper, M. P., Ruas, J. L., Chin, S., Tempst, P., Lazar, M. A., and Spiegelman, B. M. (2008). Regulation of the brown and white fat gene programs through a PRDM16/CtBP transcriptional complex. Genes Dev 22, 1397-1409.

Kalaany, N. Y., Gauthier, K. C., Zavacki, A. M., Mammen, P. P., Kitazume, T., Peterson, J. A., Horton, J. D., Garry, D. J., Bianco, A. C., and Mangelsdorf, D. J. (2005). LXRs regulate the balance between fat storage and oxidation. Cell Metab 1, 231-244.

Kopecky, J., Clarke, G., Enerback, S., Spiegelman, B., and Kozak, L P (1995). Expression of the mitochondrial uncoupling protein gene from the aP2 gene promoter prevents genetic obesity. J Clin Invest 96, 2914-2923.

Krief, S., Lonnqvist, F., Raimbault, S., Baude, B., Van Spronsen, A., Arner, P., Strosberg, A. D., Ricquier, D., and Emorine, L. J. (1993). Tissue distribution of beta 3-adrenergic receptor mRNA in man J Clin Invest 91, 344-349.

Krutzfeldt, J., Rajewsky, N., Braich, R., Rajeev, K. G., Tuschl, T., Manoharan, M., and Stoffel, M. (2005). Silencing of microRNAs in vivo with cantagomirs'. Nature 438, 685-689.

Kuang, S., Kuroda, K., Le Grand, F., and Rudnicki, M. A. (2007). Asymmetric self-renewal and commitment of satellite stem cells in muscle. Cell 129, 999-1010.

Larsen, S., Nielsen, J., Hansen, C. N., Nielsen, L. B., Wibrand, F., Stride, N., Schroder, H. D., Boushel, R., Helge, J. W., Dela, F., et al. (2012). Biomarkers of mitochondrial content in skeletal muscle of healthy young human subjects. J Physiol 590, 3349-3360.

Lepper, C., and Fan, C. M. (2010). Inducible lineage tracing of Pax7-descendant cells reveals embryonic origin of adult satellite cells. Genesis 48, 424-436.

Matthias, A., Ohlson, K. B., Fredriksson, J. M., Jacobsson, A., Nedergaard, J., and Cannon, B. (2000). Thermogenic responses in brown fat cells are fully UCP1-dependent. UCP2 or UCP3 do not substitute for UCP1 in adrenergically or fatty scid-induced thermogenesis. J Biol Chem 275, 25073-25081.

Nedergaard, J., Bengtsson, T., and Cannon, B. (2007). Unexpected evidence for active brown adipose tissue in adult humans. Am J Physiol Endocrinol Metab 293, E444-452.

Nedergaard, J., Bengtsson, T., and Cannon, B. (2010). Three years with adult human brown adipose tissue. Ann N Y Acad Sci 1212, E20-36.

Nielsen, S., Scheele, C., Yfanti, C., Akerstrom, T., Nielsen, A. R., Pedersen, B. K., and Laye, M. J. (2010). Muscle specific microRNAs are regulated by endurance exercise in human skeletal muscle. J Physiol 588, 4029-4037.

Nishijo, K., Hosoyama, T., Bjornson, C. R., Schaffer, B. S., Prajapati, S. I., Bahadur, A. N., Hansen, M. S., Blandford, M. C., McCleish, A. T., Rubin, B. P., et al. (2009). Biomarker system for studying muscle, stem cells, and cancer in vivo. Faseb J 23, 2681-2690.

Ouellet, V., Labbe, S. M., Blondin, D. P., *Phoenix*, S., Guerin, B., Haman, F., Turcotte, E. E., Richard, D., and Carpentier, A. C. (2012). Brown adipose tissue oxidative metabolism contributes to energy expenditure during acute cold exposure in humans. J Clin Invest 122, 545-552.

Pesta, D., and Gnaiger, E. (2011). High-Resolution Respirometry. OXPHOS Protocols for Human Cell Cultures and Permeabilized Fibres from Small Biopsies of Human Muscle. Mitochondrial Bioenergetics Methods and Protocols 810, 25-58.

Pesta, D., Hoppel, F., Macek, C., Messner, H., Faulhaber, M., Kobel, C., Parson, W., Burtscher, M., Schocke, M., and Gnaiger, E. (2011) Similar qualitative and quantitative changes of mitochondrial respiration following strength and endurance training in normoxia and hypoxia in sedentary humans. Am J Physiol Regul Integr Comp Physiol 301, R1078-1087.

Pfannenberg, C., Werner, M. K., Ripkens, S., Stef, I., Deckert, A., Schmadl, M., Reimold, M., Haring, H. U., Claussen, C. D., and Stefan, N. (2010). Impact of age on the relationships of brown adipose tissue with sex and adiposity in humans Diabetes 59, 1789-1793.

Rodeheffer, M. S., Birsoy, K., and Friedman, J. M. (2008). Identification of white adipocyte progenitor cells in vivo. Cell 135, 240-249.

Rudnicki, M. A., Le Grand, F., McKinnell, I., and Kuang, S. (2008). The molecular regulation of muscle stem cell function. Cold Spring Harb Symp Quant Biol 73, 323-331.

Saito, M., Okamatsu-Ogura, Y., Matsushita, M., Watanabe, K., Yoneshiro, T., Nio-Kobayashi, J., Iwanaga, T., Miyagawa, M., Kameya, T., Nakada, K., et al. (2009). High incidence of metabolically active brown adipose tissue in healthy adult humans effects of cold exposure and adiposity. Diabetes 58, 1526-1531.

Saks, V. A., Veksler, V. I., Kuznetsov, A. V., Kay, L., Sikk, P., Tiivel, T., Tranqui, L., Olivares, J., Winkler, K., Wiedemann, F., et al. (1998). Permeabilized cell and skinned fiber techniques in studies of mitochondrial function in vivo. Mol Cell Biochem 184, 81-100.

Scime, A., Grenier, G., Huh, M. S., Gillespie, M. A., Bevilacqua, L., Harper, M. E., and Rudnicki, M. A. (2005). Rb and p107 regulate preadipocyte differentiation into white versus brown fat through repression of PGC-1alpha. Cell Metab 2, 283-295.

Seale, P., Bjork, B., Yang, W., Kajimura, S., Chin, S., Kuang, S., Scime, A., Devarakonda, S., Conroe, H. M., Erdjument-Bromage, H., et al. (2008). PRDM16 controls a brown fat/skeletal muscle switch. Nature 454, 961-967.

Seale, P., Conroe, H. M., Estall, J., Kajimura, S., Frontini, A., Ishibashi, J., Cohen, P., Cinti, S., and Spiegelman, B. M. (2011). Prdm16 determines the thermogenic program of subcutaneous white adipose tissue in mice. J Clin Invest 121, 96-105.

Seale, P., Kajimura, S., Yang, W., Chin, S., Rohas, L. M., Uldry, M., Tavernier, G., Langin, D., and Spiegelman, B. M. (2007). Transcriptional control of brown fat determination by PRDM16. Cell Metab 6, 38-54.

Seale, P., Sabourin, L. A., Girgis-Gabardo, A., Mansouri, A., Gruss, P., and Rudnicki, M. A. (2000). Pax7 is required for the specification of myogenic satellite cells. Cell 102, 777-786.

Shi, R., and Chiang, V. L. (2005). Facile means for quantifying microRNA expression by real-time PCR. Biotechniques 39, 519-525.

Tallquist, M. D., Weismann, K. E., Hellstrom, M., and Soriano, P. (2000). Early myotome specification regulates PDGFA expression and axial skeleton development. Development 127, 5059-5070.

Tran, K. V., Gealekman, O., Frontini, A., Zingaretti, M. C., Morroni, M., Giordano, A., Smorlesi, A., Perugini, J., De Matteis, R., Sbarbati, A., et al. (2012). The vascular endothelium of the adipose tissue gives rise to both white and brown fat cells. Cell Metab 15, 222-229.

van Marken Lichtenbelt, W. D., Vanhommerig, J. W., Smulders, N. M., Drossaerts, J. M., Kemerink, G. J., Bouvy, N. D., Schrauwen, P., and Teule, G. J. (2009). Cold-activated brown adipose tissue in healthy men. N Engl J Med 360, 1500-1508.

Virtanen, K. A., Lidell, M. E., Orava, J., Heglind, M., Westergren, R., Niemi, T., Taittonen, M., Laine, J., Savisto, N.

J., Enerback, S., et al. (2009). Functional brown adipose tissue in healthy adults. N Engl J Med 360, 1518-1525.

Walden, T. B., Timmons, J. A., Keller, P., Nedergaard, J., and Cannon, B. (2009). Distinct expression of muscle-specific microRNAs (myomirs) in brown adipocytes. J Cell Physiol 218, 444-449.

Wang, Y. X., and Rudnicki, M. A. (2011). Satellite cells, the engines of muscle repair. Nat Rev Mol Cell Biol 13, 127-133.

Williams, A. H., Liu, N., van Rooij, E., and Olson, E. N. (2009). MicroRNA control of muscle development and disease. Curr Opin Cell Biol 21, 461-469.

Wu, J., Bostrom, P., Sparks, L. M., Ye, L., Choi, J. H., Giang, A.-H., Khandekar, M., Virtanen, K. A., Nuutila, P., Schaart, G., Huang, K., Tu, H., van Markern Lichtenbelt, W., Hocks, J., Enerback, S., Schrauwen, P., Speigelman, B. M. (2012) Beige adipocytes are a disctinct type of thermogenic fat cell in mouse and human Cell 150 (2), 366-376.

Zingaretti, M. C., Crosta, F., Vitali, A., Guerrieri, M., Frontini, A., Cannon, B., Nedergaard, J., and Cinti, S. (2009). The presence of UCP1 demonstrates that metabolically active adipose tissue in the neck of adult humans truly represents brown adipose tissue. Faseb J 23, 3113-3120.

What is claimed is:

1. A method for treating obesity in a patient in need of such treatment, comprising administering to a patient an effective amount of an miRNA-133 inhibitor, wherein the miRNA-133 inhibitor is a nucleic acid that hybridizes to one or more mature miRNAs selected from miRNA-133a and miRNA-133b:

```
miR-133a:
5'-UUUGGUCCCCUUCAACCAGCUG-3'       (SEQ ID NO: 4)

miR-133b:
5'-UUUGGUCCCCUUCAACCAGCUA-3'.      (SEQ ID NO: 5)
```

2. The method of claim 1, wherein the inhibitor has at least 85%, 90%, 91%, or 95% sequence identity to a complement of the mature miRNA.

3. The method of claim 1, wherein the inhibitor is complementary to at least 10, 15, 17, 18, 19, 20, 21, or 22 contiguous nucleotides of the mature miRNA-133a or miRNA-133b.

4. The method of claim 1, wherein the inhibitor hybridizes to the mature miRNA under standard hybridization conditions.

5. The method of claim 1, wherein the inhibitor is complementary to the mature miRNA along the entire length of the mature miRNA.

6. The method of claim 1, wherein the inhibitor comprises the sequence

```
5'-GCUGGUUGAAGGGGACCAAA-3'      (SEQ ID NO: 16)
or
5'-GCTGGTTGAAGGGGACCAAA-3'.     (SEQ ID NO: 17)
```

7. The method of claim 1, wherein the inhibitor comprises the sequence

```
5'-UAGCUGGUUGAAGGGGACCAAA-3'    (SEQ ID NO: 18)

5'-TAGCTGGTTGAAGGGGACCAAA-3'    (SEQ ID NO: 19)
```

-continued

5'-CAGCUGGUUGAAGGGGACCAAA-3',   (SEQ ID NO: 20)
or

5'-C AGCTGGTTGAAGGGACCAAA-3'.   (SEQ ID NO: 21)

8. The method of claim 1, wherein the inhibitor comprises at least one modified nucleotide.

9. The method of claim 1, wherein the inhibitor is an antagomiR.

10. The method of claim 9, comprising the sequence: 5'*mA*mUmAmGmCmUmGmGmUmUmGmAmAmGm-GmGmGmAmC*mC*mA*mA*mAChl3' wherein
    m represents a 2'-O-methyl-modified nucleotide,
    * represents a phosphorothioate linkage, and
    Chl represents a 3' cholesterol moiety.

11. The method of claim 1, wherein the inhibitor is a peptide nucleic acid (PNA).

12. The method of claim 1, wherein the inhibitor is a locked-in nucleic acid.

13. The method of claim 1, further comprising treating type 2 diabetes.

14. A method for increasing the expression of PR domain containing 16 (Prdm16), comprising contacting cells that express Prdm16 with an effective amount of an miRNA-133 inhibitor, wherein the miRNA-133 inhibitor is a nucleic acid that hybridizes to one or more mature miRNAs selected from miRNA-133a and miRNA-133b:

```
                                          (SEQ ID NO: 4)
miR-133a: 5'-UUUGGUCCCCUUCAACCAGCUG-3'

SEQ ID NO: 5)
miR-133b: 5'-UUUGGUCCCCUUCAACCAGCUA-3',
wherein said hybridization results in increased
Prdm16 expression.
```

15. The method of claim 14, wherein the cells that express Prdm16 are myogenic cells, satellite cells, myoblasts, brown adipocyte progenitor cells, fibrogenic/adipogenic progenitors isolated from skeletal muscles, or brown pre-adipocytes.

16. A method for inducing energy-expending adipocytes comprising contacting cells with an effective amount of an miRNA-133 inhibitor, wherein the miRNA-133 inhibitor is a nucleic acid that hybridizes to one or more mature miRNAs selected from miRNA-133a and miRNA-133b:

```
                                          (SEQ ID NO: 4)
miR-133a: 5'-UUUGGUCCCCUUCAACCAGCUG-3'

SEQ ID NO: 5)
miR-133b: 5'-UUUGGUCCCCUUCAACCAGCUA-3',
wherein said hybridization results in induction
of energy-expending adipocytes.
```

* * * * *

UNITED STATES PATENT AND TRADEMARK OFFICE
CERTIFICATE OF CORRECTION

PATENT NO. : 9,018,188 B2
APPLICATION NO. : 14/241826
DATED : April 28, 2015
INVENTOR(S) : Michael A. Rudnicki et al.

Page 1 of 1

It is certified that error appears in the above-identified patent and that said Letters Patent is hereby corrected as shown below:

IN THE CLAIMS

Column 49, Line 60, Claim 1, delete "5)" and insert therefor -- 5), wherein said hybridization results in treatment for obesity. --.

Signed and Sealed this
Twenty-fourth Day of November, 2015

Michelle K. Lee
*Director of the United States Patent and Trademark Office*